United States Patent
June et al.

(10) Patent No.: US 7,638,326 B2
(45) Date of Patent: *Dec. 29, 2009

(54) ACTIVATION AND EXPANSION OF T-CELLS USING AN ENGINEERED MULTIVALENT SIGNALING PLATFORM

(75) Inventors: Carl June, Merion Station, PA (US); James Riley, Downingtown, PA (US); Marcela Maus, Wynnewood, PA (US); Anna Thomas, Freiburg (DE); Robert Vonderheide, Merion Station, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 255 days.

This patent is subject to a terminal disclaimer.

(21) Appl. No.: 10/462,207

(22) Filed: Jun. 13, 2003

(65) Prior Publication Data

US 2004/0110290 A1 Jun. 10, 2004

Related U.S. Application Data

(63) Continuation-in-part of application No. 10/336,224, filed on Jan. 3, 2003.

(60) Provisional application No. 60/346,092, filed on Jan. 3, 2002.

(51) Int. Cl.
 C12N 5/02 (2006.01)
 C12N 5/06 (2006.01)
 C12N 15/00 (2006.01)
 C12N 15/63 (2006.01)
 C07K 16/00 (2006.01)

(52) U.S. Cl. .................. 435/325; 435/326; 435/440; 435/455

(58) Field of Classification Search .................. None
 See application file for complete search history.

(56) References Cited

U.S. PATENT DOCUMENTS

| | | | |
|---|---|---|---|
| 5,166,320 A | 11/1992 | Wu et al. | |
| 5,190,878 A | 3/1993 | Wilhelm | |
| 5,529,921 A | 6/1996 | Peterson et al. | |
| 5,827,642 A | 10/1998 | Riddell et al. | |
| 5,858,358 A | 1/1999 | June et al. | |
| 5,888,807 A | 3/1999 | Palsson et al. | |
| 5,962,320 A | 10/1999 | Robinson | |
| 5,985,653 A | 11/1999 | Armstrong et al. | |
| 6,001,365 A | 12/1999 | Peterson et al. | |
| 6,096,532 A | 8/2000 | Armstrong et al. | |
| 6,352,694 B1 | 3/2002 | June et al. | |
| 6,355,479 B1 | 3/2002 | Webb et al. | |
| 6,464,973 B1 | 10/2002 | Levitsky et al. | |
| 6,534,055 B1 | 3/2003 | June et al. | |
| 6,867,041 B2 | 3/2005 | Berenson et al. | |
| 6,887,466 B2 | 5/2005 | June et al. | |
| 6,890,753 B2 | 5/2005 | Flyer et al. | |
| 6,905,681 B1 | 6/2005 | June et al. | |
| 6,905,874 B2 | 6/2005 | Berenson et al. | |
| 7,175,843 B2 | 2/2007 | June et al. | |
| 2002/0058019 A1 | 5/2002 | Berenson et al. | |
| 2002/0119568 A1 | 8/2002 | Berenson et al. | |
| 2003/0147869 A1 | 8/2003 | Riley et al. | |
| 2003/0224520 A1 | 12/2003 | June et al. | |
| 2004/0101519 A1 | 5/2004 | June et al. | |
| 2004/0191235 A1 | 9/2004 | Groux et al. | |
| 2004/0241162 A1 | 12/2004 | Berenson et al. | |
| 2005/0003484 A1* | 1/2005 | Hirano et al. | ............ 435/69.1 |
| 2006/0034810 A1 | 2/2006 | Riley et al. | |
| 2006/0121005 A1 | 6/2006 | Berenson et al. | |

FOREIGN PATENT DOCUMENTS

| | | |
|---|---|---|
| WO | WO95/00642 | 1/1995 |
| WO | WO95/03408 | 2/1995 |
| WO | WO 95/33823 | 12/1995 |
| WO | WO99/36093 | 7/1999 |
| WO | WO00/25813 | 5/2000 |
| WO | WO 03/006632 | 1/2003 |
| WO | WO03/057171 | 7/2003 |
| WO | WO03/065977 | 8/2003 |

OTHER PUBLICATIONS

Zhu et al. The Journal of Immunology, 2001 167:2671-2676.*
Zamai et al. Eur. J. Histochem. 1994 38 suppl I:53-60.*
Yotnda et al. J. Clin. Invest. 1998 101;10:2290-2296.*
ATCC Cell Lines and Hybridomas 1994 8th Edition, p. 129.*
Britten et al. Journal of Immunological Methods. 2002, 259:95-110.*
Fanger et al. The Journal of Immunology, 1996, 157:541-548.*
San Jose et al. Eur. J. Immunol. 1998. 28:12-21.*
Thomas, A.K. et al., "A Cell-Based Artificial Antigen-Presenting Cell Coated with Anti-CD3 and CD28 Antibodies Enables Rapid Expansion and Long-Term Growth of CD4 T Lymphocytes," *Clinical Immunology* 105(3): 259-272, Dec. 2002.
Altman et al., "Phenotypic Analysis of Antigen-Specific T Lymphocytes," *Science* 274:94-96, Oct. 1996.
Brodie et al., "In Vivo Migration and Function of Transferred HIV-1-Specific Cytotoxic T Cells," *Nature Medicine* 5(1):34-41, Jan. 1999.
Chapoval et al., "B7-H3: A Costimulatory Molecule for T Cell Activation and IFN-$\gamma$ Production," *Nature Immunology* 2(3):269-274, Mar. 2001.
Dudley et al., "Adoptive Transfer of Cloned Melanoma-Reactive T Lymphocytes for the Treatment of Patients with Metastatic Melanoma," *J. of Immunotherapy* 24(4):363-373, Jul./Aug. 2001.
Dunbar et al., "Direct Isolation, Phenotyping and Cloning of Low-Frequency Antigen-Specific Cytotoxic T Lymphocytes from Peripheral Blood," *Current Biology* 8(7):413-416, Mar. 1998.
Curtsinger et al., "CD8$^+$ Memory T Cells (CD44$^{high}$, Ly-6C$^+$) Are More Sensitive than Naïve Cells (CD44$^{low}$, Ly-6C$^-$) to TCR/CD8 Signaling in Response to Antigen," *J. of Immunol.* 160:3236-3243, 1998.

(Continued)

Primary Examiner—Maher M Haddad
Assistant Examiner—Chun Dahle
(74) Attorney, Agent, or Firm—Drinker Biddle & Reath LLP

(57) ABSTRACT

The present invention relates generally to methods for activating and expanding cells, and more particularly, to a novel method to activate and/or stimulate cells using an engineered multivalent signaling platform. Compositions of cells activated and expanded by the methods herein are further provided.

15 Claims, 15 Drawing Sheets

OTHER PUBLICATIONS

Dong et al., "B7-H1, A Third Member of the B7 Family, Co-Stimulates T-Cell Proliferation and Interleukin-10 Secretion," *Nature Medicine* 5(12):1365-1369, Dec. 1999.

Freeman et al., "Engagement of the PD-1 Immunoinhibitory Receptor by a Novel B7 Family Member Leads to Negative Regulation of Lymphocyte Activation," *J. of Exp. Medicine* 192:1027-1034, 2000.

Guinn et al., "4-1BBL Cooperates with B7-1 and B7-2 in Converting a B Cell lymphoma Cell Line into a Long-Lasting Antitumor Vaccine," *J. of Immunol.* 162:5003-5010, 1999.

Heslop et al., "Long-Term Restoration of Immunity Against Epstein-Barr Virus Infection by Adoptive Transfer of Gene-Modified Virus-Specific T Lymphocytes," *Nature Medicine* 2(5):551-555, May 1996.

Hurtado et al., "Potential Role of 4-1BB in T Cell Activation," *J. of Immunol.* 155:3360-3367, 1995.

Hurtado et al., "Signals Through 4-1BB are Costimulatory to Previously Activated Splenic T Cells and Inhibit Activation-Induced Cell Death," *J. of Immunol.* 158:2600-2609, 1997.

Iezzi et al., "The Duration of Antigenic Stimulation Determines the Fate of Naive and Effector T Cells," *Immunity* 89(1):89-95, Jan. 1998.

Kato et al., "Gene Transfer of CD40-Ligand Induces Autologous Immune Recognition of Chronic Lymphocytic Leukemia B Cells," *J. of Clinical Investigation* 101(5):1133-1141, Mar. 1998.

Latchman et al., "PD-L2 is a Second Ligand for PD-1 and Inhibits T Cell Activation," *Nature Immunology* 2(3):261-268, Mar. 2001.

Levine et al., "Effects of CD28 Costimulation on Long-Tern Proliferation of CD4$^+$ T Cells in the Absence of Exogenous Feeder Cells," *J. of Immunol.* 159(12):5921-5930, 1997.

Li et al., "IL-15 and IL-2: A Matter of Life and Death for T Cells in Vivo," *Nature Medicine* 7(1):114-118, Jan. 2001.

Liebowitz et al., "Costimulatory Approaches to Adoptive Immunotherapy," *Curr. Opin. in Onc.* 10(6):533-541, Nov. 1998.

Maus et al., "Ex Vivo Expansion of Polyclonal and Antigen-Specific Cytotoxic T Lymphocytes by Artificial APCs Expressing Ligands for the T-Cell Receptor, CD28 and 4-1BB," *Nature Biotech.* 20:143-148, Feb. 2002.

Melero et al., "Amplification of Tumor Immunity by Gene Transfer of the Co-Stimulatory 4-1BB Ligand: Synergy with the CD28 Co-Stimulatory Pathway," *Eur. J. of Immunol.* 28(3):1116-1121, Mar. 1998.

Melero et al, Monoclonal Antibodies Against the 4-1BB T-Cell Activation Molecule Eradicate Established Tumors, *Nature Medicine* 3(6):682-685, Jun. 1997.

Melief et al., "T-Cell Immunotherapy of Tumors by Adoptive Transfer of Cytotoxic T Lymphocytes and by Vaccination with Minimal Essential Epitopes," *Immunological Reviews* 146:167-177, 1995.

Ranheim et al., "Activated T Cells Induce Expressions of B7/BB1 on Normal or Leukemic B Cells Through a CD40-Dependent Signal," *J. of Exp. Med.* 177(4):925-935, Apr. 1993.

Riddell et al., "The Use of Anti-CD3 and Anti-CD28 Monoclonal Antibodies to Clone and Expand Human Antigen-Specific T Cells," *J. of Immunological Methods* 128(2)189-201, 1990.

Riddell et al., "The Fred Hutchinson Cancer Research Center and the University of Washington School of Medicine, Department of Medicine, Division of Oncology Oct. 7, 1991," *Human Gene Therapy* 3(3):319-338, Jun. 1992.

Riddell et al., "Principles for Adoptive T Cell Therapy of Human Viral Diseases," *Annu. Rev. Immunol.* 13:545-586, 1995.

Riddell et al., "Restoration of Vital Immunity in Immunodeficient Humans by the Adoptive Transfer of T Cell Clones," *Science* 257:238-241, Jul. 1992.

Rooney et al., "Infusion of Cytotoxic T Cells for the Prevention of and Treatment of Epstein-Barr Virus-Induced Lymphoma in Allogeneic Transplant Recipients," *Blood* 92(5):1549-1555, Sep. 1998.

Rosenberg et al., "Gene Transfer into Humans—Immunotherapy of Patients with Advanced Melanoma, using Tumor-Infiltrating Lymphocytes Modified by Retroviral Gene Transduction," *N. Engl. J of Med.* 323(9)570-578, Aug. 1990.

Rosenberg et al., "Use of Tumor-Infiltrating Lymphocytes and Interleukin-2 in the Immunotherapy of Patients with Metastatic Melanoma," *N. Eng. J. of Med.* 319(25):1676-1680, Dec. 1988.

Sagerström et al., "Activation and Differentiation Requirements of Primary T Cells in Vitro," *Proc. Natl. Acad. Sci.* 90:8987-8991, Oct. 1993.

Saoulli et al., "CD-28 Independent, TRAF2-Dependent Costimulation of Resting T Cells by 4-1BB Ligand," *J. Exp. Med.* 187(1):1849-1862, Jun. 1998.

Shuford et al., "4-1BB Costimulatory Signals Preferentially Induce CD8$^+$ T Cell Proliferation and Lead to the Amplification in Vivo of Cytotoxic T Cell Responses," *J. Exp. Med.* 186(1):47-55, Jul. 1997.

Takahashi et al., "Cutting Edge: 4-1BB Is a Bona Fide CD8 T Cell Survival Signal," *J. of Immunol.* 162:5037-5040, 1999.

Tan, "Autoantibodies as Reporters Identifying Aberrant Cellular Mechanics in Tumorigenesis," *J. of Clin. Invest.* 108(10):1411-1415, Nov. 2001.

Tan et al., "4-1BB Costimulation Is Required for Protective Anti-Viral Immunity After Peptide Vaccination," *J. of Immunol.* 164:2320-2325, 2000.

Tseng et al., "B7-DC, a New Dendritic Cell Molecule with Potent Costimulatory Properties for T Cells," *J. Exp. Med.* 193(7):839-845, Apr. 2001.

Voltz et al., "A Serologic Marker of Paraneoplastic Limbic and Brain-Stem Encephalitis in Patients with Testicular Cancer," *N. Eng. J of Med.* 340(23):1788-1795, Jun. 1999.

Wang et al., "Naïve CD8$^+$ T Cells Do Not Require Costimulation for Proliferation and Differentiation into Cytotoxic Effector Cells," *J. of Immunol.* 164:1216-1222, 2000.

Wells et al., "Following the Fate of Individual T Cells Throughout Activation and Clonal Expansion," *J. Clin. Invest.* 100(12):3173-3183, Dec. 1997.

Yee et al., "Isolation of High Avidity Melanoma-Reactive CTL from Heterogenous Populations using Peptide-MHC Tetramers," *J. of Immunol.* 162:2227-2234, 1999.

Yee et al., "In Vivo Tracking of Tumor-Specific T Cells," *Curr. Opin. Immunol.* 13:141-146, 2001.

Yee et al., "Melanocyte Destruction After Antigen-Specific Immunotherapy of Melanoma: Direct Evidence of T Cell-Mediated Vitiligo," *J. of Exp. Med.* 192(11):1637-1643, Dec. 2000.

Abendroth et al., 2000, J Gen Virol 81(Pt 10):2375-2383.

Afanasyeva et al., 2001 Circulation 104(25):3145-3151.

Alexander-Miller, et al., 1996, Proc Natl Acad Sci USA 93(9):4102-4107.

Almand, et al., 2000, Clin Cancer Res. 6:1755-1766.

Assoian et al., 1987, Proc Natl Acad Sci USA 84(17):6020-6024.

Bamford, et al., 1998, J Immunol 160:4418-26.

Brierer et al., 1991, Adv Cancer Research 56:49-76.

Bretscher 1992 Immunol Today 13:74-76.

Byun et al., 1994 J Immunol 153:4862-71.

Carroll et al., 1997, Science 276 (5310):273-276.

Claret et al., 1997 J Clin Invest 100(4):855-66.

Coyle et al., 2000, Immunity 13(1):95-105.

Curiel, 2004, Nat Med 10(9):942-949.

Dahl et al., 2000 J Exp Med 191(12):2031-8.

DeBenedette et al., 1997, J. Immunol 158:551-559.

Deeks et al., 2002, Mol Ther 5(6):788-797.

Deeths et al., 1997 Eur J Immunol 27:598-608.

Deeths et al., 1999, J Immunol 163:102-110.

Dietz et al., 2001, Cytotherapy 3(2):97-105.

Dull et al., 1998, J Virol 72(11):8463-8471.

Esslinger et al., 2002, Hum Gene Ther 13(9):1091-1100.

Flamand et al., 1998, Proc Natl Acad Sci USA 95(6):3111-3116.

Fraser, et al., 1991 Science 251(4991):313-16.

Gett et al., 1998 Proc Natl Acad Sci USA 95(16):9488-93.

Gett et al., 2000, Nature Immunology 1(3):239-244.

Gillis et al., 1977, Nature 268:154-156.

Gimmi et al., 1991 Proc Natl Acad Sci USA 88:6575-6579.

Gonzalo et al., 2001, Nat Immunol, 2(7):597-604.

Goodwin, et al., 1993, Eur J. Immunol 23(10):2631:2641.

Grosenbach et al., 2003, Cellular Immunol 222(1):45-57.

Groux et al., 1993, Eur J Immunol 23(7):1623-1629.

Gupta et al., 1999, J Leukoc Biol 66(1):135-143.

Hansen et al., 1980 Immunogenetics 10:247-260.

Harding et al., 1992, Nature 356 (6370):607-609.

Hoffmann et al., 2004, Blood 104(3):895-903.

Hutloff et al., 1999, Nature 397(6716):263-266.
Imlach et al., 2001 J Virol 75(23):11555-11564.
Jelley-Gibbs et al., 2000 J. Immunol. 165(9):5017-5026.
Jenkins et al., 1993, Curr Opin Immunol 5(3):361-367.
June et al., 1987 Mol Cell Biol. 7(12):4472-4481.
June et al., 1994, Immunol Today 15(7):321-331.
Kabelitz, et al., 1992, Int Immunol 4(12):1381-1388.
Kahl et al., 2004, J Virol 78(3):1421-1430.
Kawabe, et al., 1991, Nature, 349(6306):245-248.
Koenig et al., 1995, Nat Med 1(4):330-336.
Krummel 1996, J Exp Med 183(6):2533-2540.
Ku et al., 2000 Science 288(5466):675-678.
Kung et al., 1979 Science 206(4416):347-349.
Kurys et al., 2000, J Biol Chem 275(2):30653-30659.
Latouche et al., 2000 Nat Biotechnol 18:405-409.
Laux et al., 2000, Clinical Immunology 96(3):187-197.
Lee et al., 2002, Vaccine 20:A8-A22.
Lenschow et al.,1992, Science 257:789-792.
Levine et al., 1995, Inter Immunol 7(6):891-904.
Levine et al., 1996, Science 272 (5270):1939-1943.
Levine et al., 2002, Nat Med 8(1):47-53.
Lieberman et al., 1997, Blood 90(6):2196-2206.
Lindsten et al., 1989, Science, 244 (4902):339-343.
Linsley et al., 1993, Annu Rev Immunol 11:191-212.
Lord et al., 1998, J Immunol 161(9):4627-4633.
Lozzio, 1975, Blood, 45(3):321-334.
Malefyt et al. 1993, J Immunol 150(11):4754-4765.
Marks-Konczalik et al., 2000, Proc Natl Acad Sci USA 97(21):11445-11450.
Maus et al., 2003 Clin Immunol 106(1):16-22.
Mitsuyasu et al, 2000, Blood 96(3):785-793.
Muller et al., 1999, Immunology 97(2):280-286.
Musso et al., 1999, Blood 93(10):3531-3539.
Niethammer et al., 2002, Vaccine 20(3-4):421-429.
O'Doherty et al., 2000 J Virol 74(21):10074-10080.
Oh et al., 2003 J Immunol 170(5):2523-2530.
Parry et al., 2003, J Immunol 171(1)166-174.
Pollok et al., 1993, J Immunol 150(3):771-781.
Prakken et al., 2000, Nat Med 6(12):1406-1410.
Qiao et al., 1999 Cancer Gene Ther 6(4):373-379.
Rabinovitch, 1983, Proc Natl Acad Sci USA 80(10):2951-2955.
Ranga et al., 1998, Proc Natl Acad Sci USA 95(3)1201-1206.
Refaeli et al., 1998, Immunity 8(5):615-623.
Riddell et al., 1992, Hum Gene Ther 3(3):319-338.
Riddell et al., 1990, J Immunol Methods 128(2):189-201.
Riddell et al., 1996, Nature Med 2(2):216-223.
Riddell et al., 2000, Cancer J 6:S250-S258.
Riley et al., 1997, J. Immunol 158(11):5545-5553.
Riley et al., 2001, J Immunol, 166(8):4943-4948.
Rooney et al., 1995, Lancet 345(8941):9-13.
Sakaguchi, 2005, Nat Immunol 6(4):345-352.
Salomon, 2000, Immunity 12(4):431-440.
Schlienger et al., 2000, Blood 96(10):3490-3498.
Scholler et al., 2001, J Immunol 166(6):3865-3872.
Scholler et al., 2002, J Immunol 168(6):2599-2602.
Schwartz, 1990 Science, 248 (4961):1349-1356.
Schwartz, 1992, Cell 71(7):1065-1068.
Schwartz et al., 2001, Nature, 410(6828):604-608.
Schwartz et al., 2002, Nat Immunol 3(5):427-434.
Shedlock et al., 2003, Science 300:337-339.
Shibuya et al., 1999, Arch Otolaryngol Head Neck Surg. 125(11):1229-1234.
Smith et al., 1979 Ann NY Acad Sci 332:423-432.
Springer et al., 1987, Ann Rev Immunol 5:223-252.
Stripcke et al., 2000, Blood 96(4):1317-1326.
Sun et al., 2003, Science 300:339-342.
Tagaya et al., 1997, Proc Natl Acad Sci USA 94(26):14444-14449.
Topp et al., 2003, J Exp Med 198(6):947-955.
Turka et al., 1992, Proc Natl Acad Sci USA 89(22):11102-11105.
Van de Winkel et al., 1993, Immunol Today 14(5):215-221.
Van Parijs et al., 1999, Immunity 11(3):281-288.
Viguier et al., 2004, J Immunol 173(2):1444-1453.
Vieweg et al., 2004 Expert Opin Biol Ther 4(11):1791-1801.
Vonderheide et al., 1999, Immunity, 10(6):673-679.
Vonderheide et al., 2003, Immunol Res 27(2-3):341-356.
Vonderheide et al., 2004, Clin Cancer Res. 10(3):828-839.
Walker et al., 2000, Blood 96(2):467-474.
Walter et al., 1995, N Engl J Med 333(16):1038-1044.
Wakasugi et al., 1983 Proc Natl Acad Sci USA 80(19):6028-6031.
Warrington et al., 2003, Blood 101(9):3543-3549.
Webb et al., 1990, Cell 63(6):1249-1256.
Wells et al., 2000, J Immunol 165(5):2432-2443.
Weng et al., 1997, J Immunol 158(7):3215-3220.
Yee et al., 2002, Proc Natl Acad Sci USA 99(25):16168-16173.
Zajac et al., 1998, J Exp Med 188:2205-2213.
Zhang et al., 2004, Immunity 20(3):337-347.
Zufferey et al., 1998, J Virol 72(12):9873-9880.

* cited by examiner

ACTIVATION AND EXPANSION OF T-CELLS USING AN ENGINEERED MULTIVALENT SIGNALING PLATFORM

BACKGROUND OF THE INVENTION

1. Field of the Invention

The present invention relates generally to methods for stimulating and activating cells, and more particularly, to methods to activate and expand cells using an engineered multivalent signaling platform. The present invention also relates to methods for generating engineered multivalent signaling platform and methods of using same.

2. Description of the Related Art

Immunotherapy involving the priming and expansion of T lymphocytes (T cells) holds promise for the treatment of cancer and infectious diseases, particularly in humans (Melief et al., Immunol. Rev. 145:167-177 (1995); Riddell et al., Annu. Rev. Immunol. 13:545-586 (1995)). Current studies of adoptive transfer in patients with HIV, CMV, and melanoma involve the infusion of T cells that have been stimulated, cloned and expanded for many weeks in vitro on autologous dendritic cells (DC), virally infected B cells, and/or allogeneic feeder cells (Riddell et al., Science 257:238-241 (1992); Yee et al., J. Exp. Med. 192:1637-1644 (2000); Brodie et al., Nat. Med. 5:34-41 (1999); Riddell et al., Hum. Gene Ther. 3:319-338 (1992), Riddell et al., J. Immunol. Methods 128: 189-201 (1990)). However, adoptive T cell immunotherapy clinical trials commonly use billions of cells (Riddell et al., 1995). In order to produce these quantities of cells, many fold expansion of T cells in vitro (e.g., 40 population doublings) is usually required. Furthermore, for optimal engraftment potential and possible therapeutic benefit, it is important to ensure that the T cells, after in vitro expansion, are functional, and not senescent, at the time of re-infusion.

Naturally occurring T cell activation is initiated by the engagement of the T cell receptor/CD3 complex (TCR/CD3) by a peptide-antigen bound to a major histocompatibility complex (MHC) molecule on the surface of an antigen-presenting cell (APC) (Schwartz, Science 248:1349 (1990)). While this is the primary signal in T cell activation, other receptor-ligand interactions between APCs and T cells are required for complete activation. For example, TCR stimulation in the absence of other molecular interactions can induce a state of anergy, such that these cells cannot respond to full activation signals upon restimulation (Schwartz, 1990; Harding, et al., Nature 356:607 (1992)). In the alternative, T cells may die by programmed cell death (apoptosis) when activated by TCR engagement alone (Webb et al., Cell 63:1249 (1990); Kawabe et al., Nature 349:245 (1991); Kabelitz et al., Int. Immunol. 4:1381 (1992); Groux et al., Eur. J. Immunol. 23:1623 (1993)).

Multiple receptor-ligand interactions take place between the T cell and the APC, many of which are adhesive in nature, reinforcing the contact between the two cells (Springer et al., Ann. Rev. Immunol. 5:223 (1987)), while other interactions transduce additional activation signals to the T cell (Bierer et al., Adv. Cancer Res: 56:49 (1991)). For example, CD28 is a surface glycoprotein present on 80% of peripheral T cells in humans and is present on both resting and activated T cells. CD28 binds to B7-1 (CD80) or B7-2 (CD86) and is the most potent of the known co-stimulatory molecules (June et al., Immunol. Today 15:321 (1994); Linsley et al., Ann. Rev. Immunol. 11:191 (1993)). CD28 ligation on T cells in conjunction with TCR engagement induces the production of interleukin-2 (IL-2) (June et al., 1994; Jenkins et al., 1993; Schwartz, 1992). While the exact in vivo role of IL-2 is still in question, there is little doubt that IL-2 is a critical factor for ex vivo T cell expansion (Smith et al., Ann. N.Y. Acad. Sci. 332:423-432 (1979); Gillis et al., Nature 268:154-156 (1977)).

Recently, several new co-stimulatory molecules have been discovered based on their homology with the B7 and CD28 families. PD-1 is expressed on activated T cells and has two B7 like ligands, PD-L1 and PD-L2. Presently, it is unclear whether PD-1 ligation delivers an inhibitory (Freeman et al., J. Exp. Med. 192:1027-1034 (2000); Latchman et al., Nat. Immunol. 2:261-268 (2001)) or co-stimulatory signal (Dong et al., Nat. Med. 5:1365-1369 (1999); Tseng et al., J. Exp. Med. 193:839-846 (2001)) to T cells. B7-H3, which does not bind to CD28, CTLA-4, ICOS or PD-1, may act as a co-stimulatory molecule for T cell activation and IFN-γ production (Chapoval et al., Nat. Immunol. 2:269-274 (2001)).

The TNF receptor family member 4-1BB (CD137) was initially identified in receptor screens of activated lymphocytes (Pollok, K. E. et al., T cell J. Immunol. 150, 771-781 (1993)). The 4-1BB ligand is expressed by activated B cells, dendritic cells, and monocytes/macrophages, all of which can act as APCs (Goodwin, R. G et al., T cell Eur. J. Immunol. 23, 2631-2641 (1993)). Previous studies have shown that 4-1BB is a co-stimulatory molecule in the activation of T cells, and its signaling is independent from, albeit weaker than, CD28 signaling (Hurtado, J. C., et al., T cell J. Immunol. 158, 2600-2609 (1997); Hurtado, J. C., et al., T cell J. Immunol. 155, 3360-3367 (1995); Saoulli, K. et al., T cell J. Exp. Med. 187, 1849-1862 (1998)). 4-1BB stimulation preferentially activates $CD8^+$ T cells in vitro and amplifies generation of CTL responses in vivo (Shuford, W. W. et al., T cell T cell J. Exp. Med. 186, 47-55 (1997)). The mechanism for this effect may involve improved survival of activated CTLs (Takahashi, C., et al., J. Immunol. 162, 5037-5040 (1999)). Consistent with these data, co-stimulation of 4-1BB has been shown to have anti-viral and anti-tumor effects (Tan, J. T. et al., J. Immunol. 164, 2320-2325 (2000); Melero, I. et al., Nat. Med. 3, 682-685 (1997); Melero, I. et al., Eur J. Immunol. 28, 1116-1121 (1998); DeBenedette, M. A., et al., J. Immunol. 158, 551-559 (1997); Guinn, B. A., et al., J. Immunol. 162, 5003-5010 (1999)).

Co-stimulation of T cells has been shown to affect multiple aspects of T cell activation (June et al., 1994, Supra). It lowers the concentration of anti-CD3 required to induce a proliferative response in culture (Gimmi et al., Proc. Natl. Acad. Sci. USA 88:6575 (1991)). CD28 co-stimulation also markedly enhances the production of lymphokines by helper T cells through transcriptional and post-transcriptional regulation of gene expression Lindsten et al., Science 244:339 (1989); Fraser et al., Science 251:313 (1991)), and can activate the cytolytic potential of cytotoxic T cells. Inhibition of CD28 co-stimulation in vivo can block xenograft rejection, and allograft rejection is significantly delayed (Lenschow et al., Science 257:789 (1992); Turka et al., Proc. Natl. Acad. Sci. USA 89:11102 (1992)).

Methods of expanding T cell clones and/or lines for adoptive immunotherapy have proven to have certain drawbacks. The standard culture of pure $CD8^+$ cells is limited by apoptosis, diminution of biological function and/or proliferation, and obtaining a sufficient number of cells to be useful has been particularly difficult. Current cell culture techniques may require several months to produce sufficient numbers of cells from a single clone (Riddell et al., 1992; Heslop et al., Nat. Med. 2:551-555 (1996)), which is a problematic limiting factor in the setting of malignancy. Indeed, it is possible that such the T cells that are currently infused into patients, may have a limited replicative capacity, and therefore, could not stably engraft to provide long-term protection from disease. Furthermore, the various techniques available for expanding human T cells have relied primarily on the use of accessory cells (i.e. cells that support or promote T cell survival and proliferation such as PBMC or DC, B cells, monocytes, etc.) and/or exogenous growth factors, such as interleukin-2 (IL-2). IL-2 has been used together with an anti-CD3 antibody to stimulate T cell proliferation. Both primary and secondary APC signals are thought to be required for optimal T cell activation, expansion, and long-term survival of the T cells upon re-infusion. The requirement for accessory cells presents a significant problem for long-term culture systems because these cells are relatively short-lived. Therefore, in a long-term culture system, APCs must be continually obtained from a source and replenished. The necessity for a renewable supply of accessory cells is problematic for treatment of immunodeficiencies in which accessory cells are affected. In addition, when treating viral infection, if accessory cells carry the virus, the cells may contaminate the entire T cell population during long-term culture.

In the absence of exogenous growth factors or accessory cells, a co-stimulatory signal may be delivered to a T cell population, for example, by exposing the cells to a CD3 ligand and a CD28 ligand attached to a solid phase surface, such as a bead. See C. June, et al., (U.S. Pat. Nos. 5,858,358 and 6,352,694); C. June et al., WO 99/953823. The methods currently available in the art have not focused on obtaining a more robust population of T cells and the beneficial results thereof. Furthermore, the applicability of activated and expanded T cells has been limited to only a few disease states. For maximum in vivo effectiveness, theoretically, an ex vivo- or in vivo-generated, activated T cell population should be in a state that can maximally orchestrate an immune response to cancer, infectious disease, or other disease states. While previous investigators have noted long term qualitative persistence of T cells in human adoptive transfer protocols, the quantitative level of sustained engraftment has been low (Rosenberg et al., *N. Engl. J. Med.* 323:570-578 (1990); Dudley et al., *J. Immunother.* 24:363-373 (2001); Yee et al., Curr. *Opin. Immunol.* 13:141-146(2001); Rooney et al., *Blood* 92:1549-1555 (1998)).

Therefore, the present invention offers therapeutic advantages because there remains an unmet need for sustained high-level engraftment of human T lymphocytes. Methods of stimulating the expansion of certain subsets of T cells have the potential to generate a variety of T cell compositions useful in immunotherapy. Successful immunotherapy can be aided by increasing the reactivity and quantity of T cells by efficient stimulation. The present invention provides methods to generate an increased number of activated and pure T cells that have surface receptor and cytokine production characteristics that are optimal for T cell-mediated immune responses and that appear more physiologically functional than T cells produced by other expansion methods. In addition, the present invention provides compositions of cell populations of any target cell, including T cell populations and parameters for producing the same, as well as providing other related advantages.

BRIEF SUMMARY OF THE INVENTION

The present invention provides engineered multivalent signaling platforms (EMSP) for use in stimulation and/or expansion of T cells. Also provided are methods of using the EMSPs either to stimulate or expand T cells ex vivo or in vivo or a combination thereof, such as stimulating ex vivo and allowing for expansion in vivo. To this end, one of ordinary skill in the art would understand that a variety of combinations of the elements of the present invention is easily identifiable. For instance, T cells either stimulated and/or expanded can be used for therapeutic purposes. Moreover, it would be clear upon reference to the instant specification that EMSPs may also be administered to a patient in vivo thereby stimulating and/or expanding T cells in vivo. Such in vivo uses are numerous, including breaking tolerance to an antigen from a tumor or pathogen or as a means to enhance antigen reactivity of a vaccine thereby acting as an adjuvant.

In one aspect, the present invention is directed to stimulation, activation, or expansion of T cells, including but not limited to $CD4^+$ and $CD8^+$ T cells. Further, the present invention finds particular benefit in the ability to sequentially stimulate and expand $CD8^+$ cells without a significant loss in viability and maintaining function of the $CD8^+$ T cells after multiple rounds of stimulation with EMSPs.

In another aspect, the present invention provides an engineered multivalent signaling platform (EMSP) for use in stimulating and/or activating T cells comprising an EMSP that expresses or displays on its surface one or more agents that ligate a cell surface moiety of at least a portion of T cells and stimulates said T cells. In certain embodiments this platform may comprise a cell line. This cell line may be a mammalian cell line, including, but not limited to, human cell lines. In certain embodiments the cell line displays low or no endogenous MHC as compared with typical antigen presenting cells. An antigen presenting cell refers to those cells that normally initiate the responses of naïve and/or memory T cells to antigen. Illustrative APCs include, but are not limited to, dendritic cells (DC), macrophages, and B cells. In related embodiments, the human cell line may be K562, U937, 721.221, T2, and C1R cells.

In related aspects, the EMSPs of the present invention are cells that are genetically modified to express a human Fcγ receptor or manipulated to have this receptor bound to the surface of the EMSP. In certain embodiments the receptor comprises CD32. In an alternative embodiment, the EMSP are genetically modified to express a membrane bound ScFv, or fragment thereof, or other membrane-bound form of antibody, that is capable of capturing or otherwise binding secondary antibodies, or fragments thereof. Within this context, the EMSP becomes "armed" with these secondary antibodies, such as anti-CD3, anti-CD28, or anti-41BB antibodies. In other embodiments, the EMSP is a cell that is genetically modified to express CD32 and said one or more agent is an antibody that binds to a cell surface molecule on the surface of T cells. Also provided are the presently described EMSPs wherein the EMSP is further genetically modified to express or manipulated to display a co-stimulatory molecule for a T cell. In certain embodiments the co-stimulatory molecule may be any one of or a combination of CD80, CD86, 4-1BBL, OX40L, ICOS-L, ICAM, PD-L1 and PD-L2. Other embodiments include but are not limited to EMSPs wherein one or more agent on the surface is an antibody that is displayed on the surface of said EMSP via interaction with the Fcγ receptor. Other embodiments, of course include wherein the one or more agent displayed or expressed on the EMSP is a natural ligand for a T cell such as those to CD28 and 4-1BB.

In certain aspects the present invention also provides EMSPs in the form of cells or cell lines that have been genetically modified to express stimulatory agents, co-stimulatory agents, and/or cytokines as well as other polypeptides. When cytokines are expressed any of those desired by be utilized. For example, IL-2, IL-15, GM-CSF, IL-4, TNF-α, and/or IFN-γ be utilized among others.

In yet additional embodiments, the source of T cells to be stimulated, activated, and/or expanded by use of the EMSPs may be any type of T cell, including CD4+, CD8+, regulatory T cells and the like.

Also provided by the instant invention are EMSPs that display or express on their surface antibodies such as anti-CD3 and anti-CD28 antibodies as well as or alternatively, other ligands and stimulatory or co-stimulatory molecules such as 4-1BB ligand.

In other aspects the present invention provides methods for activating and/or stimulating a population of T cells by cell surface moiety ligation, comprising providing a population of cells wherein at least a portion thereof comprises T cells; contacting said population of cells with an EMSP, said EMSP having on its surface one or more agents that ligate a cell surface moiety of at least a portion of said T cells and activates or stimulates said T cells. In certain embodiments the EMSP comprises a cell. In related embodiments the cell may be a mammalian cell, the cell may be a human cell, the cell may be a murine cell, the cell may be from a cell line such as a human cell line. In further embodiments the T cells are expanded by culturing the cells following stimulation with EMSPs under conditions and for time sufficient to provide expansion. Such expansion may occur in the presence or absence of EMSPs as well as in the presence or absence of exogenously added cytokines. Further, such stimulation and/or expansion may occur in vivo. In related embodiments the method includes separating said T cells from said EMSP and subsequently incubating said T cells with an agent that facilitates T cell expansion. Those of skill in the art would appreciate that the T cells stimulated or expanded may be derived from any source including but not limited to a patient, from a T cell line, or from a T cell clone.

In yet additional aspects the present invention provides methods for maintaining or restoring T cell repertoire, such as the Vβ repertoire of select T cell populations to be expanded, by stimulating with the EMSPs of the invention for a time sufficient to induce activation and subsequently expanding said T cells. In certain embodiments the expansion occurs in the presence or absence of EMSPs.

In further related aspects, the EMSPs of the present invention may be used to maintain the viability of T cells during culture, even following multiple/sequential rounds of stimulation. In certain embodiments sequential rounds of stimulation may be initiated by EMSPs. In certain aspects, even following sequential stimulation of T cells, such as without limitation CD8+ T cells, the viability of said T cells is greater than 50%, 60%, 70%, 80%, or 90% following at least one, two, three, four, five, six, seven, or eight rounds of stimulation.

In certain aspects of the present invention, EMSP may be used for activating and/or stimulating a population of T cells as described herein in conjunction with other surfaces, such as but not limited to, beads. In one embodiment, EMSP may be used to activate and/or stimulate a population of T cells for one or more rounds of stimulation, followed by one or more rounds of stimulation using paramagnetic beads such as described in U.S. patent application Ser. No. 10/350,305. In a further embodiment, EMSP may be used to activate and/or stimulate a population of T cells following activation and/or stimulation using beads such as those described in U.S. patent application Ser. No. 10/350,305.

In certain embodiments, CD8+ T cells re-stimulated with the EMSP of the present invention have reduced levels of apoptosis as compared to stimulation using other methods. Thus, the present invention also provides methods for enchancing survival of a population of CD8+ T cells, comprising stimulating said cells at least once with EMSP, said EMSP having on its surface at least one primary stimulatory agent and at least one co-stimulatory agent. In certain embodiments, the CD8+ T cells are expanded in the presence or absence of said EMSP. In further embodiments, the CD8+ T cells demonstrate an increase in Bcl-$X_L$ levels compared to CD8+ T cells expanded in the absence of initial stimulation with said EMSP. In certain embodiments, the increase is from about 1.5 fold to about 10 fold and higher. In certain embodiments, the increase is about 15, 20, 30, 40, or 50 fold in expression. In one embodiment, the increase in Bcl-$X_L$ expression is from about 2, 2.5, 3, 3.5, 4, 4.5, 5, 5.5, 6, 6.5, 7, 7.5, 8, 8.5, 9, 9.5 fold or higher. In yet additional embodiments the EMSP expresses or displays a 4-1BB ligand. In other embodiments the EMSP displays or expresses an agent that binds to CD3 or other components of the TCR/CD3 complex, and an agent that binds to CD28 or an agent that binds 4-1BB or any combination or multiple thereof. In related embodiments sequential stimulation with the EMSP also demonstrates decrease in apoptosis as compared to cells sequentially stimulated by other means such as by anti-CD3 and anti-CD28 coated beads. A decrease generally means a decrease in apoptosis in cells stimulated with the EMSP of the present invention as compared to cells stimulated by other means, as measured using any number of assays known in the art and described herein. In certain embodiments, the decrease is from about 1.5 fold to about 10 fold and lower. In certain embodiments, the decrease is about 15, 20, 30, 40, or 50 fold lower apoptosis observed. In one embodiment, the decrease in apoptosis is about 2, 2.5, 3, 3.5, 4, 4.5, 5, 5.5, 6, 6.5, 7, 7.5, 8, 8.5, 9, 9.5 fold lower in cells stimulated with the EMSP of the present invention.

Apoptosis is a basic physiological process that plays a major role in the regulation of cell populations. Methods for measuring apoptosis are well known in the art. Apoptosis can be determined by methods such as, for example, DNA ladder, electron or light microscopy, flow cytometry, and different commercially available kits for the determination of apoptosis. Within the context of this invention, decreases or increases in apoptosis can be measured using any number of assays known to the skilled artisan. Illustrative assays include but are not limited to, measuring gene expression levels of Bcl-xL or other apoptosis genes, and fluorescent staining with Annexin V and propidium iodide.

In further aspects the present invention also provides methods for expanding a population of T cells by cell surface moiety ligation, comprising providing a population of cells wherein at least a portion thereof comprises T cells either in vivo or ex vivo; contacting said population of cells with an EMSP, said EMSP having on its surface one or more agents that ligate a cell surface moiety of at least a portion of said T cells and activates and/or stimulates said T cells; and culturing said T cells under conditions and time sufficient to induce cell division, wherein said contacting and/or said culturing can occur in the absence or the presence of exogenously added cytokines. In yet additional embodiments the EMSP comprises a cell, such as a mammalian cell (e.g., human, murine, etc.). The cell may be from a cell line. In some embodiments, at least one round of stimulation is provided. In related embodiments sequential rounds of stimulating said T cells are performed with EMSP either by previously purifying T cells from originally added EMSP and subsequently adding additional EMSP or by adding additional EMSP to previously stimulated cells without separation of originally added EMSP. In other embodiments, the T cells are separated from said EMSP and subsequently incubated with an agent that facilitates T cell expansion, followed by restimulation with EMSP. Of course the T cells for these methods could be derived from any source including PBMC, purified T cells, T cell lines, T cell clones, etc. In certain embodiments the EMSP comprises a cell displaying ligands for any one of CD3 and/or TCR complex (such as peptide-MHC complexes), CD28, or 4-1BB including any combination thereof, such as ligands to all three.

In other aspects, the present invention provides methods for expanding a population of T cells by cell surface moiety ligation, comprising providing a population of cells wherein at least a portion thereof comprises T cells either ex vivo or in vivo; contacting said population of cells with an EMSP, said EMSP having on its surface one or more agents that ligate a cell surface moiety of at least a portion of said T cells and activates and/or stimulates said T cells; and culturing said T cells under conditions and time sufficient to induce cell division. As with all the described methods herein in related embodiments the EMSP may comprise a cell such as a mammalian cell (e.g., human or murine cell or the like), a cell line or cell fusion or cell hybrid. In additional embodiments, the method further comprises sequentially stimulating said T cells with EMSP either by previously purifying T cells from originally added EMSP and subsequently adding additional EMSP or by adding additional EMSP to previously stimulated cells without separation of originally added EMSP. In a related embodiment, the methods comprise separating said T cells from said EMSP and subsequently incubating said T cells with an agent that facilitates T cell expansion, followed by restimulation with EMSP. In certain embodiments the EMSP comprises a cell displaying ligands for any one of CD3, CD28, or 4-1BB including any combination thereof, such as ligands to all three. In yet additional embodiments, following initial stimulation or activation said T cells are separated from EMSP and then expanded in the presence of exogenously added cytokines. In yet still an additional embodiment the methods of the present invention include the previous method may include T-cells that are initially stimulated by EMSPs but that are substantially free of EMSP prior to expansion.

One aspect of the present invention provides a population of T cells expanded by the methods of the present invention either in the absence or presence of exogenous cytokines and wherein said T cells are substantially free of EMSP.

An additional aspect of the present invention provide for a method of immunotherapy comprising administering an EMSP to a subject in need thereof, thereby stimulating a population of T cells within the subject to expand.

A further aspect of the present invention comprises a method of enhancing reactivity to an antigen comprising administering an EMSP to a subject in need thereof concurrently, prior to or following inoculation of the subject with an antigen of interest, thereby stimulating a population of antigen specific T cells within the subject to expand.

Yet a further aspect of the present invention comprises a method for breaking immune tolerance comprising administering an EMSP to a subject either systemically or locally at a site of interest.

One additional aspect of the invention comprises a method for increasing uptake of an exogenously added nucleic acid molecule in T cells, comprising contacting said T cells with an EMSP and contacting said T cells with said nucleic acid molecule thereby, said contacting of EMSP with said T cells rendering cells more amenable to uptake of nucleic acid. In one embodiment of the invention, exogenously added nucleic acids are operably linked to a promoter. In certain embodiments, nucleic acid molecules provided herein provide gene replacement for abnormal gene products.

In certain aspects of the present invention, the natural functionality of said T cells is preserved following stimulation and expansion using the methods provided herein.

In another aspect of the invention, a method of activating antigen specific T cells is provided comprising contacting a population of T cells with an antigen and an EMSP under conditions and for time sufficient to induce activation of T cells specific to said antigen. In certain embodiments, a population of T cells is first contacted with antigen, and then contacted with EMSP. In one particular embodiment, the antigen-specific T cells are induced by vaccination of a patient with a particular antigen, either alone or in conjunction with an adjuvant or pulsed on dendritic cells. Antigen-specific cells for use in expansion using the EMSP of the present invention may also be generated in vitro using any number of methods known in the art, for example, as described in U.S. Patent Application No. 60/469,122 entitled, GENERATION AND ISOLATION OF ANTIGEN-SPECIFIC T CELLS, filed May 8, 2003, or in U.S. Pat. Nos. 6,040,177 and 5,872,642. Antigen-specific cells for use in expansion using the EMSP of the present invention may also be generated using any number of methods known in the art, for example, as described in Current Protocols in Immunology, or Current Protocols in Cell Biology, both published by John Wiley & Sons, Inc., Boston, Mass.

In certain embodiments, activation of antigen-specific T cells occurs ex vivo after which the T cells are administered to a patient substantially free or in combination with said EMSP. In one embodiment, the antigen is displayed by said EMSP. In a particular embodiment, the antigen is displayed by way of a fusion protein. In one embodiment the antigen is displayed through antibody binding (e.g. an antigen-specific antibody expressed by or otherwise on the surface of the EMSP). In another embodiment, the antigen is in the form of a complex with an MHC molecule or MHC derived peptide such as in an peptide-MHC tetramer, dimer, or monomer.

Another aspect of the present invention provides a method for expanding antigen specific T cells, comprising contacting a population of T cells with an antigen for a time sufficient to induce activation of T cells specific to said antigen; contacting said population of antigen-specific T cells ex vivo with an EMSP under conditions and for time sufficient to induce proliferation of T cells specific to said antigen, thereby expanding antigen-specific T cells. In one embodiment, the antigen is a tumor antigen. In one particular embodiment, the tumor antigen is hTERT. In another embodiment, the antigen is pulsed on or expressed by an antigen-presenting cell. In a further embodiment the population of T cells is contacted with said antigen in vivo. In yet another embodiment, the population of T cells is contacted with said antigen ex vivo. In another embodiment, the method comprises at least one round of peptide-MHC tetramer sorting of said antigen-specific T cells. In certain embodiments, the method of the present invention further comprises at least one round of peptide-MHC tetramer magnetic selection of said antigen-specific T cells.

Another aspect of the present invention provides a method for the treatment of cancer comprising administering to a cancer patient antigen-specific T cells expanded according to the methods provided herein. In certain embodiments, the patient is afflicted with breast cancer.

BRIEF DESCRIPTION OF THE SEVERAL VIEWS OF THE DRAWINGS

The foregoing summary, as well as the following detailed description of the invention, will be better understood when read in conjunction with the appended drawings. It should be understood, however, that the invention is not limited to the precise arrangements and instrumentalities shown.

FIG. 1A depicts two-color flow-cytometric analysis of MHC I and II expression and CD54 and CD58 expression in parental K562 cells (top panels). Expression of CD32 and 4-1BBL in K32 (left) and K32/4-1BBL (right) cell lines is shown (middle panels). Isotype controls for the anti-CD32 antibody (IgG2a) and anti-41BBL antibody (IgG1) are shown for each aAPC (bottom panels). FIG. 1B depicts the engineered K32/4-1BBL aAPC interacting with a CD8+ T cell. FIG. 1C graphically depicts proliferation of polyclonal CD4+ and CD8+ T cells stimulated with the indicated aAPCs, measured by [3H]thymidine incorporation between days 3 and 4 culture. T cells were stimulated with aAPCs as indicated, in the absence of cytokines. At 72 hours the cells were pulsed with [3H]thymidine and incubated for an additional 18 hours before harvesting. Counts per minute values are shown as mean±s.e.m. from triplicate cultures.

FIG. 2A graphically depicts CD8+ T cells stimulated with CD3/28 beads (X), irradiated K32 cells loaded with CD3/28 antibodies (Δ), or with irradiated K32/4-1BBL cells loaded with CD3/28 antibodies (●). T cells were stimulated with aAPCs on days 0, 10, and 20 of culture. FIGS. 2B, 2C depict the purity of T cells and the fate of irradiated K32/4-1BBL stimulator cells assessed by staining for CD3, CD8 (FIG. 2B), and CD32 (FIG. 2C) expression during the first 7 days of culture. Variable numbers of red blood cells and platelets were contained in the input cultures; gating on cell size/debris was not used in this experiment so that all cells in the culture were represented. Viable cells are indicated by gating on propidium iodide to exclude dead cells. Results are representative of >10 different experiments, each with a different donor.

FIG. 3A is a schematic of the experimental protocol of the present invention. FIG. 3B depicts the specificity of cell cultures as assessed by MHC tetramer staining. CD8+ T cells were stained with anti-CD8 antibody (x-axis) and A*0201 tetrameric MHC (y-axis) loaded/folded with influenza matrix protein peptide (fluMP). Left panel of 3B: initial cell population of T cells on day 0, with gates showing the cells into CD8+flu-tet+ and CD8+flu-tet− populations. Right panels of 3A: tetramer staining of CD8+flu-tet+ (top) or CD8+flu-tet− (bottom) cultures after expansion on K32/4-1BBL cells for 26 days. FIG. 3C graphically depicts a growth curve of the sorted CD8+ T cell populations. T cells were sorted into CD8+ fluMP tetramer+ (●) or CD8+ fluMP tetramer− (□). The sorted T cell populations were then stimulated with irradiated K32/4-1BBL cells loaded with CD3/28 antibodies as indicated (arrows). rIL-2 was added to the cultures beginning on day 28. The total cell numbers are depicted in a semi-log plot of cell number v. days in culture. FIG. 3D graphically depicts cytotoxicity of flu-specific T cells after expansion on K32/4-1BBL aAPCs for 26 days. $^{51}$Cr-release assays were done using TAP-deficient HLA A*0201 T2 target cells pulsed (circles) or unpulsed (squares) with the fluMP peptide. Antigen-specific cytotoxicity was also examined by comparing CD8+ fluMP tetramer+ cells (closed symbols) to CD8+FluMP tetramer− cells (open symbols). Values shown as mean±s.e.m. of triplicate cultures. Y-axis, percentage of specific 51Cr release; x-axis, effector:target (E:T) ratios. The entire protocol is representative of three experiments, each from different donors.

DETAILED DESCRIPTION OF THE INVENTION

Figure 1A:
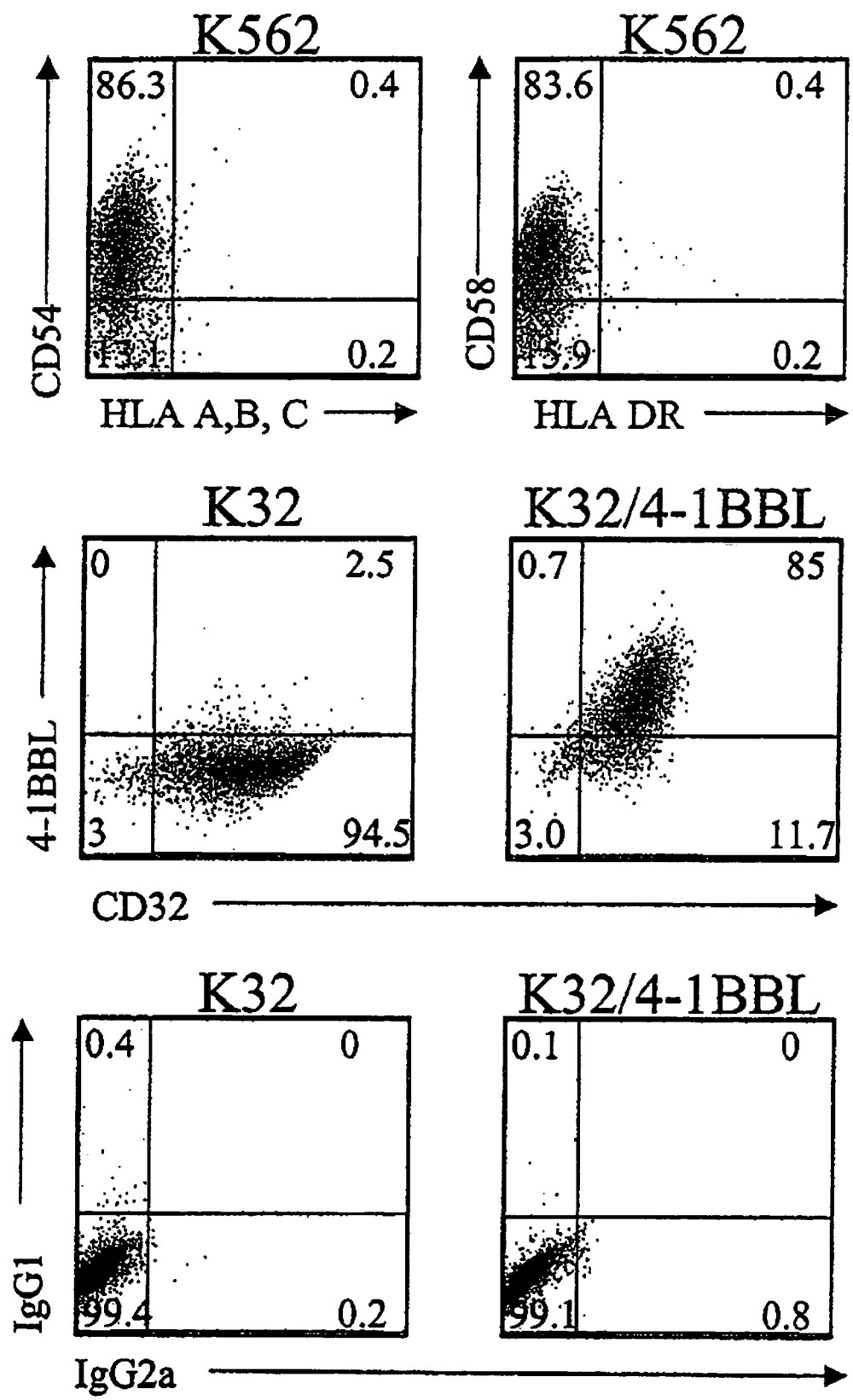
FIGS. 1A-1C depict construction of artificial APCs (aAPC) (an illustrative example of an engineered multivalent signaling platform, or EMSP) from the parental K562 cell line.
Figure 1B:
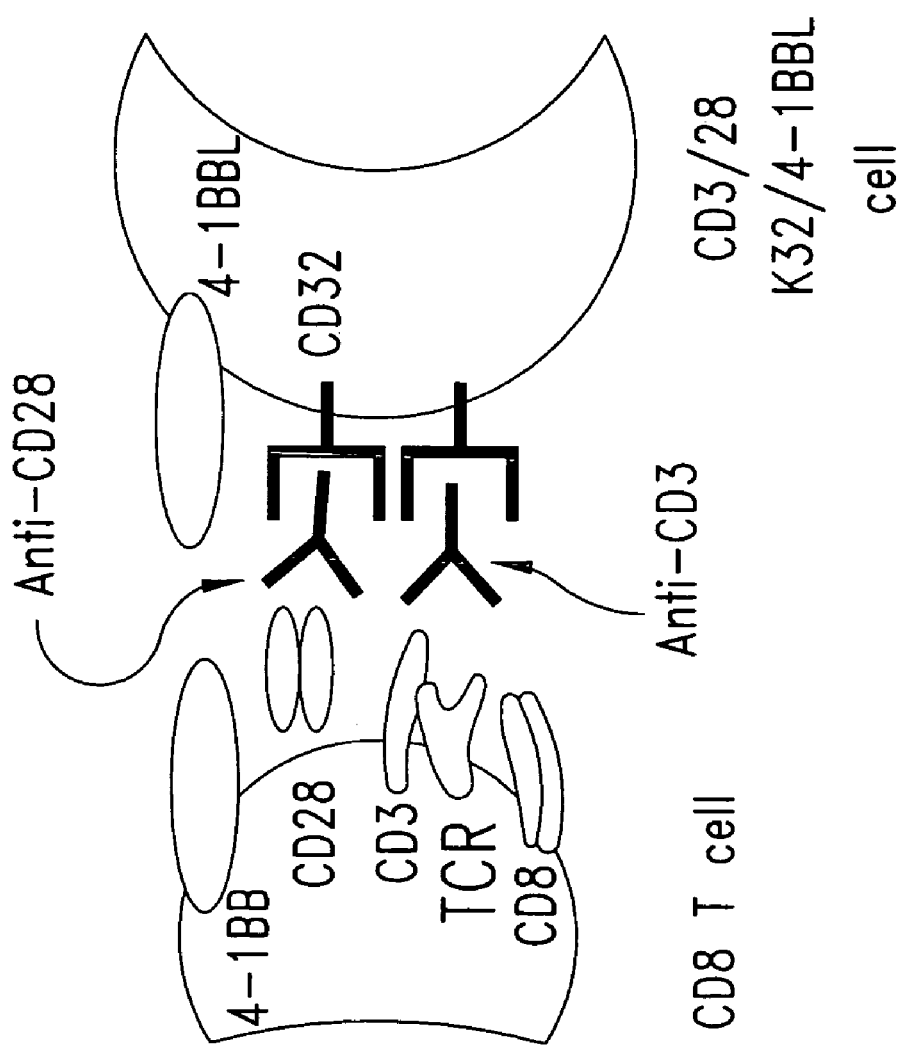

Prior to setting forth the invention, it may be helpful to an understanding thereof to set forth definitions of certain terms that will be used hereinafter.

The term "biocompatible", as used herein, refers to the property of being predominantly non-toxic to living cells.

The term "stimulation", as used herein, refers to a primary response induced by ligation of a cell surface moiety. For example, in the context of receptors, such stimulation entails the ligation of a receptor and a subsequent signal transduction event. With respect to stimulation of a T cell, such stimulation refers to the ligation of a T cell surface moiety that in one embodiment subsequently induces a signal transduction event, such as binding the TCR/CD3 complex. Further, the stimulation event may activate a cell and upregulate or downregulate expression or secretion of a molecule, such as downregulation of TGF-β. Thus, ligation of cell surface moieties, even in the absence of a direct signal transduction event, may result in the reorganization of cytoskeletal structures, or in the coalescing of cell surface moieties, each of which could serve to enhance, modify, or alter subsequent cellular responses.

A stimulation cycle or round of stimulation generally refers to stimulation as described herein and the period of culture following stimulation without any additional stimulation (e.g., restimulation). A stimulation cycle or round of stimulation is generally from about 7-14 days. In certain embodiments, the stimulation cycle can be shorter, for example 2, 3, 4, 5, or 6, days. In certain embodiments, the stimulation cycle can be much longer, such as from 15-20, or from 20-30 or more days. In certain embodiments, it may be desirable for the T cells to enter a quiescent, non-dividing phase of the cell cycle. Therefore, in certain embodiments of the present invention, cells may remain in culture without restimtilation for periods much longer than 10 days, such as for 11, 12, 13, 14, 15, 16, 17, 18, 19, 20, 21, 22, 23, 24, 25, 26, 27, 28, 29, 30, 31, 32, 33, 34, 35, 36, 37, 38, 39, and even 40 days in vitro. As described in U.S. Pat. No. 6,040,177, T cells were observed to assume a small round morphology and 60-95% of the cells remained viable (as determined by trypan blue dye exclusion) even after 28 days in culture.

The term "activation", as used herein, refers to the state of a cell following sufficient cell surface moiety ligation to induce a noticeable biochemical or morphological change. Within the context of T cells, such activation refers to the state of a T cell that has been sufficiently stimulated to induce cellular proliferation. Activation of a T cell may also induce cytokine production and performance of regulatory or cytolytic effector functions. Within the context of other cells, this term infers either up or down regulation of a particular physico-chemical process The term "activated T cells" indicates T cells that are currently undergoing cell division, cytokine production, performance of regulatory or cytolytic effector functions, and/or has recently undergone the process of "activation."

The term "target cell", as used herein, refers to any cell that is intended to be stimulated by cell surface moiety ligation.

An "antibody", as used herein, includes both polyclonal and monoclonal antibodies; primatized (i.e., modified to include more primate-specific residues in a constant region) (e.g., humanized); murine; mouse-human; mouse-primate; and chimeric; and may be an intact molecule, a fragment thereof (such as scFv, Fv, Fd, Fab, Fab' and F(ab)'$_2$ fragments), or multimers or aggregates of intact molecules and/or fragments; and may occur in nature or be produced, e.g., by immunization, synthesis or genetic engineering; an "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'$_2$, scFv, light chain variable region ($V_L$), heavy chain variable region ($V_H$), and combinations thereof.

The term "protein", as used herein, includes proteins, polypeptides and peptides; and may be an intact molecule, a fragment thereof, or multimers or aggregates of intact molecules and/or fragments; and may occur in nature or be produced, e.g., by synthesis (including chemical and/or enzymatic) or genetic engineering.

The term "T cell clone" as used herein includes T cells derived from a single T cell or those having identical TCRs. T cells can be cloned using numerous methods known in the art including limiting dilution assays (LDA) and cell sorting using flow cytometry.

The term "T cell line" as used herein includes T cell clones and mixed populations of T cells with different TCRs all of which may recognize the same target (e.g., antigen, tumor, virus).

The term "substantially free of" as used herein means a population of cells, e.g., T cells, that is at least 50% free of non-T cells, or in certain embodiments at least 60, 70, 80, 85, or 90% free of non-T cells.

The term "agent", "ligand", or "agent that binds a cell surface moiety", as used herein, refers to a molecule that binds to a defined population of cells. The agent may bind any cell surface moiety, such as a receptor, an antigenic determinant, or other binding site present on the target cell population. The agent may be a protein, peptide, antibody and antibody fragments thereof, fusion proteins, synthetic molecule, an organic molecule (e.g., a small molecule), a carbohydrate, or the like. Within the specification and in the context of T cell stimulation, antibodies and natural ligands (e.g., B7 and 4-1BBL) are used as prototypical examples of such agents.

The terms "agent that binds a cell surface moiety" and "cell surface moiety", as used herein, are used in the context of a ligand/anti-ligand pair. Accordingly, these molecules should be viewed as a complementary/anti-complementary set of molecules that demonstrate specific binding, generally of relatively high affinity (an affinity constant, $K_a$, of about $10^6$ $M^{-1}$).

A "co-stimulatory signal", as used herein, refers to a signal, which in combination with a primary signal, such as TCR/CD3 ligation, leads to T cell proliferation and/or upregulation or downregulation of key molecules.

A "ligand/anti-ligand pair", as used herein, refers to a complementary/anti-complementary set of molecules that demonstrate specific binding, generally of relatively high affinity (an affinity constant, $K_a$, of about $10^6$ $M^{-1}$,). Exemplary ligand/anti-ligand pairs enzyme/inhibitor, hapten/antibody, lectin/carbohydrate, ligand/receptor, and biotin/avidin or streptavidin. Within the context of the present invention specification receptors and other cell surface moieties are anti-ligands, while agents (e.g., antibodies and antibody fragments) reactive therewith are considered ligands.

"Separation", as used herein, includes any means of substantially purifying one component from another (e.g., by filtration or magnetic attraction).

"Quiescent", as used herein, refers to a cell state wherein the cell is not actively proliferating.

A "surface", as used herein, refers to any surface capable of having an agent attached thereto and includes, without limitation, metals, glass, plastics, co-polymers, colloids, lipids, lipid bilayers, cell surfaces such as EMSP as described herein, and the like. Essentially any surface that is capable of retaining an agent bound or attached thereto. A prototypical example of a surface used herein, is an engineered multivalent signaling platform or a particle such as a bead.

"Antigen" as used herein, refers to any molecule 1) capable of being specifically recognized, either in its entirety or fragments thereof, and bound by the "idiotypic" portion (antigen-binding region) of a mAb or its derviative; 2) containing peptide sequences which can be bound by MHC molecules and then, in the context of MHC presentation, can specifically engage its cognate T cell antigen receptor. As such, according to the present invention, the source of antigen may be, but is not limited to, protein, including glycoprotein, peptides, superantigens (e.g., SEA, SEB, TSST-1) antibody/antigen complexes, tumor lysate, non-soluble cell debris, apoptotic bodies, necrotic cells, whole tumor cells from a tumor or a cell line that have been treated such that they are unable to continue dividing, allogeneic cells that have been treated such that they are unable to continue dividing, irradiated tumor cells, irradiated allogeneic cells, natural or synthetic complex carbohydrates, lipoproteins, LPS, RNA or a translation product of said RNA, and DNA or a polypeptide encoded by said DNA. Non-transformed cells are typically irradiated with gamma rays in the range of about 3000 to 3600 rads, more preferably at about 3300 rads. Lymphoblastoid or tumor cell lines are typically irradiated with gamma rays in the range of about 6000 to 10,000 rads, more preferably at about 8000 rads. Necrotic and apoptotic cells may be generated by physical, chemical, or biological means. Necrotic cells are typically generated by freeze-thawing, while apoptotic cells are generated using UV irradiation. UV and gamma irradiation, and freeze-thawing procedures are well known in the art and are described, for example, in *Current Protocols in Molecular Biology or Current Protocols in Immunology*, John Wiley & Sons, New York, N.Y.

Generation of Engineered Multivalent Signaling Platforms (EMSP)

One aspect of the present invention is directed to the finding that a cell-based universal engineered multivalent signaling platform (EMSP) specifically optimized for rapid expansion of human T cells can be used to stimulate the long-term growth of functional polyclonal and antigen-specific human T lymphocytes. In particular, in one aspect of the present invention, the EMSP can be generated that stimulate the long-term growth of CD8+ T cells. In another aspect of the present invention, the EMSP can be generated that stimulate the long-term growth of CD4+ T cells. In a further embodiment, the EMSP can be generated to stimulate the long-term growth of regulatory T cells. Similarly, the EMSP of the present invention can be used for stimulation of growth of combinations of T cell subsets (e.g., γδ-T cells, CD4+ and CD8+ ag-spec T cells). In yet another embodiment, an EMSP can be generated to stimulate CD4/CD8 double positive T cells, or CD28-negative T cells. One illustrative embodiment of an EMSP is referred to as an artificial antigen presenting cell (aAPC) and is described herein in the Examples.

An "engineered multivalent signaling platform (EMSP)", as used herein, refers to a lipid bilayer engineered (e.g., genetically, physically, or chemically manipulated) to have on its surface at least one molecule capable of binding to a T-lymphocyte and inducing a primary activation event and/or a proliferative response or capable of binding a molecule having such an affect thereby acting as a scaffold. In one embodiment, the EMSP is engineered to express a molecule that binds to the Fc portion of an antibody. In an additional embodiment, an EMSP comprises a cell line engineered to stably express a molecule capable of binding to the Fc portion of an antibody. This universal EMSP can then be loaded or otherwise coated with or have attached thereto any variety of antibodies that recognize cell surface molecules present on the surface of T lymphocytes, e.g., CD3, or a component of the TCR/CD3 complex, CD28, 4-1BB, TCR, etc. In an alternative embodiment, an EMSP can be generated by directly engineering a cell line to stably express the ligands for cell surface molecules present on the surface of T lymphocytes, e.g. CD3, or a component of the TCR/CD3 complex, CD28, 4-1BB, TCR, etc. The EMSP can be further engineered to stably express one or more co-stimulatory molecules, for example CD86 or 4-1BB ligand. For example, in one illustrative embodiment of the present invention, an EMSP is engineered to express the human low-affinity Fcγ receptor, CD32 and the CD86 molecule. In another illustrative embodiment of the present invention an EMSP is engineered to express CD32 and the 4-1BB ligand. In one embodiment, the EMSP of the present invention can be generated that express membrane bound ScFv or a fragment thereof, that recognize any cell surface molecule of interest, such as CD3, CD28, 41BB and the like, or that recognize other antibodies, such as through binding to the Fc portion. In this regard, the EMSP can be armed with secondary antibodies that bind through recognition of the Fc portion. The skilled artisan would readily recognize that any variety and combination of stimulatory and/or co-stimulatory molecules can be used in the context of the present invention. Further, an EMSP may be engineered to express a variety of molecules useful for the stimulation and activation of T lymphocytes and/or be loaded or otherwise coated with or otherwise have attached thereto a variety molecules useful for the stimulation and activation of T lymphocytes. In some instances, the expression of these ligands/receptors could be regulated by "regulatable transcription promoters", such a tetracycline dependent promoter, which could be an advantage in certain in vivo applications of the K32 line (see Examples) and its derivatives.

In a further embodiment, the EMSP of the present invention are engineered to express an antigen of interest, such as a tumor antigen (e.g., a melanoma, breast tumor, leukemia or other tumor antigen), an auto-antigen (e.g., MBP), a viral antigen (e.g., an HIV, CMV, EBV, or Hepatitis antigen) or antigen of other pathogens of interest, presented on the EMSP surface in the context of MHC. Alternatively, the EMSP of the present invention can be pulsed with antigen using any number of assays known to the skilled artisan, or transduced or otherwise express MHC which can then be pulsed with peptide/antigen. In yet another embodiment, an EMSP of the present invention can be engineered to express peptide-MHC tetramers (Altman, et al., *Science.* 1996 Oct. 4; 274(5284): 94-6.), or monomers or dimers or trimers. Other illustrative molecules and methods useful in the context of this invention are as described in U.S. Pat. Nos. 6,001,365, 6,355,479, 5,529,921, and 6,464,973, herein incorporated by reference in their entirety.

According to certain methods of the invention, antigen may comprise defined tumor antigens such as, but not limited to, the melanoma antigen Melan-A (also referred to as melanoma antigen recognized by T cells or MART-1), melanoma antigen-encoding genes 1, 2, and 3 (MAGE-1, -2, -3), melanoma GP100, carcinoembryonic antigen (CEA), the breast cancer angtigen, Her-2/Neu, telomerase reverse transcriptase (hTERT), serum prostate specific antigen (PSA), Wilm's Tumor (WT-1), mucin antigens, MUC-1, -2, -3, -4, and B cell lymphoma idiotypes.

Antigen source may also comprise non-transformed, transformed, transfected, or transduced cells or cell lines. Cells may be transformed, transfected, or transduced using any of a variety of expression or retroviral vectors known to those of ordinary skill in the art that may be employed to express recombinant antigens. Expression may also be achieved in any appropriate host cell that has been transformed, transfected, or transduced with an expression or retroviral vector containing a DNA molecule encoding recombinant antigen(s). Any number of transfection, transformation, and transduction protocols known to those in the art may be used, for example those outlined in *Current Protocols in Molecular Biology*, John Wiley & Sons, New York, N.Y., or in numerous kits available commercially (e.g., Invitrogen Life Technologies, Carlsbad, Calif.). In one embodiment of the present invention, recombinant vaccinia vectors and cells infected with said vaccinia vectors, may be used as a source of antigen. Recombinant antigen may include any number of defined tumor antigens described below.

The EMSP of the present invention may be loaded or otherwise coated with or have attached thereto antigen or may be engineered to express a variety of stimulatory, co-stimulatory molecules, targeting agents, and/or cytokines through genetic modification. Genetic modification may comprise RNA or DNA transfection using any number of techniques known in the art, for example electroporation (using e.g., the Gene Pulser II, BioRad, Richmond, Calif.), various cationic lipids, (LIPOFECTAMINE™, Life Technologies, Carlsbad, Calif.), or other techniques such as calcium phosphate transfection as described in *Current Protocols in Molecular Biology*, John Wiley & Sons, New York, N.Y. For example, 5-50 µg of RNA or DNA in 500 µl of Opti-MEM can be mixed with a cationic lipid at a concentration of 10 to 100 µg, and incubated at room temperature for 20 to 30 minutes. Other suitable lipids include LIPOFECTIN™, LIPOFECTAMINE™. The resulting nucleic acid-lipid complex is then added to 1-3×10$^6$ cells, preferably 2×10$^6$, EMSP in a total volume of approximately 2 ml (e.g., in Opti-MEM), and incubated at 37° C. for 2 to 4 hours. The EMSP may also be transduced using viral transduction methodologies as described below.

The EMSP may alternatively be genetically engineered to express a variety of stimulatory molecules, co-stimulatory molecules, cytokines, and/or antigens using retroviral transduction technologies. In one aspect of the invention, the retroviral vector may be an amphotropic retroviral vector, preferably a vector characterized in that it has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. Retroviruses adaptable for use in accordance with the present invention can, however, be derived from any avian or mammalian cell source. These retroviruses are preferably amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman, *BioTechniques* 7:980-90, 1989; Miller, A. D., *Human Gene Therapy* 1:5-14, 1990; Scarpa et al., *Virology* 180:849-52, 1991; Burns et al., *Proc. Natl. Acad. Sci. USA* 90:8033-37, 1993; and Boris-Lawrie and Temin, *Cur. Opin. Genet. Develop.* 3:102-09, 1993.

The cell line used to generate EMSP can be derived from any mammal. Particularly illustrative cell lines can be derived from human, mouse, monkey, rabbit, or pig cells. In one particular embodiment, the cell line used as a scaffold for the EMSP is a human cell line. Generally, cell lines used to generate an EMSP of the present invention for the generation of polyclonal T cells, expresses low or no MHC class I or class II molecules, although, cloned T cells, or T cells with known specificity may not require low MHC on the EMSP, as they will tend not to be allo-responsive, and simply need to be amplified in number. In one particular embodiment, the K562 human erythromyeloid cell line is used (American Type Culture Collection, Manassas, Va.). In a further embodiment, the 721.221 cell line is used as a scaffold for generating an EMSP (R. Greenwood, et al., 1994. *J. Immunol.* 153:5525; Shimizu, Y., and R. DeMars. 1989. *J. Immunol.* 142:3320). In another embodiment, the T2 cell line is used as a scaffold for generating an EMSP (Salter, R. D., et al., 1985. *J. Immunol.* 135: 4235; III Grandea, A. G., et al., 1995. *Science* 270:105). In yet a further embodiment, the C1R cell line is used as a scaffold for generating an EMSP (Edwards, P. A., et al., 1982. *Eru J. Immunol.* 12:641). Generally, cell lines used to generate an EMSP of the present invention for the generation of antigen-specific T cells, can express MHC molecules.

In one aspect of the present invention, lipid bilayers can be used as a scaffold for generating EMSP. Illustrative lipid bilayers are as described for example in Copeland, B., and McConnel, H. M. (1980) *Biochim. Biophys. Acta* 599, 95-109; McMullen, T. P. W., et al., (1994) *Biophys. J.* 66, 741-752; Almeida, P. F. F., et al, 1992 *Biochemistry* 31, 7198-7210; Tilcock, C. P. S., et al., 1984, *Biochemistry* 23, 2696-2703; Simons, K and Ikonen, E. 1997 *Nature* 387, 569-572; Siminovitch, D. J. et al., 1987, *Biochim. Biophys. Acta* 901, 191-200.

As discussed above, the EMSP may be engineered to express a variety of stimulatory molecules, co-stimulatory molecules, cytokines, and/or antigen. The language "nucleic acid molecule encoding such molecules" is intended to include any nucleic acid molecule that will be transcribed and translated into a protein in accordance with the present invention upon introduction of the nucleic acid molecule into an EMSP (e.g., the molecule can further contain appropriate control elements for regulating expression in the EMSP). The nucleic acid molecule encoding the stimulatory, co-stimulatory and/or antigen molecules can consist of only the coding region of the corresponding gene, or alternatively it can contain noncoding regions, such as 5' or 3' untranslated regions, introns, fragments thereof, or other sequences.

The nucleic acid molecule can encode the full length marker or co-stimulatory protein or alternatively the nucleic acid can encode a peptidic fragment thereof that is sufficient to confer enhanced cell proliferation in accordance with the present invention, when contacted with a target cell such as a T cell. The nucleic acid can encode the natural marker or co-stimulatory protein or fragment thereof, or a modified form of the marker or co-stimulatory protein or fragment thereof. Modified forms of the natural marker or co-stimulatory protein that are within the scope of the invention are described below.

The invention is intended to include the use of fragments, mutants, or variants (e.g., modified forms) of the marker, stimulatory, co-stimulatory molecule, or antigen protein that retain the ability to induce stimulation and proliferation of T cells. A "form of the protein" is intended to mean a protein that shares a significant homology with the natural marker, stimulatory molecule, co-stimulatory protein or antigen and is capable of effecting stimulation and proliferation of T cells. The terms "biologically active" or "biologically active form of the protein," as used herein, are meant to include forms of marker, stimulatory molecules, or co-stimulatory proteins that are capable of effecting enhanced activated T cell proliferation. One skilled in the art can select such forms of markers, stimulatory molecules, or co-stimulatory proteins based on their ability to enhance T cell proliferation upon introduction of a nucleic acid encoding said proteins into an EMSP. The ability of a specific form of marker, stimulatory protein, co-stimulatory protein or antigen to enhance T cell proliferation can be readily determined, for example, by measuring cell proliferation or effector function by any known assay or method, including many disclosed herein.

The nucleic acid can be a cDNA or alternatively it can be a genomic DNA fragment. Variants of the proteins described herein can be prepared b a variety of known methods, such as, for example, by introducing nucleotide base pair modifications (e.g., substitutions, deletions, additions) to a nucleic acid molecule encoding a protein useful in the instant invention by standard methods, such as site-directed mutagenesis or polymerase chain reaction-mediated (PCR) mutagenesis.

Furthermore, it will be appreciated by those skilled in the art that changes in the primary amino acid sequence of a protein useful in the present invention are likely to be tolerated without significantly impairing the ability of the protein to enhance T cell proliferation. Accordingly, mutant forms of the proteins that have amino acid substitutions, deletions and/or additions as compared to the naturally occurring amino acid sequence of a comparable native protein molecule, yet still retain the functional activity of the natural form of the protein as described herein are also encompassed by the invention. To retain the functional properties, preferably conservative amino acid substitutions are made at one or more amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

To express a nucleic acid molecule encoding a desired protein, such as CD32, 4-1BBL, CD86 or other stimulatory or co-stimulatory molecules in an EMSP, the nucleic acid must be operably linked to regulatory elements. "Operably linked" is intended to mean that the nucleotide sequence encoding the protein of interest is linked to at least one regulatory sequence in a manner that allows expression of the nucleotide sequence in the EMSP. Regulatory sequences are selected to direct expression of the desired protein in an appropriate EMSP. Accordingly, the term "regulatory sequence" includes promoters, enhancers and other expression control elements. Such regulatory sequences are known to those skilled in the art and are further described in Goeddel, *Gene Expression Technology: Methods in Enzymology* 185, Academic Press, San Diego, Calif. (1990).

These regulatory elements include those required for transcription and translation of the nucleic acid encoding the marker(s), stimulatory molecules, co-stimulatory protein(s), and antigen and may include promoters, enhancers, polyadenylation signals, and other sequences necessary for transport of the molecule to the appropriate cellular compartment, which in certain embodiments, is the outer mitochondrial membrane (Gonzales-Garcia et al., *Development* 120:3033 (1994)). When the nucleic acid is a cDNA in a recombinant expression vector, the regulatory functions responsible for transcription and/or translation of the cDNA are often provided by viral sequences. Examples of commonly used viral promoters include those derived from polyoma, adenovirus 2, cytomegalovirus and simian virus 40, and retroviral LTRs (long terminal repeats).

Regulatory sequences linked to the cDNA can be selected to provide constitutive or inducible transcription. Inducible transcription can be accomplished by, for example, use of an inducible enhancer. Thus, in a specific embodiment of the invention the nucleic acid molecule encoding a desired protein such as CD32, CD28, 4-1BB ligand, CD86 or other stimulatory or co-stimulatory proteins is under the control of an inducible control element such that expression of the desired protein can be turned on or off (or intermediate levels in between) using an agent which affects the inducible control element (e.g., expression can be modulated by modulating the concentration of the inducing agent in the presence of the T cell). This allows for switching on or off of the expression of the protein. These regulatory sequences can function either in vitro or in vivo. Illustrative inducible or otherwise regulated expression systems those controlled by heavy metals (Mayo et al., 1982 Cell 29:99-108), RU-486 (a progesterone antagonist) (Wang et al., 1994 *Proc. Natl. Acad. Sci. USA* 91:8180-8184), steroids (Mader and White, 1993 *Proc. Natl. Acad. Sci. USA* 90:5603-5607), and tetracycline (Gossen and Bujard 1992 *Proc. Natl. Acad. Sci. USA* 89:5547-5551; U.S. Pat. No. 5,464,758). Thus, inducible expression of a variety of proteins useful in the present invention can be used in vivo for production of a gene therapy product. Likewise, an inducible expression system can be used to transduce or transfect a population of T cells, either polyclonal, antigen-specific, clonal, or T cell lines, which can then be infused in a patient and further induced in vivo to express a desired protein. In an additional embodiment, the EMSP of the present invention can be modified with a gene under the control of inducible expression control element. These EMSP can then also be administered to a patient and induced in vivo to express a desired protein. Within this and other contexts of the present invention, the induced EMSP can be used to break tolerance against tumor antigens, autoantigens, or other pathogenic antigens such as viral antigens. The EMSP of the present invention can alaso be used to break tolerance in vitro, as described herein, whereby the T cells are then infused into a patient. In another embodiment, EMSP or T cells of the present invention can be transfected or transduced with a gene encoding a homing molecule or other so called "addressins" under the control of an inducible expression element. Such modified EMSP or activated T cells can then be induced in vivo or in vitro. Such EMSP or T cells expressing the induced gene would then be used to home to a particular site of interest, for example a site of tumor or other disease such as autoimmune disease or viral infection. The skilled artisan would readily recognize that any variety of proteins would be useful under the control of an inducible expression control element or promoter, e.g., cytokines, homing receptors, addressing, tumor antigens, viral antigens, or other proteins useful for the recruitment of other immune cells to a site such as a lymph node, for destruction or activation.

The EMSP of the present invention are generally irradiated or otherwise rendered non-dividing prior to contact with target cells such that the EMSP are no longer dividing. In one embodiment of the present invention, the EMSPs are irradiated with 100Gy (10,000 rads). However, one of skill in the art would readily recognize that the amount of irradiation can be optimized according to the type of EMSP. Also, other chemical methods could serve the same function, such as formamide fixation, or mitomycin C, for example. In embodiments where synthesized lipid bilayers are used as a scaffold for generating EMSP, the skilled artisan would recognize that treatments such as irradiation are not necessary. Further, treatment to render the EMSP non-viable or non-dividing is unnecessary when such cells are to be removed by selection or other means prior to infusion.

The source of EMSP can be autologous, allogeneic, syngeneic, xenogeneic, or chemically synthesized. In another embodiment, the cells can be derived from a product of cell fusion or a cell hybrid (e.g., fusions of cells inter or intra species).

The EMSP can be stored under a variety of conditions, such as at room temperature, 4° C., cryopreserved, or freeze-dried. The EMSPs can also be fixed using any number of common fixatives such as formaldehyde or formamide.

The agents can be added to the EMSP before, during or after mixing with target cells.

The EMSP of the present invention can be used in in vitro or in vivo settings. For example, EMSP can be administered in vivo at local tumor sites or disease sites or can be administered systemically. As described further below, pharmaceutical compositions comprising the EMSP of the present invention are administered via any variety of routes and doses and can be determined by the skilled artisan. EMSP can be loaded with or otherwise have attached thereto ligands/antibodies in vivo by systemic or local administration following administration of EMSP. Similarly, ligand and/or ligand receptor can be induced to be expressed following transfer using drugs, such as tetracycline, to drive expression off of inducible gene elements.

Generally, T cells of the present invention are first stimulated resulting in upregulation and/or downregulation of certain key molecules followed by or concomitant with exit from the GO phase. Subsequently, these T cells can be expanded to large numbers using a variety of different molecules as described herein below.

Sources of T Cells

In one aspect of the present invention, ex vivo T cell expansion can be performed by isolation of T cells and subsequent stimulation followed by further expansion. In one embodiment of the invention, the T cells may be stimulated by a single agent. In another embodiment, T cells are stimulated with two agents, one that induces a primary signal and a second that is a co-stimulatory signal. Ligands useful for stimulating a single signal or stimulating a primary signal and an accessory molecule that stimulates a second signal may be used in soluble form, attached to the surface of a cell, such as an EMSP, or immobilized on a surface as described herein. In a preferred embodiment both primary and secondary agents are co-immobilized on a surface, for example a bead or an EMSP. In one embodiment, the molecule providing the primary activation signal, such as a CD3 ligand, and the co-stimulatory molecule, such as a CD28 ligand or 4-1BB ligand are coupled to or loaded on the same surface, for example, a particle or an EMSP. Further, as noted earlier, one, two, or more stimulatory molecules may be used on the same or differing surfaces or EMSP.

Prior to expansion, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as $CD28^+$, $CD4^+$, $CD8^+$, $CD45RA^+$, and $CD45RO^+$T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of $CD8^+$ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/ml. In other embodiments, the concentration used can be from about $1\times10^5$/ml to $1\times10^6$/ml, and any integer value in between.

If desired or necessary, monocyte populations (i.e., CD14$^+$ cells) may be depleted from blood preparations prior to ex vivo expansion by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Dynal AS under the trade name Dynabeads™. Exemplary Dynabeads™ in this regard are M-280, M-450, and M-500. In one aspect, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be expanded. In certain embodiments the irrelevant beads include beads coated with sheep anti-mouse antibodies, goat anti-mouse antibodies, and human serum albumin.

In brief, such depletion of monocytes is performed by preincubating PBMC isolated from whole blood or apheresed peripheral blood with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after said depletion.

T cells for stimulation can also be frozen after the washing step, which does not require the monocyte-removal step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease as described herein. In certain embodiments, antigen-specific T cells can be induced by vaccination of a patient with a particular antigen, either alone or in conjunction with an adjuvant or pulsed on dendritic cells. Antigen-specific cells for use in expansion using the EMSP of the present invention may also be generated in vitro using any number of methods known in the art, for example, as described in U.S. Patent Application No. 60/469, 122 entitled, GENERATION AND ISOLATION OF ANTIGEN-SPECIFIC T CELLS, filed May 8, 2003, or in U.S. Pat. Nos. 6,040,177 and 5,872,642. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion with EMSP. Sorting or positively selecting antigen-specific cells can be carried out using peptide-MHC tetramers (Altman, et al., *Science*. Oct. 4, 1996; 274(5284):94-6.). In one embodiment antigen-specific T cells are isolated by contacting said T cells with antibodies specific for T cell activation markers. Antibodies that can be used with the methods of the present invention include, but are not limited to, anti-CD25, anti-CD54, anti-CD69, anti-CD38, anti-CD45RO, anti-CD49d, anti-CD40L, anti-CD137, anti-IFN-γ, IL-2, IL-4, and other activation induced cytokines, and anti-CD134 antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

Peptide-MHC tetramers can be generated using techniques known in the art and can be made with any MHC molecule of interest and any antigen of interest as described herein. Illustrative antigens that can be used include but are not limited to, melanoma antigen Melan-A (also referred to as melanoma antigen recognized by T cells or MART-1), melanoma antigen-encoding genes 1, 2, and 3 (MAGE-1, -2, -3), melanoma GP 100, carcinoembryonic antigen (CEA), the breast cancer antgien, Her-2/Neu, telomerase reverse transcriptase (hTERT), serum prostate specific antigen (PSA), Wilm's Tumor (WT-1), mucin antigens, MUC-1, -2, -3, -4, and B cell lymphoma idiotypes. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., *J. Immunol.* 152:163, 1994).

Further, antigenic epitopes for use in the present invention may generally be identified using well known techniques, such as those summarized in Paul, *Fundamental Immunology*, 3rd ed., 243-247 (Raven Press, 1993) and references cited therein. Representative techniques for identifying epitopes include screening polypeptides for the ability to react with antigen-specific T cell lines or clones. Such screens may generally be performed using methods well known to those of ordinary skill in the art, such as those described in Harlow and Lane, *Antibodies: A Laboratory Manual*, Cold Spring Harbor Laboratory, 1988. Epitopes may also be identified using computer analysis, such as the Tsites program (see Rothbard and Taylor, *EMBO J* 7:93-100, 1988; Deavin et al., *Mol. Immunol.* 33:145-155, 1996), which searches for peptide motifs that have the potential to elicit T helper responses. CTL epitopes with motifs appropriate for binding to human class I or class II MHC may be identified according to BIMAS (Parker et al., *J Immunol.* 152:163, 1994) and other HLA peptide binding prediction analyses. To confirm peptide binding to human class I or class II MHC molecules, peptide binding assays known in the art may be used. To confirm immunogenicity, a peptide may be tested using an HLA A2 or other transgenic mouse model and/or an in vitro stimulation assay using dendritic cells, fibroblasts or peripheral blood cells.

Stimulation of a Cell Population

As noted above, the present invention provides compositions and methods for stimulating a cell population by binding moieties on the surfaces of the cells in that population. Contacting a cell population with an agent (e.g., a ligand) that binds to a cell surface moiety can stimulate the cell population. The ligand may be in solution but also may be attached to a surface. Ligation of cell surface moieties, such as a receptor, may generally induce a particular signaling pathway. Recent studies suggest that for signaling to occur, critical concentrations of lipid rafts containing the requisite receptors must aggregate. By way of example, raft aggregation may be facilitated in vivo or in vitro by attaching ligands for particular cell surface moieties to an EMSP and exposing the ligand-bearing EMSP to the cells of interest.

The methods of the present invention relate to the stimulation of a target cell by introducing a ligand or agent that binds to a cellular moiety, thereby inducing a cellular event. Binding of the ligand or agent to the cell may trigger a signaling pathway that in turn activates particular phenotypic or biological changes in the cell. The stimulation of a target cell by introducing a ligand or agent that binds to a cellular moiety as described herein may upregulate or downregulate any number of cellular processes leading to particular phenotypic or biological changes in the cell. The activation of the cell may enhance normal cellular functions or initiate normal cell functions in an abnormal cell. The method described herein provides stimulation by contacting the cells with the ligand or agent that binds a cell surface moiety. Stimulation of a cell may be enhanced or a particular cellular event may be stimulated by introducing a second agent or ligand that ligates a second cell surface moiety. This method may be applied to any cell for which ligation of a cell surface moiety leads to a signaling event. The invention further provides means for selection or culturing the stimulated cells. The prototypic example described is stimulation of T cells, but one of ordinary skill in the art will readily appreciate that the method may be applied to other cell types. By way of example, cell types that may be stimulated and selected include fibroblasts, neuroblasts, lung cells, hematopoietic stem cells and hematopoietic progenitor cells ($CD34^+$ cells), mesenchymal stem cells, mesenchymal progenitor cells, neural and hepatic progenitor and stem cells, dendritic cells, cytolytic T cells ($CD8^+$ cells), T helper cells ($CD4^+$ cells), B-cells, NK cells, other leukocyte populations, pluripotent stem cells, multi-potent stem cells, islet cells, etc. Accordingly, the present invention also provides populations of cells resulting from this methodology as well as cell populations having distinct phenotypical characteristics, including T cells with specific phenotypic characteristics.

As noted above a variety of cell types may be utilized within the context of the present invention. For example, cell types such as B cells, T cells, NK cells, other blood cells, neuronal cells, lung cells, glandular (endocrine) cells, bone forming cells (osteoclasts, etc.), germ cells (e.g., oocytes), epithelial cells lining reproductive organs, and others may be utilized. Cell surface moiety-ligand pairs could include (but not exclusively): T cell antigen receptor (TCR) and anti-CD3 mAb, TCR and major histocompatibility complex (MHC)+ antigen, TCR and peptide-MHC tetramer, TCR and superantigens (e.g., staphylococcal enterotoxin B (SEB), toxic shock syndrome toxin (TSST), etc.), B cell antigen receptor (BCR) and anti-Ig, BCR and LPS, BCR and specific antigens (univalent or polyvalent), NK receptor and anti-NK receptor antibodies, FAS (CD95) receptor and FAS ligand, FAS receptor and anti-FAS antibodies, CD54 and anti-CD54 antibodies, CD2 and anti-CD2 antibodies, CD2 and LFA-3 (lymphocyte function related antigen-3), cytokine receptors and their respective cytokines, cytokine receptors and anti-cytokine receptor antibodies, TNF-R (tumor necrosis factor-receptor) family members and antibodies directed against them, TNF-R family members and their respective ligands, adhesion/homing receptors and their ligands, adhesion/homing receptors and antibodies against them, oocyte or fertilized oocyte receptors and their ligands, oocyte or fertilized oocyte receptors and antibodies against them, receptors on the endometrial lining of uterus and their ligands, hormone receptors and their respective hormone, hormone receptors and antibodies directed against them, and others.

The nature of the binding of a multivalent or monovalent receptor by a ligand will either result in the multimerization of the receptors, or aggregation/orientation of the receptors, such that signaling or cell response is upregulated, downregulated, accelerated, improved, or otherwise altered so as to confer a particular benefit, such as cell division, cytokine secretion, cell migration, increased cell-cell interaction, etc.

Two examples are given below that illustrate how such a multimerization, aggregation, or controlled reorientation of cell surface moieties could be of practical benefit.

In one example, normal T cell activation by antigen and antigen presenting cells usually results in aggregation of TCR rafts, cytoskeletal reorganization, polarization of "activation" signals and cell division, for example. Using man-made approaches, such as those described herein, in the absence of "normal" in-vivo T cell activation, one could accelerate, improve, or otherwise affect the functions described above, in particular through the accelerated, controlled, and spatially oriented ligation of TCR and CD28 or 4-1BB or other co-stimulatory molecules. Benefits include improved cell expansion in vitro resulting in higher numbers of infuseable and more robust cells for therapeutic applications. Other benefits could be improved receptor "aggregation" for cells with defects, such as lower-than-normal TCR density on the cell surface. Similarly, in vivo applications could be beneficial where specific T cell populations need to be activated, such as tumor-specific T cells at tumor sites. Improved receptor aggregation and orientation could provide an activation signal otherwise difficult to obtain for functionally tolerized T cells. Within this and other contexts of the present invention, the EMSP can be used to break tolerance against tumor antigens, autoantigens, or other pathogenic antigens such as viral antigens. Further, such activation could be used within the context of antigen specific T cells. In this regard T cells from a tumor could be isolated and expanded and infused into the patient. Similarly, T cells exposed to an antigen either in vivo or in vitro could be expanded by the present methodologies.

In one particular embodiment of the invention, a T cell population may be stimulated by ligating the surfaces of the T cells. In one aspect of the present invention, antibodies to CD3 and CD28 are loaded onto an EMSP. In another aspect of the present invention, any ligand that binds the TCR/CD3 complex and initiates a primary stimulation signal may be utilized as a primary activation agent loaded onto or expressed by the EMSP. Any ligand that binds CD28 and initiates the CD28 signal transduction pathway, thus causing co-stimulation of the cell with a CD3 ligand and enhancing activation of a population of T cells, is a CD28 ligand and accordingly, is a co-stimulatory agent within the context of the present invention.

In other aspects of the present invention, T cells can be exposed to a bead conjugated agent or soluble forms of agents or ligands prior to or concurrently with the EMSPs of the present invention as described herein.

In certain embodiments, the EMSP of the present invention can be contacted with paramagnetic particles such that said paramagnetic particles are engulfed by the EMSP. EMSP comprising paramagnetic particles can then be subjected to magnetic force and concentrated or localized to a particular site of interest, such as a tumor, site of viral infection or site of autoimmune disease, and/or otherwise selected, either in vitro or in vivo.

In certain embodiments the EMSP of the present invention can be contacted with synthesized or magnetic liposomes or derivatized biodegradable glass.

The Primary Signal

The biochemical events responsible for ex vivo T cell stimulation are set forth briefly below. Interaction between the TCR/CD3 complex and antigen presented in conjunction with either MHC class I or class II molecules on an antigen-presenting cell initiates a series of biochemical events termed antigen-specific T cell activation. Accordingly, activation of T cells can be accomplished by stimulating the T cell TCR/CD3 complex or by stimulating the CD2 surface protein. An anti-CD3 monoclonal antibody can be used to activate a population of T cells via the TCR/CD3 complex. A number of anti-human CD3 monoclonal antibodies are commercially available, exemplary are OKT3, prepared from hybridoma cells obtained from the American Type Culture Collection, and monoclonal antibody G19-4. Similarly, stimulatory forms of anti-CD2 antibodies are known and available. Stimulation through CD2 with anti-CD2 antibodies is typically accomplished using a combination of at least two different anti-CD2 antibodies. Stimulatory combinations of anti-CD2 antibodies that have been described include the following: the T11.3 antibody in combination with the T11.1 or T11.2 antibody (Meuer et al., *Cell* 36:897-906, 1984), and the 9.6 antibody (which recognizes the same epitope as T11.1) in combination with the 9-1 antibody (Yang et al., *J. Immunol.* 137:1097-1100, 1986). Other antibodies that bind to the same epitopes as any of the above described antibodies can also be used. Additional antibodies, or combinations of antibodies, can be prepared and identified by standard techniques.

A primary activation signal can also be delivered to a T cell through other mechanisms. For example, a combination that may be used includes a protein kinase C (PKC) activator, such as a phorbol ester (e.g., phorbol myristate acetate), and a calcium ionophore (e.g., ionomycin, which raises cytoplasmic calcium concentrations), or the like. The use of such agents bypasses the TCR/CD3 complex but delivers a stimulatory signal to T cells. Other agents acting as primary signals may include natural and synthetic ligands. A natural ligand may include MHC with or without a peptide presented. Other ligands may include, but are not limited to, a peptide, polypeptide, growth factor, cytokine, chemokine, glycopeptide, soluble receptor, steroid, hormone, mitogen, such as PHA, or other superantigens, peptide-MHC tetramers (Altman, et al., *Science.* 1996 Oct. 4; 274(5284):94-6.) and soluble MHC dimers (Dal Porto, et al, *Proc Natl Acad Sci USA Jul.* 15, 1993; 90). Within the context of the present invention, the use of the EMSP for stimulation may result in stimulation such that no secondary signal is required to induce proliferation of T cells.

In other embodiments, signal transduction events of any kind may be magnified or analyzed by utilizing the current invention. For example, G protein-coupled receptors may be stimulated and measured using the methods of the present invention.

The Secondary Signal

While stimulation of the TCR/CD3 complex or CD2 molecule appears to be required for delivery of a primary activation signal in a T cell, a number of molecules on the surface of T cells, termed accessory or co-stimulatory molecules, have been implicated in regulating the transition of a resting T cell to blast transformation, and subsequent proliferation and differentiation. Thus, in addition to the primary activation signal. induction of T cell responses requires a second, co-stimulatory signal. One such co-stimulatory or accessory molecule, CD28, is believed to initiate or regulate a signal transduction pathway that is distinct from any stimulated by the TCR complex. Another such co-stimulatory or accessory molecule, 4-1BB, preferentially stimulates $CD8^+$ T cells but may also be used for the stimulation of $CD4^+$ T cells.

Therefore, to enhance activation and proliferation of a population of T cells in the absence of exogenous growth factors or accessory cells, an accessory molecule on the surface of the T cell, such as CD28 or 4-1BB, is stimulated with a ligand that binds the accessory molecule. In one embodiment, stimulation of the accessory molecule CD28 and T cell activation occur simultaneously by contacting a population of T cells with an EMSP to which a ligand that binds CD3 and a ligand that binds CD28 are attached. In another embodiment, stimulation of the accessory molecule 4-1BB and T cell activation occur simultaneously by contacting a population of T cells with an EMSP to which a ligand that binds CD3 and a ligand that binds 4-1BB are attached. Activation of the T cells, for example, with an anti-CD3 antibody, and stimulation of the CD28 accessory molecule results in selective proliferation of $CD4^+$ T cells. Activation of the T cells, for example, with an anti-CD3 antibody, and stimulation of the 4-1BB accessory molecule results in preferential proliferation of $CD8^+$ T cells.

Accordingly, one of ordinary skill in the art will recognize that any agent, including an anti-CD28 antibody or fragment thereof capable of cross-linking the CD28 molecule, or a natural ligand for CD28 can be used to stimulate T cells. Exemplary anti-CD28 antibodies or fragments thereof useful in the context of the present invention include monoclonal antibody 9.3 ($IgG2_a$) (Bristol-Myers Squibb, Princeton, N.J.), monoclonal antibody KOLT-2 (IgG1), 15E8 (IgG1), 248.23.2 (IgM), and EX5.3D10 ($IgG2_a$) (ATCC HB11373). Exemplary natural ligands include the B7 family of proteins, such as B7-1 (CD80) and B7-2 (CD86) (Freedman et al., *J. Immunol.* 137:3260-3267, 1987; Freeman et al., *J. Immunol.* 143:2714-2722, 1989; Freeman et al., *J. Exp. Med.* 174:625-631, 1991; Freeman et al., *Science* 262:909-911, 1993; Azuma et al., *Nature* 366:76-79, 1993; Freeman et al, *J. Exp. Med.* 178:2185-2192, 1993). In addition, binding homologues of a natural ligand, whether native or synthesized by chemical or recombinant techniques, can also be used in accordance with the present invention. Other agents acting as secondary signals may include natural and synthetic ligands. Agents may include, but are not limited to, other antibodies or fragments thereof, a peptide, polypeptide, growth factor, cytokine, chemokine, glycopeptide, soluble receptor, steroid, hormone, mitogen, such as PHA, or other superantigens.

Likewise, one of ordinary skill in the art will recognize that any agent, including an anti-4-1BB antibody or fragment thereof capable of cross-linking the 4-1BB molecule, or a natural ligand for 4-1BB can be used to stimulate T cells. In particular, human 4-1BB ligand can be cloned from B cells into the pcDNA3. or other suitable vectors and be transfected into an EMSP.

In a further embodiment of the invention, activation of a T cell population may be enhanced by co-stimulation of other T cell integral membrane proteins. For example, binding of the T cell integrin LFA-1 to its natural ligand, ICAM-1, may enhance activation of cells. Another cell surface molecule that may act as a co-stimulator for T cells is VCAM-1 (CD106) that binds very-late-antigen-4 (VLA-4) on T cells.

In certain embodiments of the present invention, stimulation, activation, and expansion of T cells using EMSP as described herein enhances expression of certain key molecules in T cells that protect again apoptosis or otherwise proling survival in vivo or in vitro. Apoptosis usually results from induction of a specific signal in the T cell. Thus, the compositions and methods of the invention provide for protecting a T cell from cell death resulting from stimulation of the T cell. It is known in the art that presently cross-linking of the T cell receptor, either by a polyclonal activator, such as an anti-CD3 antibody and/or anti-CD28 antibody, or alternatively by an antigen on an antigen presenting cell (APC), in the absence of a co-stimulatory signal, can result in T cell anergy or T cell death. Therefore, also included in the present invention is the enhanced T cell growth by protection from premature death or from absence or depletion of recognized T cell growth markers, such as Bcl-xL, growth factors, cytokines, or lymphokines normally necessary for T cell survival, as well as from Fas or Tumor Necrosis Factor Receptor (TNFR) cross-linking or by exposure to certain hormones or stress.

One of skill in the art will appreciate that cells other than T cells may be stimulated by binding of an agent that ligates a cell surface moiety and induces aggregation of the moiety, which in turn results in activation of a signaling pathway. Other such cell surface moieties include, but are not limited to, GPI-anchored folate receptor (CD59), human IgE receptor (FcεRi receptor), BCR, EGF receptor, insulin receptor, ephrin B1 receptor, neurotrophin, glial-cell derived neutrophic factor (GNDF), hedgehog and other cholesterol-linked and palmitoylated proteins, H-Ras, integrins, endothelial nitric oxide synthase (eNOS), FAS, members of the TNF receptor family, GPI-anchored proteins, doubly acylated proteins, such as the Src-family kinases, the alpha-subunit of heterotrimeric G proteins, and cytoskeletal proteins.

The cell population may be stimulated as described herein, such as by contact with an anti-CD3 antibody or an anti-CD2 antibody loaded onto an EMSP engineered to express an Fcγ receptor such as CD32, or by contact with a protein kinase C activator (e.g., bryostatin) in conjunction with a calcium ionophore. For co-stimulation of an accessory molecule on the surface of the T cells, a ligand that binds the accessory molecule is used. For example, a population of CD4+ cells can be contacted with an anti-CD3 antibody and an anti-CD28 antibody, under conditions appropriate for stimulating proliferation of the T cells. Similarly, to stimulate proliferation of CD8+ T cells, an anti-CD3 antibody and the 4-1BB ligand can be used. Alternatively, to stimulate proliferation of CD8+ T cells, an anti-CD3 antibody and the anti-CD28 antibody B-T3, XR-CD28 (Diaclone, Besançon, France) can be used as can other methods commonly known in the art (Berg et al., *Transplant Proc.* 30(8):3975-3977, 1998; Haanen et al., *J Exp. Med.* 190(9):1319-1328, 1999; Garland et al., *J. Immunol Meth.* 227(1-2):53-63, 1999).

The primary stimulatory signal and the co-stimulatory signal for the T cell may be provided by different protocols. For example, the agents providing each signal may be in solution or coupled to a surface such as loaded on an EMSP as described herein. When loaded on an EMSP or other surface, such as a paramagnetic bead, the agents may be loaded on the same EMSP or coupled to the same surface (i.e., in "cis" formation) or can be loaded onto separate EMSP or coupled to separate surfaces (i.e., in "trans" formation). Alternatively, one agent may be loaded on an EMSP or coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then bound to a surface, such as a cell expressing Fc receptors or an antibody or other binding agent which will bind to the agents. In a preferred embodiment, the two agents are loaded onto the same EMSP that has been engineered to express an FCγ receptor such as CD32. By way of example, the agent providing the primary activation signal is an anti-CD3 antibody and the agent providing the co-stimulatory signal is an anti-CD28 antibody; and both agents are loaded onto an EMSP in equivalent molecular amounts. In one embodiment, a 1:1 ratio of each antibody loaded onto an EMSP for CD4+ T cell expansion and T cell growth is used. In certain aspects of the present invention, a ratio of anti CD3:CD28 antibodies loaded onto an EMSP is used such that an increase in T cell expansion is observed as compared to the expansion observed using a ratio of 1:1. In one particular embodiment an increase of from about 0.5 to about 3 fold is observed as compared to the expansion observed using a ratio of 1:1. In one embodiment, the ratio of CD3:CD28 antibody loaded onto an EMSP ranges from 1 00:1 to 1:1000 and all integer values there between. In one aspect of the present invention, more anti-CD28 antibody is loaded onto an EMSP than anti-CD3 antibody, i.e. the ratio of CD3:CD28 is less than one. In certain embodiments of the invention, the ratio of anti CD28 antibody to anti CD3 antibody loaded onto an EMSP is greater than 2:1. In one particular embodiment, a 1:1000 CD3:CD28 ratio of antibody loaded onto an EMSP is used. In another embodiment, a 1:500 CD3:CD28 ratio of antibody loaded onto an EMSP is used. In another embodiment, a 1:250 CD3:CD28 ratio of antibody loaded onto an EMSP is used. In another embodiment, a 1:100 CD3:CD28 ratio of antibody loaded onto an EMSP is used. In a further embodiment, a 1:75 or 1:50 CD3:CD28 ratio of antibody loaded onto an EMSP is used. In another embodiment, a 1:40 or 1:30 CD3:CD28 ratio of antibody loaded onto an EMSP is used. In one preferred embodiment, a 1:100 CD3:CD28 ratio of antibody loaded onto an EMSP is used. In another preferred embodiment, a 1:50 CD3:CD28 ratio of antibody loaded onto an EMSP is used. In another preferred embodiment, a 1:25 CD3:CD28 ratio of antibody loaded onto an EMSP is used. In one preferred embodiment, a 1:10 CD3:CD28 ratio of antibody loaded onto an EMSP is used. In another embodiment, a 1:3 CD3:CD28 ratio of antibody loaded onto an EMSP is used. In yet another embodiment, a 3:1 CD3:CD28 ratio of antibody loaded onto an EMSP is used.

Ratios of EMSP, or other particles as described herein, to cells from 1:10000 to 10000:1 and any integer values in between may be used to stimulate T cells or other target cells. As those of ordinary skill in the art can readily appreciate, the ratio of EMSP to cells may dependant on EMSP size relative to the target cell. For example, a small EMSP could only bind a few cells, while a large EMSP could bind many. In certain embodiments the ratio of cells to EMSP ranges from 1:100 to 100:1 and any integer values in-between and in further embodiments the ratio comprises 1:9, 1:8, 1:7, to 9:1 and any integer values in between, can also be used to stimulate T cells. In a preferred embodiment wherein the EMSP is K32 as described herein in the Examples, the ratio of target cell to EMSP is most suitable at about 1:1 to about 1:100. The ratio of anti-CD3- and anti-CD28-loaded EMSP to T cells that result in T cell stimulation can vary as noted above, however certain preferred values include at least 1:200, 1:150, 1:100, 1:75, 1:50, 1:45, 1:40, 1:35, 1:30, 1:25, 1:20, 1:15, 1:10, 1:9, 1:8, 1:7, 1:6, 1:5, 1:4, 1:3, 1:2.5, 1:2, 1:1.5, 1:1, 2:1, 3:1, 4:1 5:1, 6:1, 7:1, 8:1, 9:1, 10:1, 15:1, 20:1, to 25:1, with one preferred ratio being at least 1:1 EMSP per T cell. In one embodiment, a ratio of EMSP to cells of 1:1 or less is used.

Using different EMSP:cell ratios can lead to different outcomes with respect to expansion of antigen-specific T cells, as described for example in U.S. Patent Application No. 60/469, 122, filed May 8, 2003. In particular, EMSP:cell ratios can be varied to selectively expand or delete antigen-specific (memory) T cells. In one embodiment, the particular EMSP: cell ratio used selectively deletes antigen-specific T cells. In a further embodiment, the particular EMSP:cell ratio used selectively expands antigen-specific T cells. For example, EMSP to cell ratios of 1:100, 1:50, 1:25, 1:5 or 1:2.5 and the like are used to expand antigen-specific T cells. Low EMSP: cell ratio can help preserve and promote expansion of memory (antigen-specific) T cells. Additionally, when additional EMSPs are added at very low ratios (1:10, 1:25, 1:50, 1:100) at various days of culture (e.g. day 5, 7, or 9), one can enhance and even promote preferential expansion of the memory cells. With either 1:5 or 1:2.5 EMSP:cell ratio as initial simulus, addition of 1:10, 1:25, and to some extent 1:50 and 1:100 EMSP:cell ratio at days 5 and 7 may preserve and enhance further expansion of memory cells that would otherwise not occur with a single stimulation at day 0. Therefore, the compositions and methods described herein can be used to expand specific populations of T cells, or to delete specific populations of T cells, for use in any variety of immunotherapeutic settings described herein.

Using certain methodologies it may be advantageous to maintain long-term culture of a population of T cells following the initial activation and stimulation, by separating the T cells from the stimulus after a period of about 12 to about 14 days. In certain embodiments, it may be desirable to separate the T cells from the stimulus after a period of about 2, 3, 4, 5, 6, 7, 8, 9, 10, or 11 days. In certain embodiments, it may be desirable to separate the T cells from the stimulus after a period of less than one day, such as after about an hour, or 2, 3, 4, 5, 6, 7, 8, 9, 10, 11, 12, 13, 14, 15, 16, 17, 18, 19, 20, 21, 22, or 23 hours. The rate of T cell proliferation is monitored periodically (e.g., daily) by, for example, examining the size or measuring the volume of the T cells, such as with a Coulter Counter. In this regard, a resting T cell has a mean diameter of about 6.8 microns, and upon initial activation and stimulation, in the presence of the stimulating ligand, the T cell mean diameter will increase to over 12 microns by day 4 and begin to decrease by about day 6. When the mean T cell diameter decreases to approximately 8 microns, the T cells may be reactivated and re-stimulated to induce further proliferation of the T cells. Alternatively, the rate of T cell proliferation and time for T cell re-stimulation can be monitored by assaying for the presence of cell surface molecules, such as, CD154, CD54, CD25, CD137, CD134, which are induced on activated T cells. Intracellular or secreted cytokines can also be monitored such as IL-2, IFN-γ, TNF-α, GM-CSF, etc.

In further embodiments of the present invention, the cells, such as T cells, are combined with loaded EMSP, the EMSP and the cells are subsequently separated, and then the cells are cultured. In an alternative embodiment, prior to culture, the antibody or ligand loaded EMSP and cells are not separated but are cultured together.

By way of example, when T cells are the target cell population, the cell surface moieties may be ligated by allowing irradiated EMSP expressing CD86 and to which anti-CD3 and anti-CD28 are attached via the Fcγ receptor to contact the T cells. In another example of the present invention, when T cells are the target cell population, the cell surface moieties may be ligated by allowing irradiated EMSP expressing the 4-1BB ligand and to which anti-CD3 and anti-CD28 are attached via the Fcγ receptor to contact the T cells.

The buffer that the cells are suspended in may be any that is appropriate for the particular cell type. When utilizing certain cell types the buffer may contain other components, e.g., 1-5% serum, necessary to maintain cell integrity during the process. In another embodiment, the cells and EMSP may be combined in cell culture media. The cells and EMSP may be mixed, for example, by rotation, agitation or any means for mixing, for a period of time ranging from one minute to several hours. As noted above, generally the EMSP of the present invention are irradiated prior to contact with target cells such as T cells. Generally, EMSP are irradiated prior to being loaded with antibodies or ligands as described herein.

In one embodiment of the present invention, the mixture may be cultured for several hours (about 3 hours) to about 20 days or any hourly integer value in between. In another embodiment, the mixture may be cultured for 21 days. In one embodiment of the invention the EMSP and the T cells are cultured together for about eight days. In another embodiment, the EMSP and T cells are cultured together for 2-3 days. Several cycles of stimulation may also be desired such that culture time of T cells can be 60 days or more.

The period of initial stimulation or restimulation as described herein (contact with agents as described herein) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The period of initial stimulation or restimulation as described further herein (contact with agents as described herein) can be longer, for example 1, 2, 3, 4, 5, 6, 7, 8, 9, 10, 11, 12, 13, 14, or more days.

Conditions appropriate for T cell culture include an appropriate media (e.g., Minimal Essential Media or RPMI Media 1640 or, X-vivo 15, (BioWhittaker)) that may contain factors necessary for proliferation and viability, including serum (e.g., fetal bovine or human serum), interleukin-2 (IL-2), insulin, IFN-γ, IL-4, GM-CSF, IL-10, IL-12, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, with added amino acids and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, and preferably n\not in cultures of cells that are to be infused into a subject. The target cells are maintained under conditions necessary to support growth, for example, an appropriate temperature (e.g., 37° C.) and atmosphere (e.g., air plus 5% $CO_2$).

Cells stimulated by the methods of the present invention are activated as shown by the induction of signal transduction, expression of cell surface markers and/or proliferation. One such marker appropriate for T cells is CD154 which is an important immunomodulating molecule. The expression of CD154 is extremely beneficial in amplifying the immune response. CD154 interacts with the CD40 molecule expressed on many B cells, dendritic cells, monocytes, and some endothelial cells. Accordingly, this unexpected and surprising increase in CD154 expression is likely to lead to more efficacious T cell compositions. Stimulation of CD3+ cells as described herein provides T cells that express a 1.1 to 20-fold increases in the levels of certain cell surface markers such as CD154 expression on days 1, 2, 3, or 4 following stimulation. Expression of another cell surface marker, CD25, also was greater on T cells after stimulation than on cells prior to culture or cells stimulated by other methods. Further, after simulation using the methods of the present invention, CD8+ T cells show increased Bcl-xL and IL-2 expression as described in the Examples below.

In another embodiment, T cells are initially stimulated with the EMSP and the T cells are then purified using any number of methods described herein, also including density gradient separation, elutriation and removal of dead cells. The remaining T cell population is substantially free of non-T cells and can then be incubated with any number of cytokines such as IL-2 in culture medium in order to promote further T cell proliferation.

One of skill in the art will appreciate that any target cell that can be stimulated by cell surface moiety ligation may be combined with the EMSP. Further, the EMSP may be separated from the cells prior to culture, at any point during culture, or at the termination of culture. In addition, the EMSP ligated to the target cells may be separated from the non-binding cells prior to culture or the other cells may remain in culture as well. In one embodiment, prior to culture, the EMSP and target cells are not separated but are cultured together.

Also contemplated by this invention, are means to increase the concentration of the target cells, for example, a T cell fraction bound to an EMSP coated with primary and secondary stimulatory molecules. For example, forces greater than gravitational force may be applied, for example, but not limited to, centrifugal force, transmembrane pressure, and a hydraulic force. Concentration may also be accomplished by filtration. In certain embodiments, the EMSP of the present invention can be contacted with paramagnetic particles, such as paramagnetic beads or magnetic liposomes, such that said paramagnetic particles are engulfed by the EMSP. EMSP comprising paramagnetic particles can then be subjected to magnetic force and concentrated and/or otherwise selected, either in vitro or in vivo.

One of skill in the art will readily appreciate that contact between the agent-coated or otherwise loaded EMSP and the cells to be stimulated can be increased by concentration using other forces. Accordingly, any means for concentrating cells with cell surface moiety binding ligands will be sufficient as long as the concentration brings together cells and agents in a manner that exceeds gravity or diffusion.

A cellular event induced by contact of target cells with the EMSP of the present invention may include, for example, receptor-mediated signal transduction that induces or suppresses a particular pathway, including an apoptotic pathway, or induces phosphorylation of proteins, or stimulates or suppresses growth signals.

In another embodiment, the time of exposure to stimulatory agents such as anti-CD3/anti-CD28-coated or otherwise loaded EMSP expressing CD86 or 4-1BB may be modified or tailored to obtain a desired T cell phenotype. Alternatively, a desired population of T cells can be selected using any number of selection techniques, prior to stimulation. One may desire a greater population of CD4+ T cells as opposed to CD8+ or regulatory T cells, because an expansion of CD4+ T cells could improve or restore overall immune responsiveness. While many specific immune responses are mediated by CD8+ antigen-specific T cells, which can directly lyse or kill undesired cells, most immune responses require the help of CD4+ T cells, which express important immune-regulatory molecules, such as GM-CSF, CD40L, and IL-2, for example. Increased numbers of CD4+ T cells can increase the amount of cell-expressed CD40L introduced into patients, potentially improving target cell visibility (improved APC function). Similar effects can be seen by increasing the number of infused cells expressing GM-CSF, or IL-2, all of which are expressed predominantly by CD4+ T cells. Alternatively, in situations where CD4-help is needed less and increased numbers of CD8+ T cells are desirous, the approaches described herein can also be utilized, by for example, pre-selecting for CD8+ cells prior to stimulation and/or culture. Such situations may exist where increased levels of IFN-γ or increased cytolysis of an undesired cell is preferred. In certain other embodiments, selection of a CD28-negative population may be desired.

T cells that have been exposed to varied stimulation times and EMSP expressing a variety of molecules may exhibit different characteristics. For example, typical blood or apheresed peripheral blood mononuclear cell products have a CD4+ T cell population that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Furthermore, one aspect of the present invention is the finding that stimulation with an EMSP expressing 4-1BB ligand and coated with anti-CD3 and CD28 antibodies preferentially stimulates and expands CD8+ cytotoxic T cells. Accordingly, depending on the purpose of treatment, infusing a subject with a T cell population comprising predominately of $T_H$ cells expanded with anti-CD3/anti-CD28 and CD86 EMSP may be advantageous. Similarly, if an antigen-specific subset of $T_C$ cells has been isolated it may be beneficial to expand this subset to a greater degree using EMSP expressing 4-1BB and further coated with anti-CD3 and anti-CD28 antibodies.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In one such example, among the important phenotypic markers that reproducibly vary with time are the high affinity IL-2 receptor (CD25), CD40 ligand (CD154), and CD45RO (a molecule that by preferential association with the TCR may increase the sensitivity of the TCR to antigen binding). As one of ordinary skill in the art readily appreciates, such molecules are important for a variety of reasons. For example, CD25 constitutes an important part of the autocrine loop that allows rapid T cell division. CD154 has been shown to play a key role in stimulating maturation of the antigen-presenting dendritic cells; activating B-cells for antibody production; regulating $T_H$ cell proliferation; enhancing $T_C$ cell differentiation; regulating cytokine secretion of both $T_H$ cells and antigen-presenting cells; and stimulating expression of co-stimulatory ligands, including CD80, CD86, and CD154.

Cytokine production peaks in the first few days of the ex vivo expansion process. Accordingly, because cytokines are known to be important for mediating T cell activation and function as well as immune response modulation, such cytokines are likely critical in the development of a therapeutic T cell product, that is able to undergo reactivation upon contact with an additional antigen challenge. Cytokines important in this regard, include, but are not limited to, IL-2, IL-4, TNF-α, and IFN-γ. Thus, by obtaining a population of T cells during the first few days of expansion and infusing these cells into a subject, a therapeutic benefit may occur in which additional activation and expansion of T cells in vivo occurs.

In addition to the cytokines and the markers discussed previously, expression of adhesion molecules known to be important for mediation of T cell activation and immune response modulation also change dramatically but reproducibly over the course of the ex vivo expansion process. For example, CD62L is important for homing of T cells to lymphoid tissues and trafficking T cells to sites of inflammation. Under certain circumstances of disease and injury, the presence of activated T cells at these sites may be disadvantageous. Because down-regulation of CD62L occurs early following activation, the T cells could be expanded for shorter periods of time. Conversely, longer periods of time in culture would generate a T cell population with higher levels of CD62L and thus a higher ability to target the activated T cells to these sites under other preferred conditions. Another example of a polypeptide whose expression varies over time is CD49d, an adhesion molecule that is involved in trafficking lymphocytes from blood to tissues spaces at sites of inflammation. Binding of the CD49d ligand to CD49d also allows the T cell to receive co-stimulatory signals for activation and proliferation through binding by VCAM-1 or fibronectin ligands. The expression of the adhesion molecule CD54, involved in T cell-APC and T cell-T cell interactions as well as homing to sites of inflammation, also changes over the course of expansion. Accordingly, T cells could be stimulated for selected periods of time that coincide with the marker profile of interest and subsequently collected and infused. Thus, T cell populations could be tailored to express the markers believed to provide the most therapeutic benefit for the indication to be treated.

Those of ordinary skill in the art will readily appreciate that the cell stimulation methodologies described herein may be carried out in a variety of environments (i.e., containers). For example, such containers may be culture flasks, culture bags, or any container capable of holding cells, preferably in a sterile environment. In one embodiment of the present invention a bioreactor is also useful. For example, several manufacturers currently make devices that can be used to grow cells and be used in combination with the methods of the present invention. See for example, Celdyne Corp., Houston, Tex.; Unisyn Technologies, Hopkinton, Mass.; Synthecon, Inc. Houston, Tex.; Aastrom Biosciences, Inc. Ann Arbor, Mich.; Wave Biotech LLC, Bedminster, N.J. Further, patents covering such bioreactors include U.S. Pat. Nos. 6,096,532; 5,985,653; 5,888,807; 5,190,878, which are incorporated herein by reference.

One aspect of the present invention provides stimulating and/or activating or otherwise culturing cells in a rocking, closed system and results in a profound enhancement in activation and expansion of these cells. Accordingly, in one embodiment, a bioreactor with a base rocker platform is used, for example such as "THE WAVE BIOREACTOR™" (Wave Biotech LLC, Bedminster, N.J.), that allows for varying rates of rocking and at a variety of different rocking angles. The skilled artisan will recognize that any platform that allows for the appropriate motion for optimal expansion of the cells is within the context of the present invention.

In certain embodiments, the capacity of the bioreactor container ranges from about 0.1 liter to about 200 liters of medium. The skilled artisan will readily appreciate that the volume used for culture will vary depending on the number of starting cells and on the final number of cells desired. In a related embodiment, the entire process of stimulation, activation, and expansion takes place using static conditions and/ or in a bioreactor. Illustrative bioreactors include, but are not limited to, "THE WAVE BIOREACTOR™".

In one particular embodiment, the cell stimulation methods of the present invention are carried out in a closed system, such as a bioreactor, that allows for perfusion of medium at varying rates, such as from about 0.1 ml/minute to about 3 ml/minute. Accordingly, in certain embodiments, the container of such a closed system comprises an outlet filter, an inlet filter, and a sampling port for sterile transfer to and from the closed system: In other embodiments, the container of such a closed system comprises a syringe pump and control for sterile transfer to and from the closed system. Further embodiments provide for a mechanism, such as a load cell, for controlling media in-put and out-put by continuous monitoring of the weight of the bioreactor container. In one embodiment the system comprises a gas manifold. In another embodiment, the bioreactor of the present invention comprises a $CO_2$ gas mix rack that supplies a mixture of ambient air and $CO_2$ and/or other gas mixes, to the bioreactor container and maintains the container at positive pressure. In another embodiment, the bioreactor of the present invention comprises a variable heating element.

In one embodiment, media is allowed to enter the container starting on day 2, 3, 4, 5, or 6 at about 0.5 to 5.0 liters per day until the desired final volume is achieved. In one preferred embodiment, media enters the container at 2 liters per day starting at day 4, until the volume reaches 10 liters. Once desired volume is achieved, perfusion of media can be initiated. In certain embodiments, perfusion of media through the system is initiated on about day 2, 3, 4, 5, 6, 7, 8, 9, 10, 11, or 12 of culture. In one embodiment, perfusion is initiated when the volume is at about 0.1 liter to about 200 liters of media. In one particular embodiment, perfusion is initiated when the final volume is at 4, 5, 6, 7, 8, 9, 10, or 20 liters.

In a further embodiment of the present invention, the cells, such as T cells, are cultured for up to 5 days in a closed, static system and then transferred to a closed system that comprises a rocking element to allow rocking of the culture container at varying speeds.

Although the antibodies used in the methods described herein can be readily obtained from public sources, such as the ATCC, antibodies to T cell accessory molecules and the CD3 complex can be produced by standard techniques. Methodologies for generating antibodies for use in the methods of the invention are well-known in the art and are discussed in further detail herein.

Agents

Agents contemplated by the present invention include protein ligands, natural ligands, and synthetic ligands. Agents that can bind to cell surface moieties, and under certain conditions, cause ligation and aggregation that leads to signaling include, but are not limited to, lectins (for example, PHA, lentil lectins, concanavalin A), antibodies, antibody fragments, peptides, polypeptides, glycopeptides, receptors, B cell receptor and T cell receptor ligands, extracellular matrix components, steroids, hormones (for example, growth hormone, corticosteroids, prostaglandins, tetra-iodo thyronine), bacterial moieties (such as lipopolysaccharides), mitogens, antigens, superantigens and their derivatives, growth factors, cytokine, viral proteins (for example, HIV gp-120), adhesion molecules (such as, L-selectin, LFA-3, CD54, LFA-1), chemokines, and small molecules. The agents may be isolated from natural sources such as cells, blood products, and tissues, or isolated from cells propagated in vitro, or prepared recombinantly, or by other methods known to those with skill in the art.

In one aspect of the present invention, when it is desirous to stimulate T cells, useful agents include ligands that are capable of binding the CD3/TCR complex, CD2, and/or CD28, and/or 4-1BB and initiating activation or proliferation, respectively. Accordingly, the term ligand includes those proteins that are the "natural" ligand for the cell surface protein, such as a B7 molecule for CD28, as well as artificial ligands such as antibodies directed to the cell surface protein or fusions of antibodies or other ligands. Such antibodies and fragments thereof may be produced in accordance with conventional techniques, such as hybridoma methods and recombinant DNA and protein expression techniques. Useful antibodies and fragments may be derived from any species, including humans, or may be formed as chimeric proteins, which employ sequences from more than one species.

Methods well known in the art may be used to generate antibodies, polyclonal antisera, or monoclonal antibodies that are specific for a ligand. Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second distinct mammalian species. Most commonly, a chimeric antibody has murine variable region sequences and human constant region sequences. Such a murine/human chimeric immunoglobulin may be "humanized" by grafting the complementarity determining regions (CDRs), which confer binding specificity for an antigen, derived from a murine antibody into human-derived V region framework regions and human-derived constant regions. Fragments of these molecules may be generated by proteolytic digestion, or optionally, by proteolytic digestion followed by mild reduction of disulfide bonds and alkylation, or by recombinant genetic engineering techniques.

Antibodies are defined to be "immunospecific" if they specifically bind the ligand with an affinity constant, $K_a$, of greater than or equal to about $10^4$ $M^{-1}$, preferably of greater than or equal to about $10^5$ $M^{-1}$, more preferably of greater than or equal to about $10^6$ $M^{-1}$, and still more preferably of greater than or equal to about $10^7$ $M^{-1}$. Affinities of binding partners or antibodies can be readily determined using conventional techniques, for example, those described by Scatchard et al., (*Ann. N.Y. Acad. Sci. USA* 51:660, 1949) or by surface plasmon resonance (BIAcore, Biosensor, Piscataway, N.J.) See, e.g., Wolff et al., *Cancer Res.*, 53:2560-2565, 1993).

Antibodies for use in the present invention may be monospecific, bi-specific, or even tri-specific. In this regard, the antibodies may recognize a single immunogen or may be engineered to recognize two or three different immunogens.

Antibodies may generally be prepared by any of a variety of techniques known to those having ordinary skill in the art (See, e.g., Harlow et al., *Antibodies: A Laboratory Manual*, 1988, Cold Spring Harbor Laboratory). In one such technique, an animal is immunized with the ligand as antigen to generate polyclonal antisera. Suitable animals include rabbits, sheep, goats, pigs, cattle, and may include smaller mammalian species, such as, mice, rats, and hamsters.

An immunogen may be comprised of cells expressing the ligand, purified or partially purified ligand polypeptides or variants or fragments thereof, or ligand peptides. Ligand peptides may be generated by proteolytic cleavage or may be chemically synthesized. Peptides for immunization may be selected by analyzing the primary, secondary, or tertiary structure of the ligand according to methods know to those skilled in the art in order to determine amino acid sequences more likely to generate an antigenic response in a host animal (See, e.g., Novotny, *Mol. Immunol.* 28:201-207, 1991; Berzoksky, *Science* 229:932-40, 1985).

Preparation of the immunogen may include covalent coupling of the ligand polypeptide or variant or fragment thereof, or peptide to another immunogenic protein, such as, keyhole limpet hemocyanin or bovine serum albumin. In addition, the peptide, polypeptide, or cells may be emulsified in an adjuvant (See Harlow et al., *Antiboclies: A Laboratory Manual*, 1988 Cold Spring Harbor Laboratory). In general, after the first injection, animals receive one or more booster immunizations according to a preferable schedule for the animal species. The immune response may be monitored by periodically bleeding the animal, separating the sera, and analyzing the sera in an immunoassay, such as an Ouchterlony assay, to assess the specific antibody titer. Once an antibody titer is established, the animals may be bled periodically to accumulate the polyclonal antisera. Polyclonal antibodies that bind specifically to the ligand polypeptide or peptide may then be purified from such antisera, for example, by affinity chromatography using protein A or using the ligand polypeptide or peptide coupled to a suitable solid support.

Monoclonal antibodies that specifically bind ligand polypeptides or fragments or variants thereof may be prepared, for example, using the technique of Kohler and Milstein (*Nature*, 256:495-497, 1975; *Eur. J. Immunol.* 6:511-519, 1976) and improvements thereto. Hybridomas, which are immortal eukaryotic cell lines, may be generated that produce antibodies having the desired specificity to a the ligand polypeptide or variant or fragment thereof. An animal—for example, a rat, hamster, or preferably mouse—is immunized with the ligand immunogen prepared as described above. Lymphoid cells, most commonly, spleen cells, obtained from an immunized animal may be immortalized by fusion with a drug-sensitized myeloma cell fusion partner, preferably one that is syngeneic with the immunized animal. The spleen cells and myeloma cells may be, combined for a few minutes with a membrane fusion-promoting agent, such as polyethylene glycol or a nonionic detergent, and then plated at low density on a selective medium that supports the growth of hybridoma cells, but not myeloma cells. A preferred selection media is HAT (hypoxanthine, aminopterin, thymidine). After a sufficient time, usually about 1 to 2 weeks, colonies of cells are observed. Single colonies are isolated, and antibodies produced by the cells may be tested for binding activity to the ligand polypeptide or variant or fragment thereof. Hybridomas producing antibody with high affinity and specificity for the ligand antigen are preferred. Hybridomas that produce monoclonal antibodies that specifically bind to a ligand polypeptide or variant or fragment thereof are contemplated by the present invention.

Monoclonal antibodies may be isolated from the supernatants of hybridoma cultures. An alternative method for production of a murine monoclonal antibody is to inject the hybridoma cells into the peritoneal cavity of a syngeneic mouse. The mouse produces ascites fluid containing the monoclonal antibody. Contaminants may be removed from the antibody by conventional techniques, such as chromatography, gel filtration, precipitation, or extraction.

Human monoclonal antibodies may be generated by any number of techniques. Methods include but are not limited to, Epstein Barr Virus (EBV) transformation of human peripheral blood cells (see, U. S. Pat. No. 4,464,456), in vitro immunization of human B cells (see, e.g., Boerner et al., *J. Immunol.* 147:86-95, 1991), fusion of spleen cells from immunized transgenic mice carrying human immunoglobulin genes and fusion of spleen cells from immunized transgenic mice carrying immunoglobulin genes inserted by yeast artificial chromosome (YAC) (see, e.g., U.S. Pat. No. 5,877,397; Bruggemann et al., *Curr. Opin. Biotechnol.* 8:455-58, 1997; Jakobovits et al., *Ann. N.Y. Acad. Sci.* 764:525-35, 1995), or isolation from human immunoglobulin V region phage libraries.

Chimeric antibodies and humanized antibodies for use in the present invention may be generated. A chimeric antibody has at least one constant region domain derived from a first mammalian species and at least one variable region domain derived from a second distinct mammalian species (See, e.g., Morrison et al., *Proc. Natl. Acad. Sci. USA,* 81:6851-55, 1984). Most commonly, a chimeric antibody may be constructed by cloning the polynucleotide sequences that encode at least one variable region domain derived from a non-human monoclonal antibody, such as the variable region derived from a murine, rat, or hamster monoclonal antibody, into a vector containing sequences that encode at least one human constant region. (See, e.g., Shin et al., *Methods Enzymol.* 178:459-76, 1989; Walls et al., *Nucleic Acids Res.* 21:2921-29, 1993). The human constant region chosen may depend upon the effector functions desired for the particular antibody. Another method known in the art for generating chimeric antibodies is homologous recombination (U.S. Pat. No. 5,482,856). Preferably, the vectors will be transfected into eukaryotic cells for stable expression of the chimeric antibody.

A non-human/human chimeric antibody may be further genetically engineered to create a "humanized" antibody. Such an antibody has a plurality of CDRs derived from an immunoglobulin of a non-human mammalian species, at least one human variable framework region, and at least one human immunoglobulin constant region. Humanization may yield an antibody that has decreased binding affinity when compared with the non-human monoclonal antibody or the chimeric antibody. Those having skill in the art, therefore, use one or more strategies to design humanized antibodies.

Within certain embodiments, the use of antigen-binding fragments of antibodies may be preferred. Such fragments include Fab fragments or F(ab')$_2$ fragments, which may be prepared by proteolytic digestion with papain or pepsin, respectively. The antigen binding fragments may be separated from the Fc fragments by affinity chromatography, for example, using immobilized protein A or immobilized ligand polypeptide or a variant or a fragment thereof. An alternative method to generate Fab fragments includes mild reduction of F(ab')$_2$ fragments followed by alkylation (See, e.g., Weir, *Handbook of Experimental Immunology,* 1986, Blackwell Scientific, Boston).

Non-human, human, or humanized heavy chain and light chain variable regions of any of the above described Ig molecules may be constructed as single chain Fv (sFv) fragments (single chain antibodies). See, e.g., Bird et al., *Science* 242: 423-426, 1988; Huston et al., *Proc. Natl. Acad. Sci. USA* 85:5879-5883, 1988. Multi-functional fusion proteins may be generated by linking polynucleotide sequences encoding an sFv in-frame with polynucleotide sequences encoding various effector proteins. These methods are known in the art, and are disclosed, for example, in EP-B1-0318554, U.S. Pat. No. 5,132,405, U.S. Pat. No. 5,091,513, and U.S. Pat. No. 5,476,786.

An additional method for selecting antibodies that specifically bind to a ligand polypeptide or variant or fragment thereof is by phage display (See, e.g., Winter et al., *Annul. Rev. Immunol.* 12:433-55, 1994; Burton et al., *Adv. Immunol.* 57:191-280, 1994). Human or murine immunoglobulin variable region gene combinatorial libraries may be created in phage vectors that can be screened to select Ig fragments (Fab, Fv, sFv, or multimers thereof) that bind specifically to a ligand polypeptide or variant or fragment thereof (See, e.g., U.S. Pat. No. 5,223,409; Huse et al., *Science* 246:1275-81, 1989; Kang et al., *Proc. Natl. Acad. Sci. USA* 88:4363-66, 1991; Hoogenboom et al., *J. Molec. Biol.* 227:381-388, 1992; Schlebusch et al., *Hybridoma* 16:47-52, 1997 and references cited therein).

In certain aspects of the present invention other agents can be used in the generation of EMSP, including but not limited to fusion proteins comprising natural ligands that bind to T cell surface molecules. In one embodiment, fusion proteins can be generated such that Ig Fc portions are fused to a natural ligand of interest. Such a fusion protein could then be loaded onto an EMSP as described herein that expresses an Fcγ receptor.

Cell Populations

As discussed above, the present invention has broad applicability to any cell type having a cell surface moiety that one is desirous of ligating. In this regard, many cell signaling events can be enhanced by the methods of the present invention. Such methodologies can be used therapeutically in an ex vivo setting to activate and stimulate cells for infusion into a patient or could be used in vivo, to induce cell signaling events on a target cell population. However, as also noted above, the prototypic example provided herein is directed to T cells, but is in no way limited thereto.

With respect to T cells, the T cell populations resulting from the various expansion methodologies described herein may have a variety of specific phenotypic properties, depending on the conditions employed. Such phenotypic properties include enhanced expression of CD25, CD154, IFN-γ and GM-CSF, as well as altered expression of CD137, CD134, CD62L, and CD49d. The ability to differentially control the expression of these moieties may be very important. For example, higher levels of surface expression of CD154 on "tailored T cells," through contact with CD40 molecules expressed on antigen-presenting cells (such as dendritic cells, monocytes, and even leukemic B cells or lymphomas), will enhance antigen presentation and immune function. Such strategies are currently being employed by various companies to ligate CD40 via antibodies or recombinant CD40L. The approach described herein permits this same signal to be delivered in a more physiological manner, e.g., by the T cell. The ability to increase IFN-γ secretion by tailoring the T cell activation process could help promote the generation of TH1-type immune responses, important for anti-tumor and anti-viral responses. Like CD154, increased expression of GM-CSF can serve to enhance APC function, particularly through its effect on promoting the maturation of APC progenitors into more functionally competent APC, such as dendritic cells. Altering the expression of CD137 and CD134 can effect a T cell's ability to resist or be susceptible to apoptotic signals. Controlling the expression of adhesion/homing receptors, such as CD62L and/or CD49d may determine the ability of infused T cells to home to lymphoid organs, sites of infection, or tumor sites.

An additional aspect of the present invention provides a T cell population or composition that has been depleted of CD8$^+$ or CD4$^+$ cells prior to expansion. In one embodiment, CD8$^+$ cells are depleted by antibodies directed to the CD8$^+$ marker. One of ordinary skill in the art would readily be able to identify a variety of particular methodologies for depleting a sample of CD8$^+$ or CD4$^+$ cells or conversely enriching the CD4$^+$ or CD8$^+$ cell content. With respect to enriching for CD4+ cells, one aspect of the present invention is focused on the identification of an extremely robust CD154 expression profile upon stimulation of T cell populations wherein $T_C$ (CD8+) cells have been depleted. As indicated above, CD154 is an important immunomodulating molecule whose expression is extremely beneficial in amplifying the immune response. Accordingly an increase in CD154 expression is likely to lead to more efficacious T cell compositions.

An additional aspect of the present invention provides a T cell population or composition that has been depleted or enriched for populations of cells expressing a variety of markers, such as CD62L, CD45RA or CD45RO, cytokines (e.g., IL-2, IFN-γ, IL-4, IL-10), cytokine receptors (e.g., CD25), perforin, adhesion molecules (e.g., VLA-1, VLA-2, VLA-4, LPAM-1, LFA-1), and/or homing molecules (e.g., L-Selectin), prior to expansion. In one embodiment, cells expressing any of these markers are depleted or positively selected by antibodies or other ligands/binding agents directed to the marker. One of ordinary skill in the art would readily be able to identify a variety of particular methodologies for depleting or positively selecting for a sample of cells expressing a desired marker.

The phenotypic properties of T cell populations of the present invention can be monitored by a variety of methods including standard flow cytometry methods and ELISA methods known by those skilled in the art.

T cell populations of the present invention may also be antigen-specific T cells, for example, tumor-antigen-specific T cells or hTERT-specific T cells as described herein. In certain embodiments, antigen-specific T cells can be isolated from a patient of interest, such as a patient afflicted with a cancer or an infectious disease as described herein. In certain embodiments, antigen-specific T cells can be induced by vaccination of a patient with a particular antigen, either alone or in conjunction with an adjuvant or pulsed on dendritic cells.

In certain embodiments, it may be desirable to sort or otherwise positively select the antigen specific cells prior to or following one or two rounds of expansion with EMSP. It may be desirable to sort or positively select cells directly from an individual, for example a patient who has been vaccinated with a particular antigen of interest. In certain embodiments, the activated T cells may have been exposed to an APC pulsed with or expressing an antigen of interest, either naturally in vivo, or through vaccination. Further, in certain embodiments, the specific T cells to be positively selected or otherwise sorted may have been exposed to an APC pulsed with or expressing an antigen of interest in vitro. Sorting or positively selecting antigen-specific cells can be carried out using peptide-MHC tetramers (Altman, et al., *Science*. 1996 Oct. 4; 274(5284):94-6.). In another embodiment antigen-specific T cells are isolated or otherwise positively selected by contacting said T cells with antibodies specific for T cell activation markers. Antibodies that can be used with the methods of the present invention include, but are not limited to, anti-CD25, anti-CD54, anti-CD69, anti-CD38, anti-CD45RO, anti-CD49d, anti-CD40L, anti-CD137, and anti-CD134 antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

Methods of Use

In addition to the methods described above, the EMSP described herein and the cells stimulated and/or activated by the methods herein described may be utilized in a variety of contexts. With respect to the prototypic example of T cells, the methodologies described herein can be used to selectively activate and expand a population expressing any one or more of CD28, CD4, CD8, Bcl-xL, CD45RA, or CD45RO for use in the treatment of infectious diseases and cancer, and generally in immunotherapy. As a result, a phenotypically unique population of T cells, which is polyclonal with respect to antigen reactivity, but essentially homogeneous with respect to either CD4+ or CD8+ can be produced. In addition, the method allows for the expansion of a population of T cells in numbers sufficient to reconstitute an individual's total CD4+ or CD8+ T cell population (the population of lymphocytes in an individual is approximately $3-5\times10^{11}$). The resulting T cell population can also be genetically transduced and used for immunotherapy or can be used in methods of in vitro analyses of infectious agents. For example, a population of tumor-infiltrating lymphocytes can be obtained from an individual afflicted with cancer and the T cells stimulated to proliferate to sufficient numbers. The resulting T cell population can be genetically transduced to express tumor necrosis factor (TNF) or other proteins (for example, any number of cytokines, inhibitors of apoptosis (e.g., Bcl-2), genes that protect cells from HIV infection such as RevM10 or intrakines, and the like, targeting molecules, adhesion and/or homing molecules and any variety of antibodies or fragments thereof (e.g., Scfv)) and given to the individual.

In certain embodiments, the EMSP of the present invention can be contacted with paramagnetic particles such that said paramagnetic particles are engulfed by the EMSP. EMSP comprising paramagnetic particles can then be subjected to magnetic force and concentrated or localized to a particular site of interest, such as a tumor, site of viral infection or site of autoimmune disease, and/or otherwise selected, either in vitro or in vivo.

Likewise, the EMSP of the present invention can be used in vivo or ex vivo to stimulate tumor-specific T cells, autoantigen-specific T cells, and or viral-specific T cells. Within this context, in certain embodiments, the EMSP can be generated such that tolerance to such tumor, auto, or viral antigens is broken, either in an in vivo or in vitro setting. In an in vivo setting, the EMSP can be administered locally to a tumor site, a site of viral infection or site of autoimmune disease, or alternatively can be administered systemically. T cells that have been stimulated using the EMSP as described herein can then be infused into a patient.

One particular use for the CD4+ T cells populations of the invention is the treatment of HIV infection in an individual. Prolonged infection with HIV eventually results in a marked decline in the number of CD4+ T lymphocytes. This decline, in turn, causes a profound state of immunodeficiency, rendering the patient susceptible to an array of life threatening opportunistic infections. Replenishing the number of CD4+ T cells to normal levels may be expected to restore immune function to a significant degree. Thus, the method described herein provides a means for selectively expanding CD4+ T cells to sufficient numbers to reconstitute this population in an HIV infected patient. It may also be necessary to avoid infecting the T cells during long-term stimulation or it may desirable to render the T cells permanently resistant to HIV infection. There are a number of techniques by which T cells may be rendered either resistant to HIV infection or incapable of producing virus prior to restoring the T cells to the infected individual. For example, one or more anti-retroviral agents can be cultured with CD4+ T cells prior to expansion to inhibit HIV replication or viral production (e.g., drugs that target reverse transcriptase and/or other components of the viral machinery, see e.g., Chow et al., *Nature* 361:650-653, 1993).

Several methods can be used to genetically transduce T cells to produce molecules which inhibit HIV infection or replication. For example, in various embodiments, T cells can be genetically transduced to produce transdominant inhibitors, "molecular decoys", antisense molecules, intrakines, or toxins. Such methodologies are described in further detail in U.S. patent application Ser. Nos. 08/253,751, 08/253,964, and PCT Publication No. WO 95/33823, which are incorporated herein by reference in their entirety.

The methods for stimulating and expanding a population of antigen specific T cells are useful in therapeutic situations where it is desirable to up-regulate an immune response (e.g., induce a response or enhance an existing response) upon administration of the T cells to a subject. For example, the method can be used either in vivo or in vitro to enhance a T cell response against tumor-associated antigens. Tumor cells from a subject typically express tumor-associated antigens but may be unable to stimulate a co-stimulatory signal in T cells (e.g., because they lack expression of co-stimulatory molecules). Thus, as described herein tumor cells, or antigen derived therefrom, can be contacted with T cells from the subject in vitro and the resulting tumor-antigen-specific T cells expanded according to the method of the invention and the specific T cells returned to the subject. Additionally, in certain embodiments, it may be desirable to contact T cells with tumor antigen in vivo, e.g., via vaccination. Following vaccination, the specific T cells may be isolated and contacted in vitro and expanded with the EMSP according to the method of the invention. In certain embodiments, the desired antigen-specific T cells can be sorted or isolated using peptide-MHC tetramers or antibodies specific for T cell activation markers. The sorted antigen-specific cells can be further expanded using the methods described herein and returned to the subject. Further, one of ordinary skill in the art would readily understand that treatment of a patient with ex vivo expanded T cells of the present invention may be combined with traditional cancer therapies such as chemotherapy. In this regard, for example, a patient may be treated with an agent such as Fludarabine or Campath (Berlex Laboratories, Montville, N.J., USA), followed by infusion with T cell populations of the present invention.

The present invention thus provides methods for preventing, inhibiting, or reducing the presence of a cancer or malignant cells in an animal, which comprise administering to an animal an anti-cancer effective amount of the subject EMSP with or without activated T cells. Further, as noted above, the EMSP and ativated T cells of the present invention may be combined with traditional cancer therapies.

The cancers contemplated by the present invention, against which the immune response is induced, or which is to be prevented, inhibited, or reduced in presence, may include but are not limited to melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, pancreatic cancer, esophageal cancer, brain cancer, lung cancer, ovarian cancer, cervical cancer, multiple myeloma, hepatocellular carcinoma, nasopharyngeal carcinoma, LGL, ALL, AML, CML, CLL, and other neoplasms known in the art.

Accordingly, in one embodiment malignancies such as non-Hodgkins Lymphoma (NHL) and B-cell chronic lymphocytic leukemia (B-CLL) can be treated. While initial studies using expanded T cells have been tested in NHL, (see Liebowitz et al., *Curr Opin. Onc.* 10:533-541, 1998), the T cell populations of the present invention offer unique phenotypic characteristics that can dramatically enhance the success of immunotherapy by providing increased engraftment (likely supplied by stimulation of the CD28 signal) and reactivity. However, patients with B-CLL present special difficulties, including low relative T cell numbers with high leukemic cell burden in the peripheral blood, accompanied by a general T cell immunosuppression. The T cell populations of the present invention can provide dramatically improved efficacy in treating this disease and especially when combined with stem cell transplantation therapy. Accordingly, increasing T cell function and anti-CLL T cell activity with EMSP would be beneficial.

For example, given that deficient expression of CD154, the ligand for CD40, on T cells of B-CLL patients has been cited as a major immunological defect of the disease, the T cell populations of the present invention, which may provide sustained high levels of CD154 expression upon infusion, could aid in its treatment. Investigators report that in CLL the capability of a patient's T cells' to express CD154 is defective as well as the capability of the leukemic B-cells to express CD80 and CD86. The failure of leukemic B-cells in CLL to adequately express the ligands for CD28, could result in failure to fully activate tumor-responsive T cells and, therefore, may represent the mechanism underlying the T cells' apparent state of tolerance. Studies in which CD40 is engaged on CLL B cells, either via soluble anti-CD40 antibodies or via CD154-transduced leukemic B-cells, appears to correct the defect in CD80 and CD86 expression and up-regulates MHC surface expression. Kato et al., *J. Clin. Invest.* 101:1133-1141, 1998; Ranheim and Kipps, *J. Exp. Med.* 177:925-935, 1993. Cells treated in this way were able to stimulate specific T cell anti-tumor responses.

With the enhanced expression of CD154 on the surface of the T cell population of the present invention such T cells would be expected to interact with autologous B-CLL cells, and would thus increase that tumor's immunogenicity by driving Lip expression of MHC, CD80, and CD86. This, in turn, should lead to a strong anti-tumor response. Further, one of ordinary skill in the art would readily understand that treatment of a patient with ex vivo expanded T cells of the present invention may be combined with traditional cancer therapies such as chemotherapy. In this regard, for example, a patient may be treated with an agent such as Fludarabine or Campath (Berlex Laboratories, Montville, N.J., USA), followed by infusion with T cell populations of the present invention or both.

Compositions as described herein can be used to induce or enhance responsiveness to pathogenic organisms, such as viruses, (e.g., single stranded RNA viruses, single stranded DNA viruses, double-stranded DNA viruses, HIV, hepatitis A, B, and C virus, HSV, CMV, EBV, HPV), parasites (e.g., protozoan and metazoan pathogens such as Plasmodia species, Leishmania species, Schistosoma species, Trypanosoma species), bacteria (e.g., Mycobacteria, Salmonella, Streptococci, *E. coli*, Staphylococci), fungi (e.g., Candida species, Aspergillus species) and *Pneumocystis carinii*.

The invention further provides methods to selectively expand a specific subpopulation of T cells from a mixed population of T cells. In one embodiment, the invention provides specifically enriched populations of T cells that have much higher ratio of CD4+ and CD8+ double positive T cells. In an additional embodiment, the invention provides methods to selectively expand CD8+ T cells expressing increased levels of Bcl-xL.

Another embodiment of the invention, provides a method for selectively expanding a population of $T_{H1}$ cells from a population of CD4+ T cells. In this method, CD4+ T cells are co-stimulated with an anti-CD28 antibody, such as the monoclonal antibody 9.3, inducing secretion of $T_{H1}$-specific cytokines, including IFN-γ, resulting in enrichment of $T_{H1}$ cells over $T_{H2}$ cells. In a further embodiment, methods are provided for selectively expanding Tc1 over Tc2 cells, or vice versa. Tc1 and Tc2 cells can be distinguished based on cytokine secretion patterns using any number of assays known to the skilled artisan.

T cells have been demonstrated to be activated within a few hours (Iezzi et al., *Immunity* 8:89-95, 1998). Accordingly, in combination with the methodologies herein described, this provides the ability to expand a tailor made subset of a T cell population in a short period of time. In one embodiment, this technique can be utilized at the bedside of a subject, in an outpatient modality, or at a subject's home, similar to the use of kidney dialysis. For example, a method or device wherein T cells are incubated in contact with activation signals (e.g., anti-CD3 and anti-CD28 antibodies, and the like) and returned to the patient immediately in a continuous flow or after a few hour expansion period. In one aspect, such techniques of expansion could use isolated chambers with filter components, such that EMSP are mixed with a continuous flow of blood/concentrated cells. In another embodiment, EMSP within an apparatus may be provided to stimulate T cell activation and expansion. For example, a continuous fluid path from the patient through a blood/cell collection device and/or a disposable device containing EMSP and/or other components to stimulate T cells prior to cells returning to the subject can be utilized. Such a system could involve a leukapheresis instrument with a disposable set sterile docked to the existing manufacturers disposable set, or be an adaptation to the manufacturer's disposable set. Further, the EMSP may be a part of a removal insert which is inserted into one of the device chambers or physically present within one of the disposable components. In another embodiment of the continuous flow aspect discussed above, the system may comprise contacting the cells with the activating components at room temperature or at physiologic temperature using a chamber within a blood collection device or an incubation chamber set up in series with the flow path to the patient.

In another example, blood is drawn into a stand-alone disposable device directly from the patient that contains EMSP. In one embodiment, the disposable device may comprise a container (e.g., a plastic bag, or flask) with appropriate tubing connections suitable for combining/docking with syringes and sterile docking devices. This device will contain a EMSP for immobilization of T cell activation components (e.g., anti-CD3 and anti-CD28 antibodies); Additionally when using the stand-alone device, the subject can remain connected to the device, or the device can be separable from the patient. Further, the device may be utilized at room temperature or incubated at physiologic temperature using a portable incubator.

As devices and methods for collecting and processing blood and blood products are well known, one of skill in the art would readily recognize that given the teachings provided herein, that a variety of devices that fulfill the needs set forth above may be readily designed or existing devices modified. Accordingly, as such devices and methods are not limited by the specific embodiments set forth herein, but would include any device or methodology capable of maintaining sterility and which maintains blood in a fluid form in which complement activation is reduced and wherein components necessary for T cell activation (e.g., anti-CD3 and anti-CD28 antibodies or ligands thereto) may be separated from the blood or blood product prior to administration to the subject. Further, as those of ordinary skill in the art can readily appreciate a variety of blood products can be utilized in conjunction with the devices and methods described herein. For example the methods and devices could be used to provide rapid activation of T cells from cryopreserved whole blood, peripheral blood mononuclear cells, other cyropreserved blood-derived cells, or cryopreserved T cell lines upon thaw and prior to subject administration. In another example, the methods and devices can be used to boost the activity of a previously ex vivo expanded T cell product or T cell line prior to administration to the subject, thus providing a highly activated T cell product. Lastly, as will be readily appreciated the methods and devices above may be utilized for autologous or allogeneic cell therapy simultaneously with the subject and donor.

The methods of the present invention may also be utilized with vaccines to enhance reactivity of the antigen and enhance in vivo effect. Further, given that T cells expanded by the present invention have a relatively long half-life in the body, these cells could act as perfect vehicles for gene therapy, by carrying a desired nucleic acid sequence of interest and potentially homing to sites of cancer, disease, or infection. Accordingly, the cells expanded by the present invention may be delivered to a patient in combination with a vaccine, one or more cytokines, one or more therapeutic antibodies, or in combination with the EMSP as described herein. Virtually any therapy that would benefit by a more robust T cell population is within the context of the methods of use described herein.

In a further embodiment of the present invention, EMSP may be used to expand antigen-specific T cells. In this regard, any number of sources of antigen-specific T cells can be used. In certain embodiments, tumor-specific T cells can be isolated from a cancer patient. In certain embodiments, the antigen-specific T cells are induced by vaccination of a patient with a particular antigen, either alone or in conjunction with an adjuvant or pulsed on dendritic cells. In one embodiment, tumor-specific T cells can be expanded in vivo using the EMSP of the present invention, either alone, or following vaccination with an antigen of interest. In certain embodiments, the EMSP can be pulsed with or modified to express an antigen of interest.

Antigen-specific cells for use in expansion using the EMSP of the present invention may also be generated in vitro using any number of methods known in the art, for example, as described in U.S. Patent Application No. 60/469,122 entitled GENERATION AND ISOLATION OF ANTIGEN-SPECIFIC T CELLS, filed May 8, 2003, or in U.S. Pat. Nos. 6,040,177 and 5,872,642. Antigen-specific cells for use in expansion using the EMSP of the present invention may also be generated using any number of methods known in the art, for example, as described in Current Protocols in Immunology, or Current Protocols in Cell Biology, both published by John Wiley & Sons, Inc., Boston, Mass. In a related embodiment, it may be desirable to sort the antigen specific cells prior to, or even following one or two rounds of expansion with EMSP. Sorting of antigen-specific cells can be carried out using peptide-MHC tetramers as described herein or antibodies specific for any number of markers of memory T cells (including but not limited to, anti-CD25, anti-CD54, anti-CD69, anti-CD38, anti-CD45RO, anti-CD49d, anti-CD40L, anti-CD137, and anti-CD134 antibodies). Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

As noted elsewhere herein, the cell compositions of the present invention comprising EMSP and/or activated T cells can be used in conjunction with other cancer therapies, including but not limited to chemotherapy, radiation, or treatment with agents such as cyclosporin, azathioprine, methotrexate, mycophenolate, and FK506, antibodies, or other immunoablative agents such as CAMPATH, anti-CD3 antibodies, cyclophosphamide, fludaribine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993; Isoniemi (supra)). Further, the compositions of the present invention comprising EMSP and/or activated T cells can be used in conjunction with other treatment modalities, e.g., any treatments desirable in the setting of any of the infectious diseases described herein, such as antiviral, antibacterial, or anti fungal agents.

Pharmaceutical Compositions

The EMSP and/or the target cell populations, such as T cell populations of the present invention may be administered either alone, or as a pharmaceutical composition in combination with diluents and/or with other components such as IL-2 or other cytokines or cell populations. Briefly, pharmaceutical compositions of the present invention may comprise an EMSP or a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The present invention also provides methods for preventing, inhibiting, or reducing the presence of a cancer or malignant cells in an animal, which comprise administering to an animal an anti-cancer effective amount of the subject EMSP with or without activated T cells.

The cancers contemplated by the present invention, against which the immune response is induced, or which is to be prevented, inhibited, or reduced in presence, may include but are not limited to melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, pancreatic cancer, esophageal cancer, brain cancer, lung cancer, ovarian cancer, cervical cancer, multiple myeloma, hepatocellular carcinoma, nasopharyngeal carcinoma, ALL, AML, CML, CLL, and other neoplasms known in the art.

Alternatively, compositions as described herein can be used to induce or enhance responsiveness to pathogenic organisms, such as viruses, (e.g., single stranded RNA viruses, single stranded DNA viruses, double-stranded DNA viruses, HIV, hepatitis A, B, and C virus, HSV, CMV, EBV, HPV), parasites (e.g., protozoan and metazoan pathogens such as Plasmodia species, Leishmania species, Schistosoma species, Trypanosoma species), bacteria (e.g., Mycobacteria, Salmonella, Streptococci, *E. coli*, Staphylococci), fungi (e.g., Candida species, Aspergillus species) and *Pneumocystis carinii*.

The immune response induced in the animal by administering the subject compositions of the present invention may include cellular immune responses mediated by $CD8^+$ T cells, capable of killing tumor and infected cells, and $CD4^+$ T cell responses. Humoral immune responses, mediated primarily by B cells that produce antibodies following activation by $CD4^+$ T cells, may also be induced. A variety of techniques may be used for analyzing the type of immune responses induced by the compositions of the present invention, which are well described in the art; e.g., Coligan et al., *Current Protocols in Immunology*, John Wiley & Sons Inc., 1994.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient. It can generally be stated that a pharmaceutical composition comprising the subject EMSP and/or activated T cells, may be administered at a dosage to be determined during appropriate clinical trials. EMSP compositions may also be administered multiple times at these dosages. The cells can be administered by using infusion techniques that are commonly known in immunotherapy (see, e.g., Rosenberg et al., *New Eng. J. of Med.* 319:1676, 1988). The optimal dosage and treatment regime for a particular patient can readily be determined by one skilled in the art of medicine by monitoring the patient for signs of disease and adjusting the treatment accordingly.

Activated T cells will be administered in dosages and routes and at times to be determined in appropriate clinical trials. T cell compositions may be administered multiple times at dosages within these ranges. The EMSP-based method of therapy may be combined with other methods, such as direct administration of the activated T cells of the invention. The activated T cells and EMSP may be autologous or heterologous to the patient undergoing therapy. If desired, the treatment may also include administration of mitogens (e.g., PHA) or lymphokines, cytokines, and/or chemokines (e.g., GM-CSF, IL-4, IL-13, Flt3-L, RANTES, MIP1-α, etc.) as described herein to enhance induction of the immune response.

The administration of the subject pharmaceutical compositions may be carried out in any convenient manner, including by aerosol inhalation, injection, ingestion, transfusion, implantation or transplantation. The compositions of the present invention may be administered to a patient subcutaneously, intradermally, intramuscularly, by intravenous (i.v.) injection, or intraperitoneally. Preferably, the EMSP compositions of the present invention are administered to a patient by intradermal or subcutaneous injection. The T cell compositions of the present invention are preferably administered by i.v. injection. The compositions of EMSP or activated T cells may be injected directly into a tumor or lymph node.

In yet another embodiment, the pharmaceutical composition can be delivered in a controlled release system. In one embodiment, a pump may be used (see Langer, *Science* 249: 1527-33, 1990; Sefton, *CRC Crit. Ref. Biomed. Eng.* 14:201, 1987; Buchwald et al., i Surgery 88:507, 1980; Saudek et al., *N. Engl. J. Med.* 321:574, 1989). In another embodiment, polymeric materials can be used (see Langer and Wise (eds.), *Medical Applications of Controlled Release*, CRC Pres., Boca Raton, Fla., 1974; Smolen and Ball (eds.), *Controlled Drug Bioavailability*, "Drug Product Design and Performance," Wiley, N.Y., 1984; Ranger and Peppas, *J. Macromol. Sci. Rev. Macromol. Chem.* 23:61, 1983; see also Levy et al., *Science* 228:190 1985; During et al., *Ann. Neurol.* 25:351, 1989; Howard et al., *J. Neurosurg.* 71:105, 1989). In yet another embodiment, a controlled release system can be placed in proximity of the therapeutic target, thus requiring only a fraction of the systemic dose (see, e.g., Langer and Wise (eds.), *Medical Applications of Controlled Release*, CRC Pres., Boca Raton, Fla., 1984, vol. 2, pp. 115-138).

The EMSP and T cell compositions of the present invention may also be administered using any number of matrices. Matrices have been utilized for a number of years within the context of tissue engineering (see, e.g., Lanza, Langer, and Chick (eds.), *Principles of Tissue Engineering*, 1997). The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

In one aspect of the present invention, the EMSP described herein can be used in vivo as an adjuvant as described in U.S. Pat. No. 6,464,973. In a further embodiment, the EMSP can be used as a vaccine to induce an immune response in vivo against an antigen of interest such as those described herein (e.g., tumor antigens, viral antigens, autoantigens, etc). In one embodiment the EMSP can be used to generate an immune response in vivo, either administered alone or in combination with activated T cells as described herein or in combination with other known therapies.

In one embodiment of the present invention, EMSP may be used to generate polyclonal and/or antigen-specific T cells in vitro or in vivo. T cells may be stimulated with EMSP loaded or engineered to express antigen in the context of MHC as previously described. Such stimulation is performed under conditions and for a time sufficient to permit the generation of T cells that are specific for the antigen of interest. For example, T cells ($5 \times 10^6$ cells/ml) and antigen-loaded or expressing EMSP ($2.5 \times 10^5$ cells/ml) may be cultured in conventional media as described herein, supplemented with 5-10% serum, 1 mM sodium pyruvate, with or without 100 IU/ml penicillin, with or without 100 µg/ml streptomycin, and $5 \times 10^{-5}$ M β-mercaptoethanol in 96 well U-bottom plates at a ratio of 20:1. After 5 days, cells may be tested for antigen-specificity in a standard 4 hours chromium release assay. Antigen-specific T cells may be further expanded using techniques known in the art (as described in U.S. Pat. No. 5,827, 642) or as described herein. Stimulation of T cells with EMSP as described in the Examples may be carried out following the stimulation with antigen-loaded EMSP to further increase expansion of the desired antigen-specific T cells.

All references referred to within the text are hereby incorporated by reference in their entirety. Moreover, all numerical ranges utilized herein explicitly include all integer values within the range and selection of specific numerical values within the range is contemplated depending on the particular use. Further, the following examples are offered by way of illustration, and not by way of limitation.

EXAMPLES

Protocols

The constructions described below are carried out according to the general techniques of genetic engineering and molecular cloning detailed in, e.g., Maniatis et al., (*Laboratory Manual*, Cold Spring Harbor, Laboratory Press, Cold Spring Harbor, N.Y. (1989)). The steps of PCR amplification follow known protocols, as described in, e.g., *PCR Protocols-A Guide to Methods and Applications* (ed., Innis, Gelfand, Sninsky and White, Academic Press Inc. (1990)). Notably, the oligonucleotides used to modify the Ad genome may use different restriction enzyme sites than those identified below, and may use a slightly different insertion site in the genome, without affecting the outcome of the invention. Such variations, so long as not substantial, are within the understanding of one of ordinary skill in the art.

Moreover, cells are transfected according to standard techniques, well known to a person skilled in the art. Protocols enabling a nucleic acid to be introduced into a cell may employ known methods, e.g., calcium phosphate transfection (Maniatis et al., 1989), DEAE-dextran techniques, electroporation, methods based on osmotic shocks, micro-injection of the selected cell, or methods based on the use of liposomes.

Cloning and construction of cell-based artificial APC (aAPC). Human CD32 was cloned from neutrophils into the pcDNA 3.1 neo vector (Invitrogen, Carlsbad, Calif.), and transfected into K562 cells (American Type Culture Collection, Manassas, Va.) by electroporation; K32 cells were cloned by FACS sorting. Similarly, (h)4-1BB ligand was cloned from B cells into the pcDNA3.1 hygro vector (Invitrogen), and transfected into K32 cells before FACS sorting.

CD8$^+$ T lymphocyte preparation and K562 cell culture. Fresh peripheral blood lymphocytes were obtained by leukopheresis and elutriation. CD4$^+$ T cells were purified by negative selection using the OKT4 Ab (ATCC) as described by June et al., *Mol. Cell Biol.* 7:4472-4481 (1987). (Ab=antibodies; mAb=monoclonal antibodies). CD8$^+$ T cells were purified identically, but OKT8 Ab (ATCC) was substituted for the OKT4 Ab. All cultures were maintained in AIM V (GIBCO BRL, Life Technologies, Grand Island, N.Y.) with 3% human AB serum (BioWhittaker, Walkersville, Md.). Human IL-2 (Chiron Therapeutics, Emeryville, Calif.) was added at 20 IU/mL where indicated.

T lymphocyte stimulation and long-term culture. At each time point at which the lymphocytes were stimulated, the K562 cell-based aAPCs were irradiated with 10,000 rads, then washed twice into T cell culture medium. Cell-based aAPCs were then loaded with anti-CD3 (OKT3) and anti-CD28 mAbs (9.3) at 0.5 µg/ml for 10 minutes at room temperature. Unwashed, antibody-loaded aAPCs were then mixed with CD8$^+$ T cells at a 1:2 K562:T cell ratio. The T cell concentration was maintained at $0.5 \times 10^6$ cells/ml throughout culture, and up to $100 \times 10^6$ T cells were maintained in flasks. Anti-CD3/28 bead stimulation was performed as previously described by Levine et al., *J. Immunol.* 159:5921-5930 (1997). Cultured T cells were monitored for cell volume and enumerated on a Coulter Multisizer II (Miami, Fla.) every 2-3 days, and re-stimulated at 7-10 day intervals when the mean lymphocyte volume reached 200-250 fL.

Flow cytometry and FACS sorting. Cells were stained with antibodies (and/or MHC tetramers) at 4° C., and analyzed on a FACSCalibur™ (BD BioSciences, Mountain View, Calif.). Apoptosis assays were conducted per the manufacturer's protocol (R & D Systems, Minneapolis, Minn.). Cell sorting was performed on a MoFlo® cell sorter (Cytomation, Fort Collins, Calif.). All flow cytometry data were analyzed with FlowJo software (TreeStar, San Carlos, Calif.).

Real-time PCR and TCR Vβ repertoire analysis. Real time PCR was performed and normalized to 28s rRNA levels as described previously by Riley et al., *J. Immunol.* 166, 4943-4948 (2001). The diversity of TCR Vβ repertoire was assessed by determination of CDR3 size lengths by multiplex PCR as previously described by Claret et al., *J. Clin. Invest.* 100:855-866 (1997).

$^{51}$Cr release assays. Target T2 cells (ATCC) were pulsed with 10 µM flu peptide (see Maus et al., 2002) or left unpulsed before labeling with $^{51}$chromium (PerkinElmer Life Sciences, Inc., Boston Mass.). After a four-hour incubation of effectors with targets, radioactivity was counted from an aliquot of supernatant. Specific lysis was calculated by standard methods.

After a four-hour incubation of effectors with targets, radioactivity was counted from an aliquot of supernatant. Specific lysis was calculated by standard methods.

Example 1

Construction of Artificial APCs (aAPCs)

A cell-based aAPC was designed which could be genetically manipulated to express different co-stimulatory molecules in addition to CD28. K562 cells were chosen because they do not express HLA proteins that would promote allogeneic responses, but they do express the T cell interaction molecules ICAM (CD54) and LFA-3 (CD58) (FIG. 1A). K562 cells expressing the human Fcγ receptor CD32 (K32 cells) were transfected and then cloned to permit exogenous loading of anti-CD3 and anti-CD28 antibodies (FIG. 1A). Similarly, the K32/4-1BBL line (FIGS. 1A, B) was generated by transfecting K32 cells with human 4-1BB ligand. Cultures were initiated by adding γ-irradiated aAPCs to fresh human CD8$^+$ T cells prepared by negative selection as described.

Figure 1C:
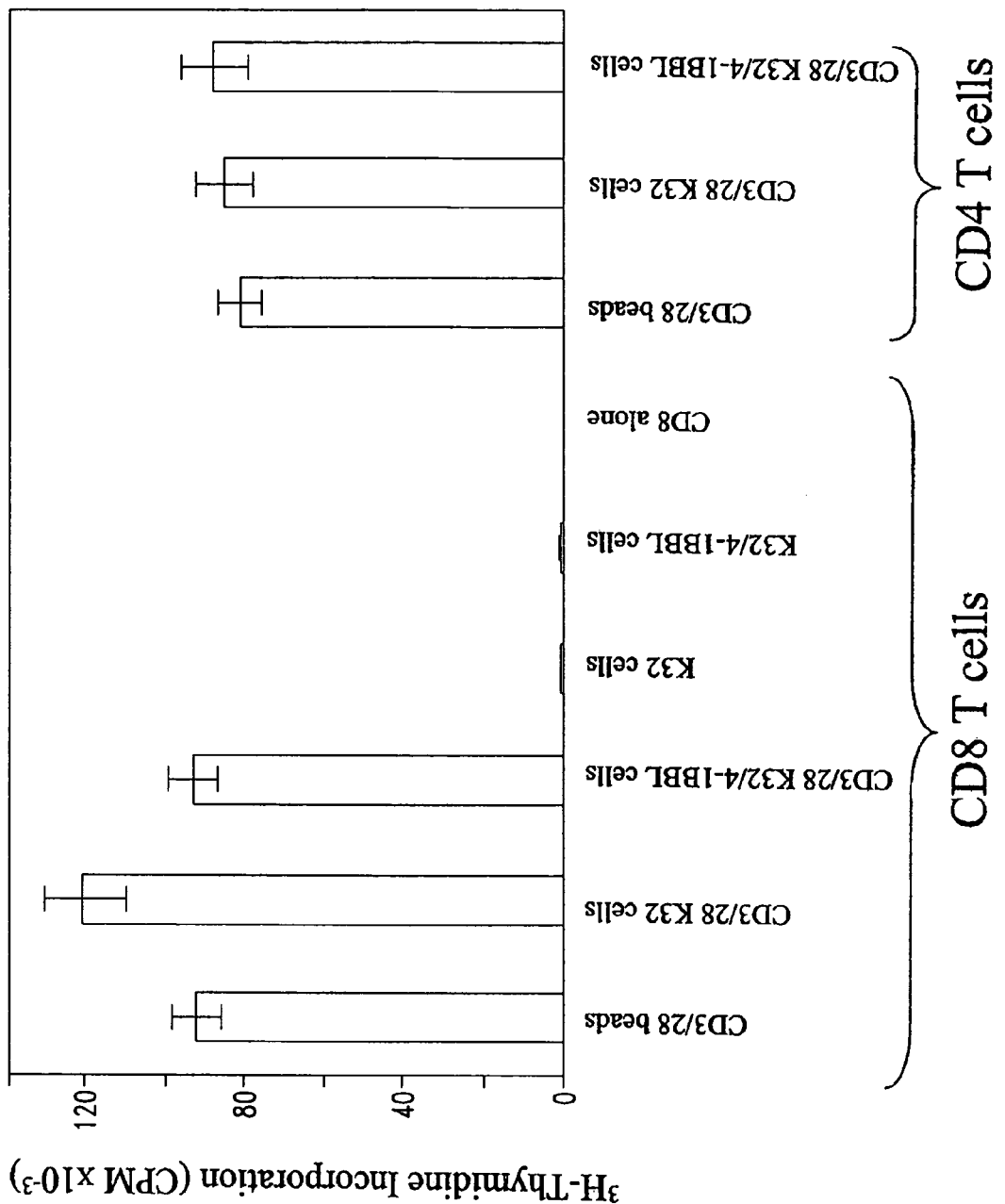

K32 and K32/4-1BBL aAPCs efficiently activate human polyclonal CD8$^+$ T cells. The aAPCs were tested for their ability to stimulate the initial activation and proliferation of primary CD8$^+$ T cells. The T cells were stimulated with three different preparations of aAPCs: CD3/28 beads, K32 cells coated with anti-CD3 and anti-CD28 (K32/CD3/28), or K32/4-1BBL cells coated with the same antibodies (K32/4-1BBL/CD3/28). The initial rate of growth of the T cells stimulated with all three aAPCs was equivalent, as judged by thymidine incorporation (FIG. 1C). This observation was confirmed by labeling fresh T cells with carboxyfluorescein diacetate succinimidyl ester (CFSE) and tracking cell division during the first five days of culture (data not shown). The K562 cell-based system was found to be equivalent to CD3/28 beads for the induction of proliferation and cell division of CD4$^+$ T cells (FIG. 1C and data not shown). Neither K562-based aAPCs, nor CD8$^+$ T cells, nor CD4$^+$ T cells incubated separately showed any proliferation (FIG. 1C and data not shown). Thus, the requirements for the initial rounds of CD8$^+$ T cell proliferation were satisfied equally by CD3/CD28 stimulation provided in the context of polystyrene beads or cell based aAPCs, and the addition of 4-1BBL co-stimulation did not appear to have further benefit.

Example 2

K32/4-1BBL aAPCs Permit Long-Term Expansion of Human Polyclonal CD8$^+$ T Cells

Figure 2A:
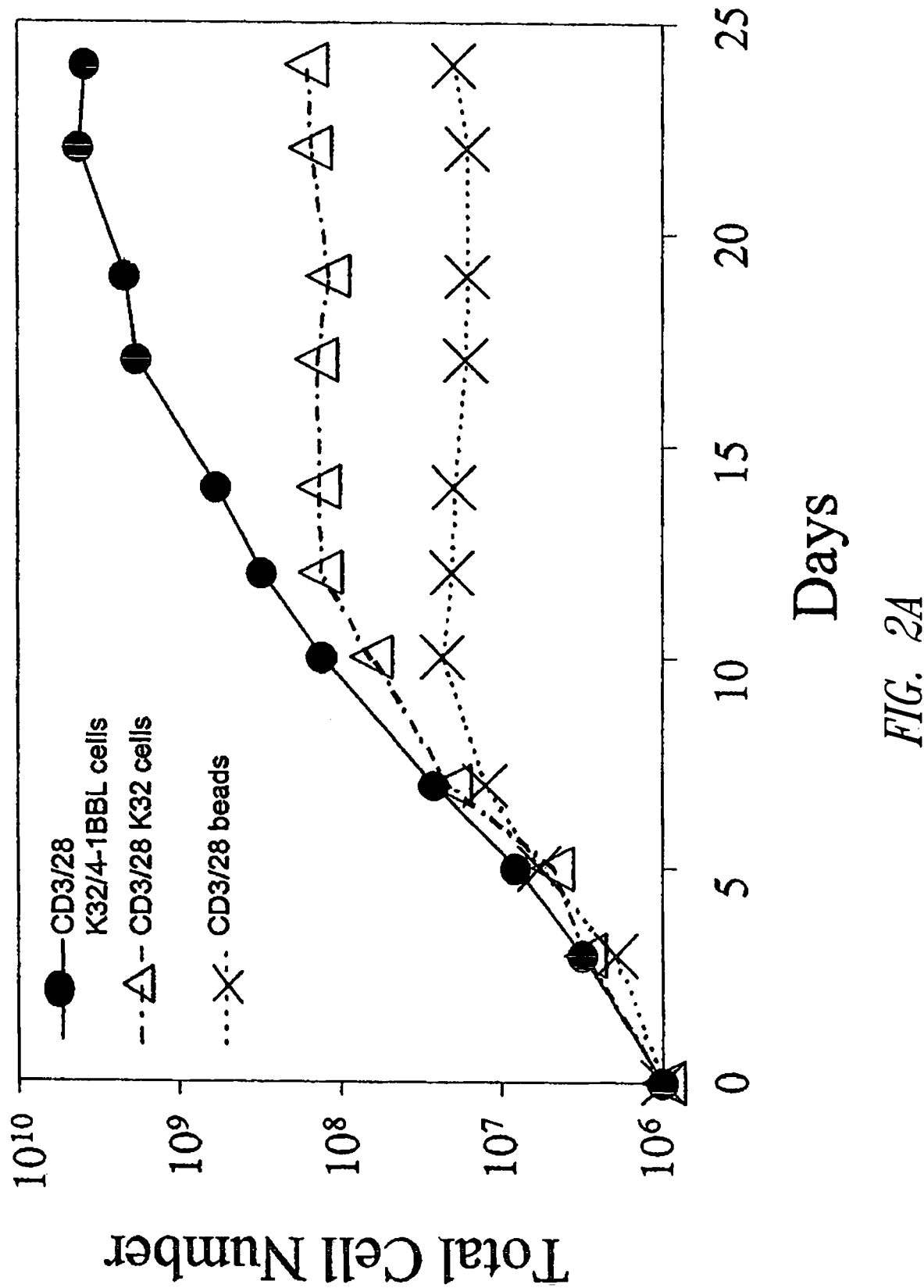
FIGS. 2A-2C depict long-term growth of primary polyclonal human CD8+ T cells stimulated with aAPCs in the absence of exogenous cytokines.

Next, to determine whether the aAPC were sufficient to maintain long term propagation of CD8$^+$ T cells (FIG. 2A) CD8$^+$ T cells were stimulated with aAPCs—but no exogenous cytokines were added to the medium. CD3/28 bead-stimulated cells failed to proliferate after the second stimulation with aAPCs, in agreement with previous findings. Similarly, CD8$^+$ T cells stimulated with CD3/28 in the context of K32 cells entered into a plateau phase of the growth curve within 2 weeks of culture, and no additional net growth of cells occurred after re-stimulation.

In contrast, when CD8$^+$ T cell cultures were stimulated with K32/4-1BBL/CD3/28 aAPCs, they remained in exponential growth even after a third stimulation. This augmentation of long-term proliferation was reproducible, as the average increase in the total number of T cells was 410-fold higher in cultures stimulated with K32/4-1BBL/CD3/28 than in cultures stimulated with CD3/28 beads in six independent experiments.

Figure 2B:
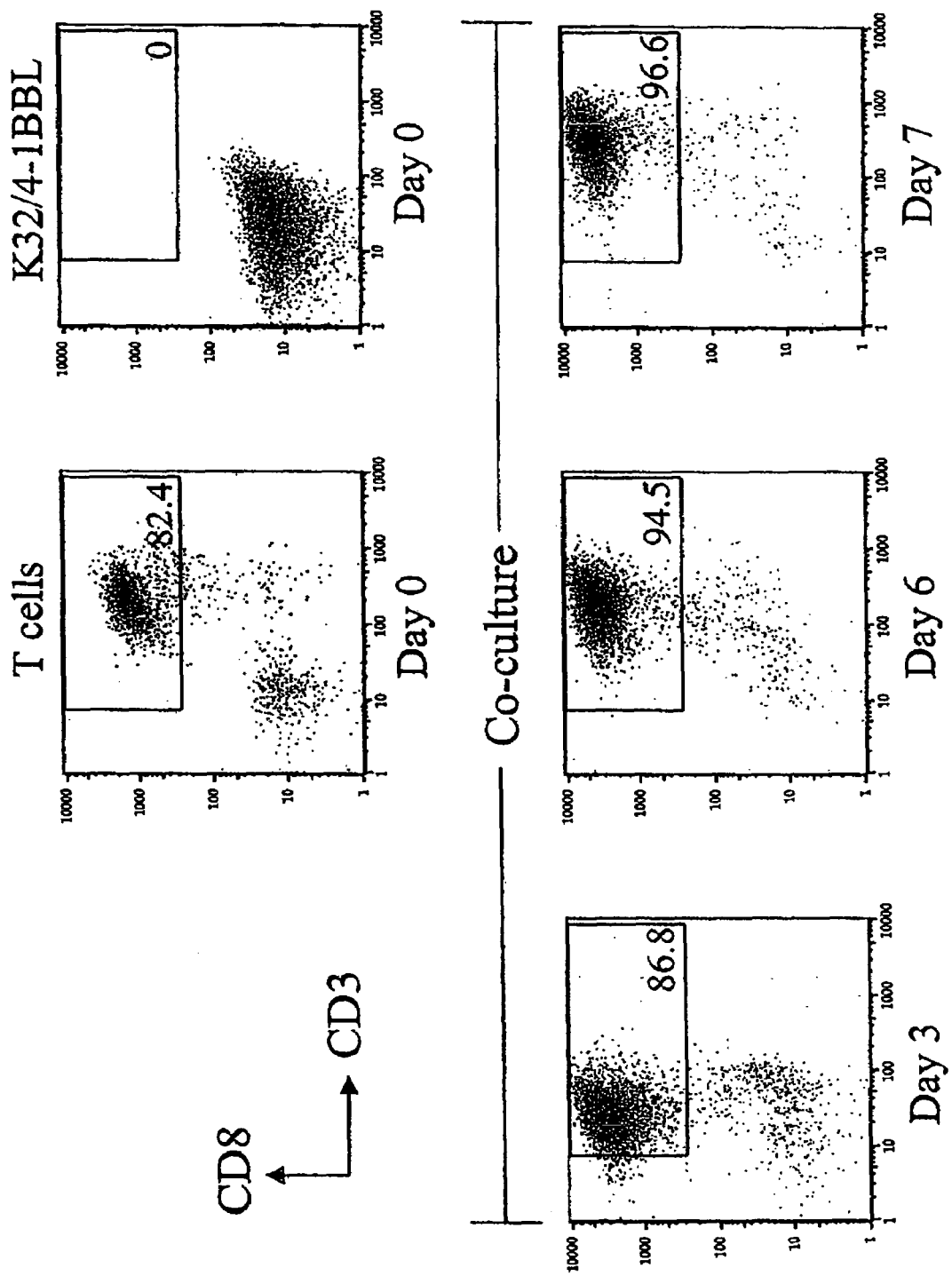
Figure 2C:
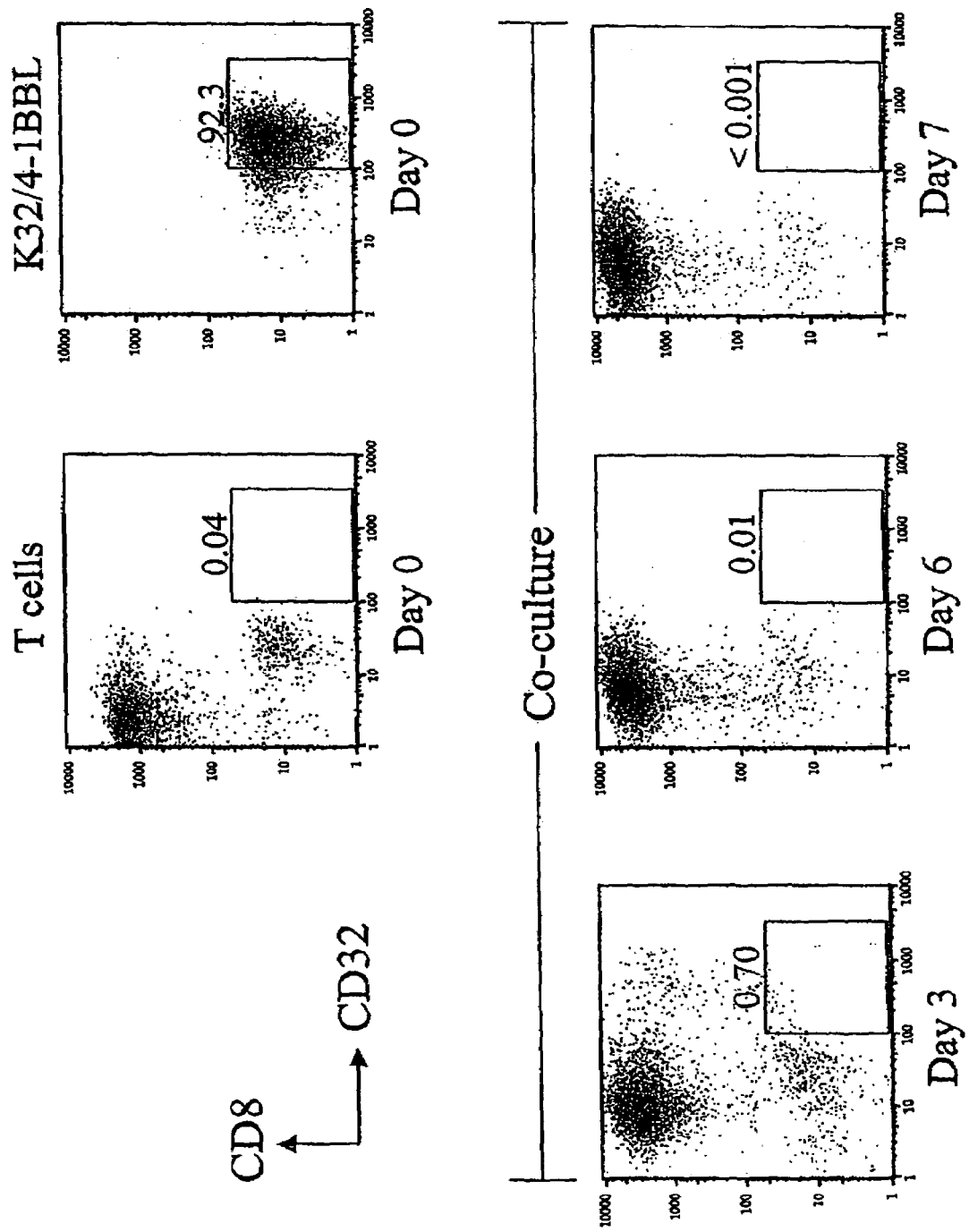

Phenotypic analysis of cultures showed a progressive enrichment for CD3$^+$CD8$^+$ T cells after stimulation with K32/4-1BBL/CD3/28 aAPCs (FIG. 2B). The cell based aAPCs rapidly disappeared from the cell culture, as evidenced by an inability to detect the irradiated K32/4-1BBL cells by flow cytometry after seven days (FIG. 2C). This finding was confirmed in large-scale experiments and also by RT-PCR for CD32 (data not shown). Thus, the mixed T cell and aAPC culture yields a population of essentially pure T cells within one week.

Example 3

Figure 3A:
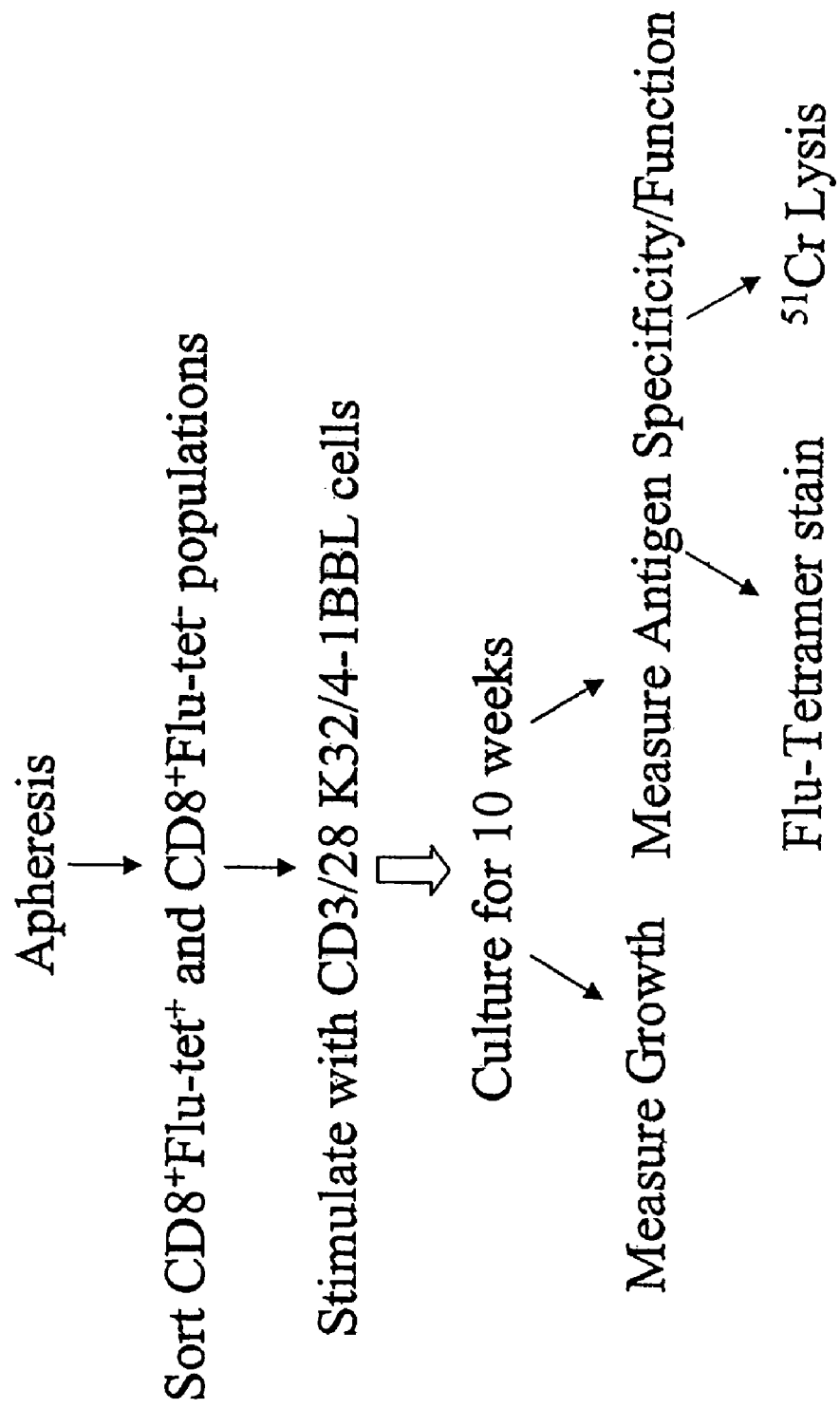
FIGS. 3A-3D depict propagation of antigen-specific cytotoxic T cells from an HLA A*0201 donor using K32/4-1BBL aAPCs.

Efficient Propagation of Antigen-Specific Cytotoxic T Cells by K32/4-1BBL aAPCs In certain embodiments, immunotherapy with $CD8^+$ T cells will likely require cells with antigen-specific cytolytic functions. Therefore, it was necessary to determine whether the K32/4-1BBL aAPCs could be used to expand antigen-specific CTLs, although antigens are not essential in the presentation of the aAPCs. Consequently, they were used to culture a population of MHC tetramer⁻ sorted primary $CD8^+$ T cells for 10 weeks (FIG. 3A). Purified $CD8^+$ T cells obtained from an HLA-A*0201 donor were stained and sorted with an A*0201 MHC tetramer loaded with a flu matrix protein peptide (flu MP tetramer). The tetramer$^+$ population was present at an initial frequency of 0.081% (FIG. 3B), which presumably was composed mainly of memory T cells. Cultures of tetramer $CD8^+$ T cells served as an internal control population of T cells to assess the growth potential and specificity of the tetramer$^+$ population of $CD8^+$ T cells.

Figure 3B:
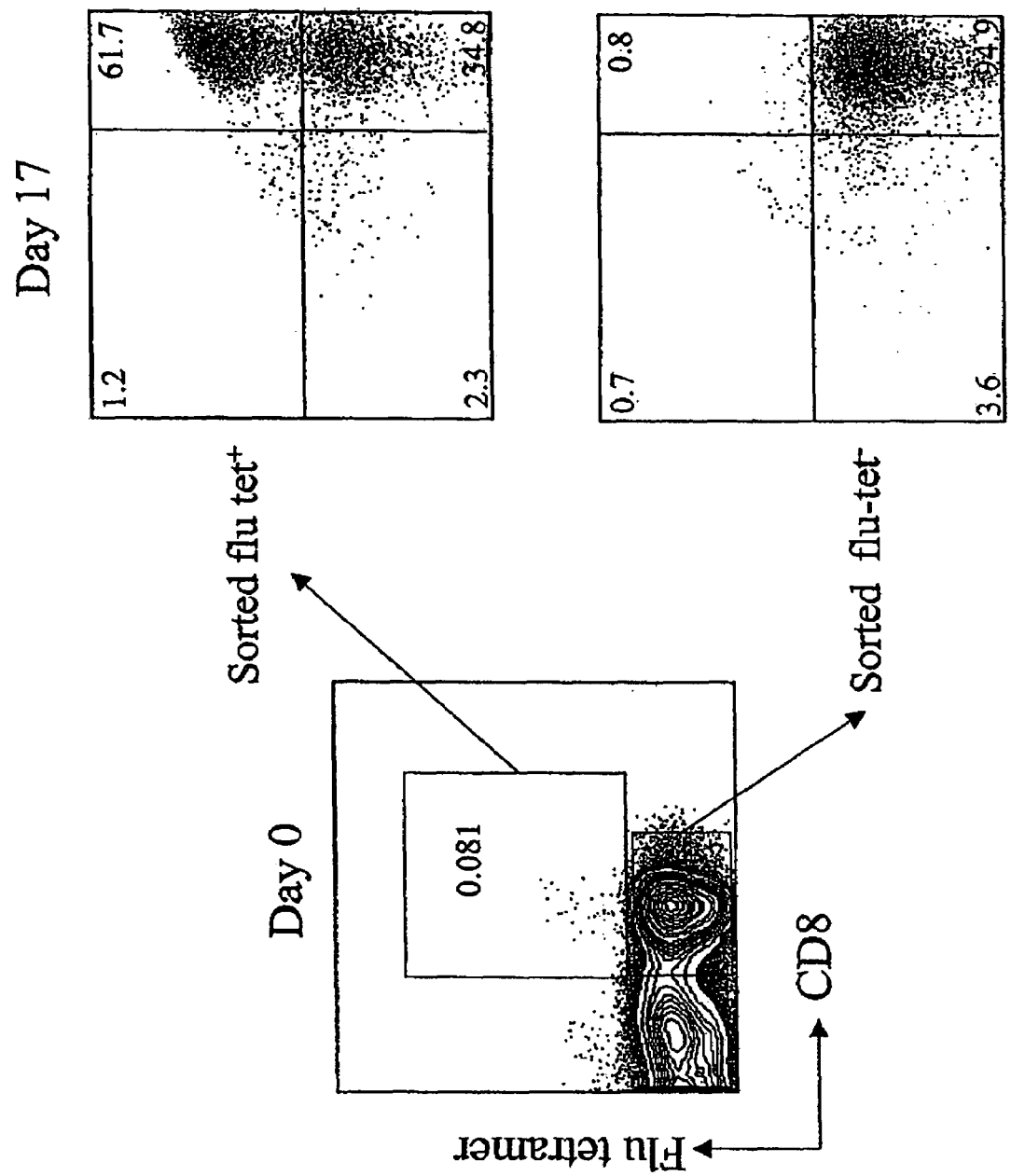
Figure 3C:
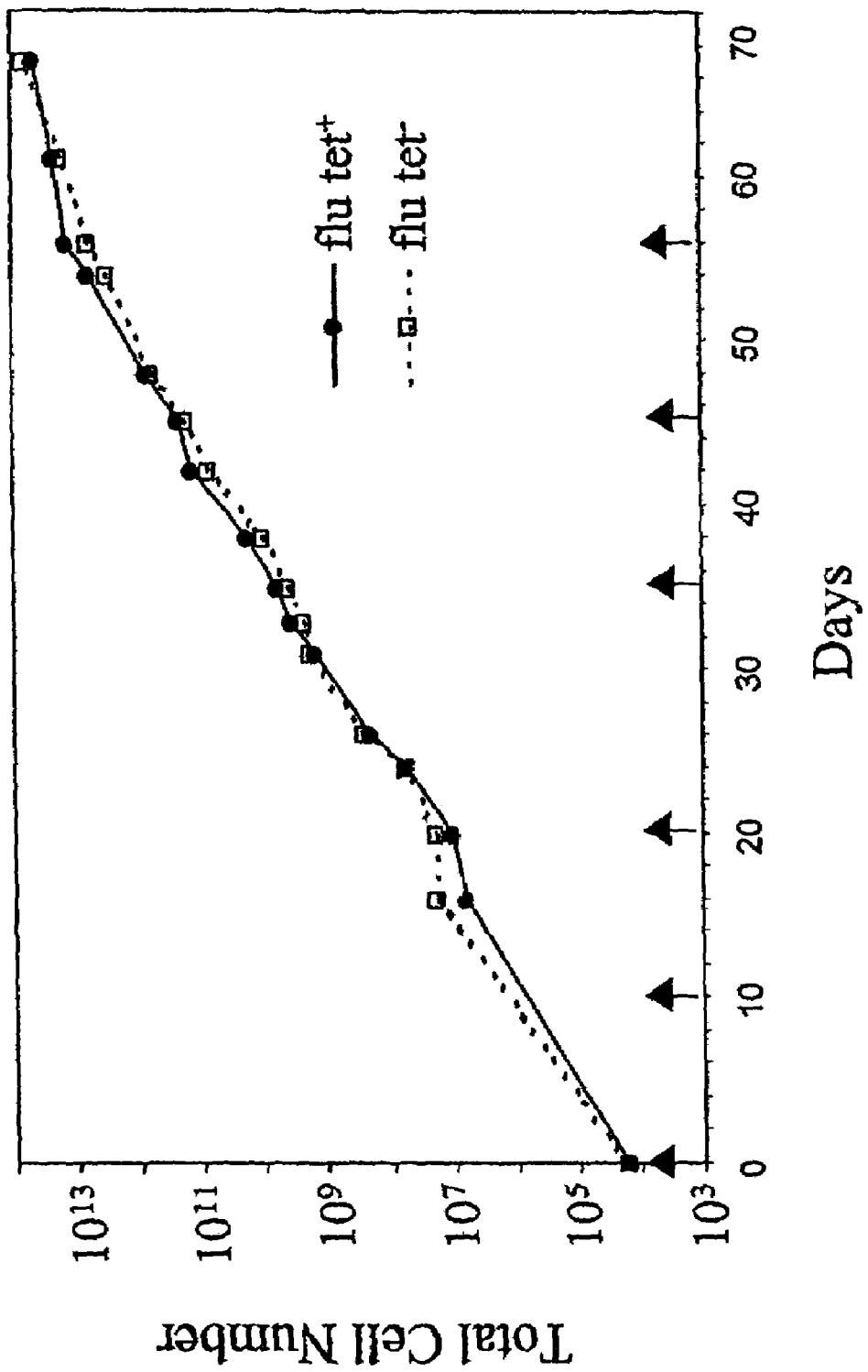

After bulk sorting, 16,000 cells each of $CD8^+$fluMP-tetramer$^+$ and tetramer$^-$ phenotype were stimulated with irradiated K32/4-1BBL/CD3/28 aAPCs (FIG. 3C). All cells were re-stimulated with K32/4-1BBL aAPCs at ~10 day intervals and rhIL-2 (20 IU/mL) was added to the culture during the 4$^{th}$ week. No specific flu stimulation was provided during culture. Exponential growth curves of both populations of cells were obtained for several months. The 16,000 antigen-specific T cells yielded $1.5 \times 10^9$ cells after one month of culture, a number of cells sufficient for immunotherapy. The substantial proliferative capacity of the $CD8^+$ T cells that remained after 30 days of culture indicated that these CTLs could have substantial long-term engraftment potential after adoptive transfer.

To determine if antigen specificity of the expanded populations was maintained during culture, cells were stained with flu MP tetramer (FIG. 3B). On day 17, the population that was initially sorted as flu MP tetramer$^+$ was 61.7% $CD8^+$flu MP tetramer$^+$, while the population that was sorted as flu MP tetramer$^-$ had negligible staining. The percentage of tetramer$^+$ cells in culture declined somewhat over time, but remained at >20% through day 60 (data not shown).

Similar results were obtained with T cells from another HLA A*0201 donor, where on day 26 of culture, the population sorted as flu MP tetramer$^+$ was 49% $CD8^+$ flu MP tetramer$^+$ and again remained at >20% through day 60 (data not shown). Thus, a single round of selection for $CD8^+$ cells with the desired specificity is sufficient to maintain acceptable purity of $CD8^+$ cells cultured on K32/4-1BBL/CD3/28 aAPCs.

Figure 3D:
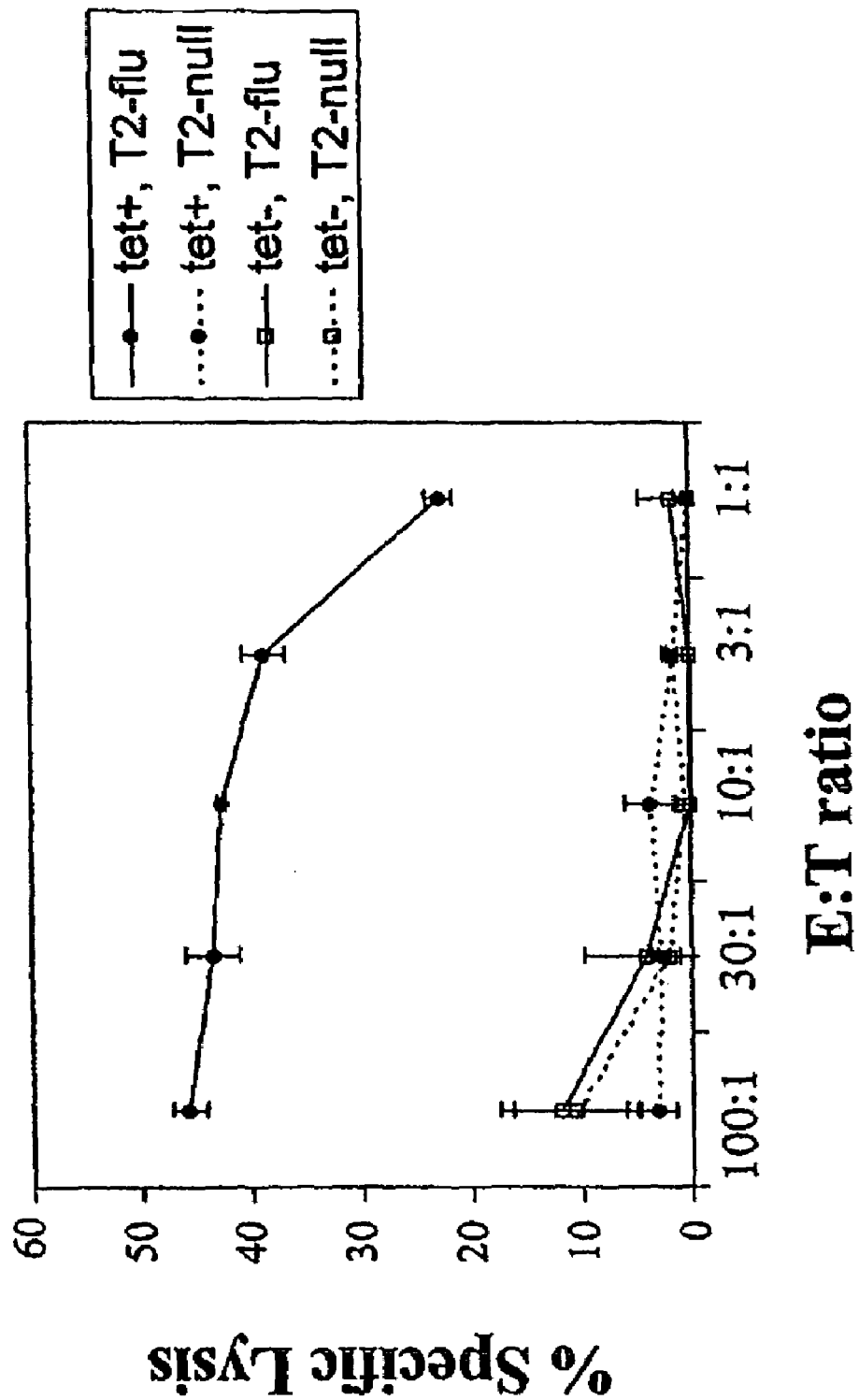

To examine the effector function of the cultured T cells, the antigen-specific cytolytic activity of the flu MP tetramer$^+$ and tetramer$^-$ cultures was determined by $^{51}$Cr release assays on days 26, 30, and 56 of ex vivo expansion (FIG. 3D and data not shown). The HLA-A*0201 TAP deficient T2 cell line, pulsed or unpulsed with the flu MP peptide was used as a target population. At all time points, flu MP tetramer$^+$ cells displayed potent cytotoxicity for flu-MP peptide pulsed targets. Flu MP tetramer$^+$ cells did not kill unpulsed targets, and the Flu MP tetramer$^-$ cells did not kill either pulsed or unpulsed target cells. Neither effector population killed the parental K562 cells, suggesting that killing was MHC-restricted, and not directed at K562 alloantigens (data not shown). Similar results were obtained with both donors (data not shown).

Example 4

Maintenance of Diverse TCR Repertoire by K32/4-1BBL aAPC

Given the finding that many tumor antigens are self antigens, adoptive immunotherapy will require the isolation and propagation of T cells with generally low affinity TCRs. Therefore, it is desirable that the culture system propagate T cells with uniform efficiency. To compare the properties of the cultures grown with aAPCs, cultures of enriched $CD8^+$ T cells grown on anti-CD3/28 coated beads, and K32/CD3/28 and K32/4-1BBL/CD3/28 aAPCs were assessed for maintenance of the initial TCR repertoire. CDR3 size length analysis of TCR β-chains was used because it permits sensitive detection of clonal T cell outgrowth.

Figure 4:
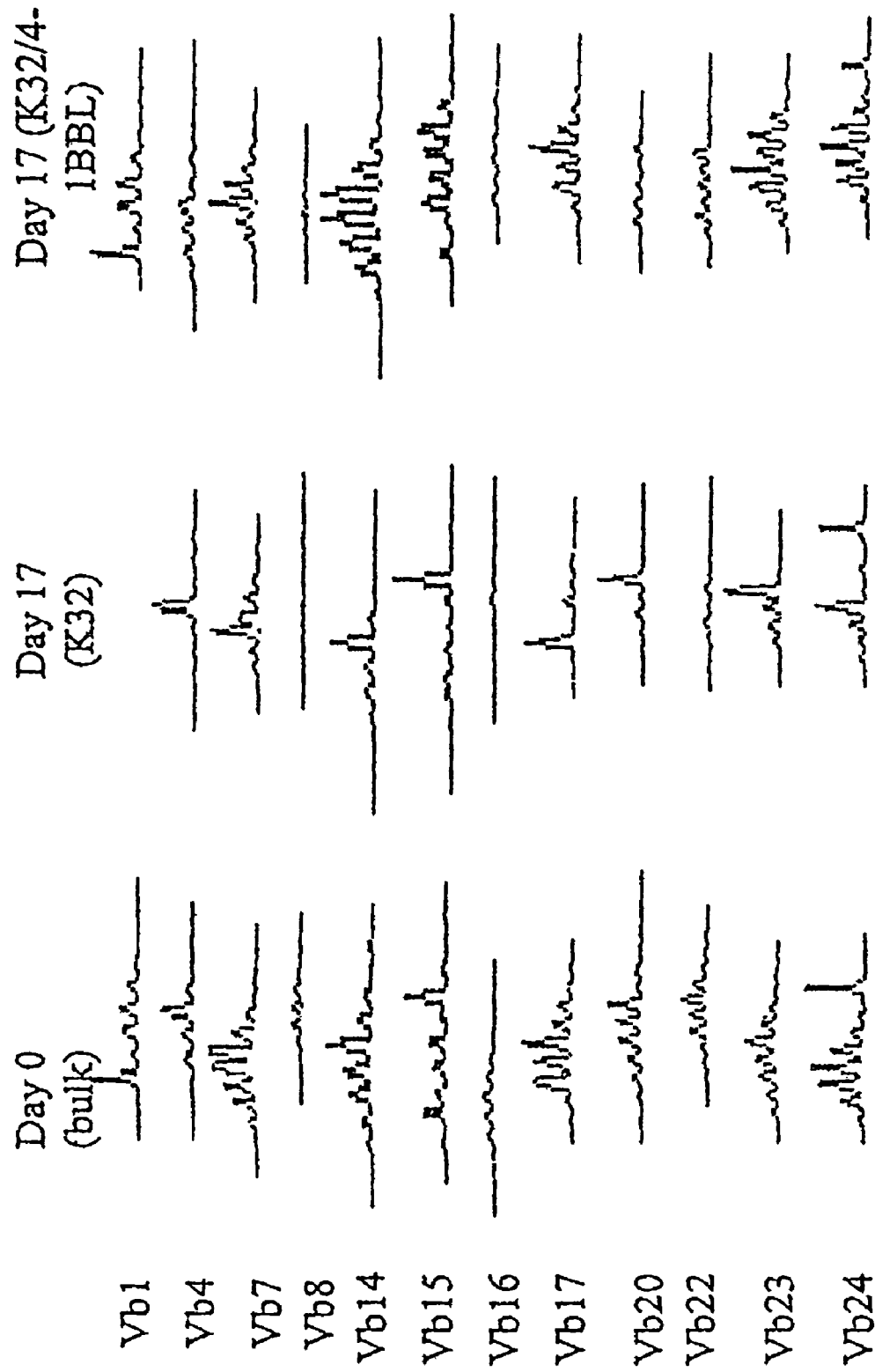
FIG. 4 depicts maintenance of the TCR Vβ repertoire in polyclonal CD8+ T cells after expansion with K32/4-1BBL aAPCs. T cells cultured on K32 or K32/4-1BBL aAPCs from the growth curve shown in FIG. 2 were assessed for the CDR3 length distribution. The indicated TCR Vβ family is shown at baseline, and after 17 days of culture.

It has been previously shown by the inventors that CD3/28 coated beads can maintain diverse $CD4^+$ T cell populations for several months in culture. However, dramatic perturbations of the input $CD8^+$ repertoire occurred after two weeks of culture on these beads. In contrast, enriched $CD8^+$ T cells cultured on K32/4-1BBL/CD3/28 aAPC maintained CDR3 size length distributions that were similar to the input population of T cells (FIG. 4). The addition of 4-1BBL appeared to account for the preservation of the repertoire, because cultures of enriched $CD8^+$ T cells on K32/CD3/28 aAPC did not maintain a comparably diverse repertoire (FIG. 4).

Example 5

K32/4-1BBL aAPC Stimulation Enhances Survival of Human $CD8^+$ T Cells Upon Restimulation Because the initial growth rate of $CD8^+$ T cells stimulated with three different aAPCs was similar, it appeared that the increased overall growth observed in K32/4-1BBL/CD3/28 stimulated T cells was due to improved survival. Therefore, a determination was made of the relative effects of the various aAPCs on Bcl-xL and IL-2 expression, two genes involved in T cell survival and proliferation, respectively.

Figure 5A:
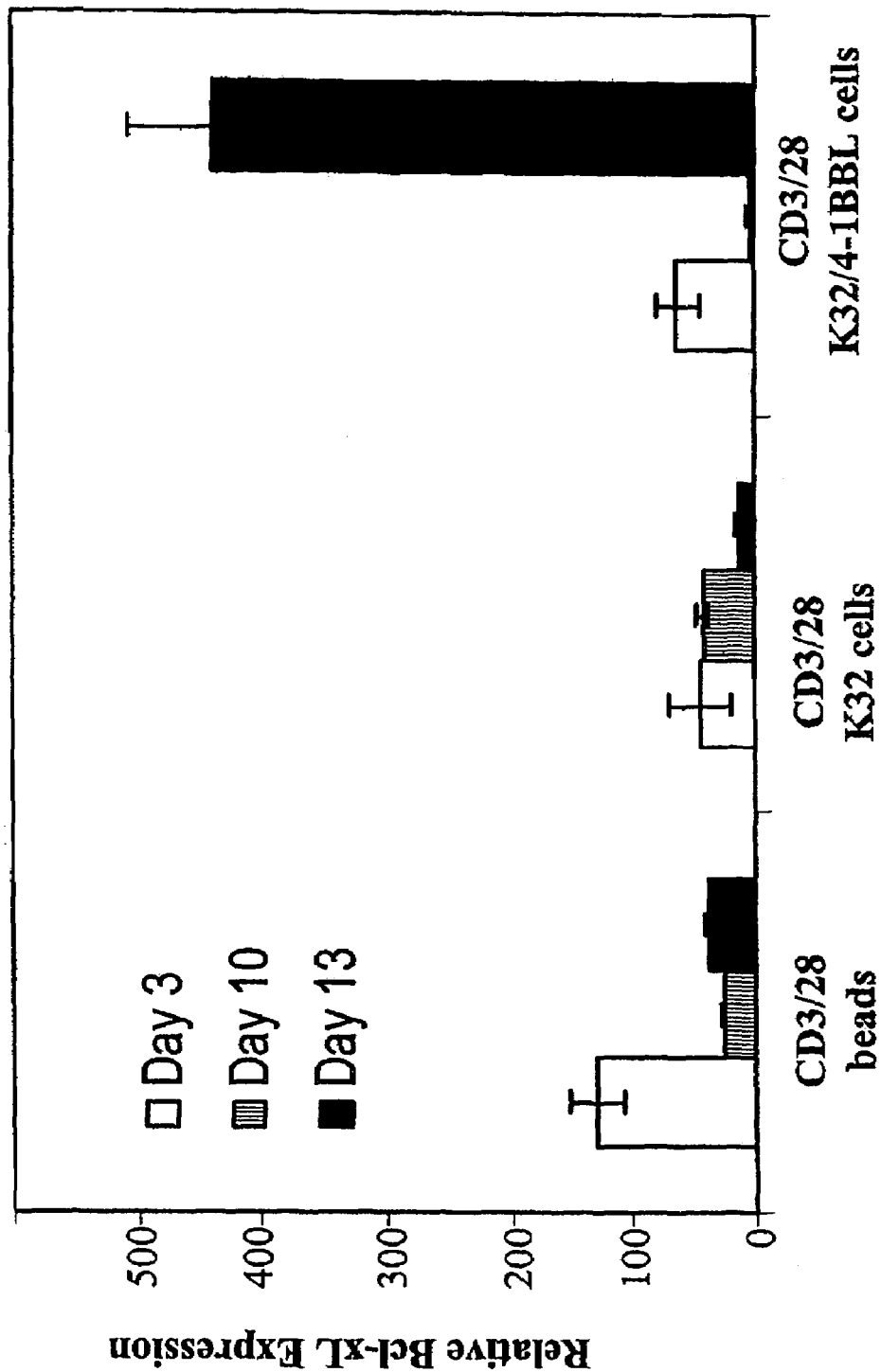
FIGS. 5A and 5B graphically depict expression of genes involved in T cell growth and survival after stimulation with aAPCs. Real-time quantitative RT-PCR of Bcl-xL (mean±s.e.m.) (FIG. 5A) or IL-2 (FIG. 5B) mRNA in polyclonal CD8+ T cultures. Y-axis:—fold expression of Bcl-xL or IL-2 relative to day 0 of culture. All cultures were stimulated with aAPCs on days 0 and 10. Results are representative of three different experiments with different donors.
Figure 5B:
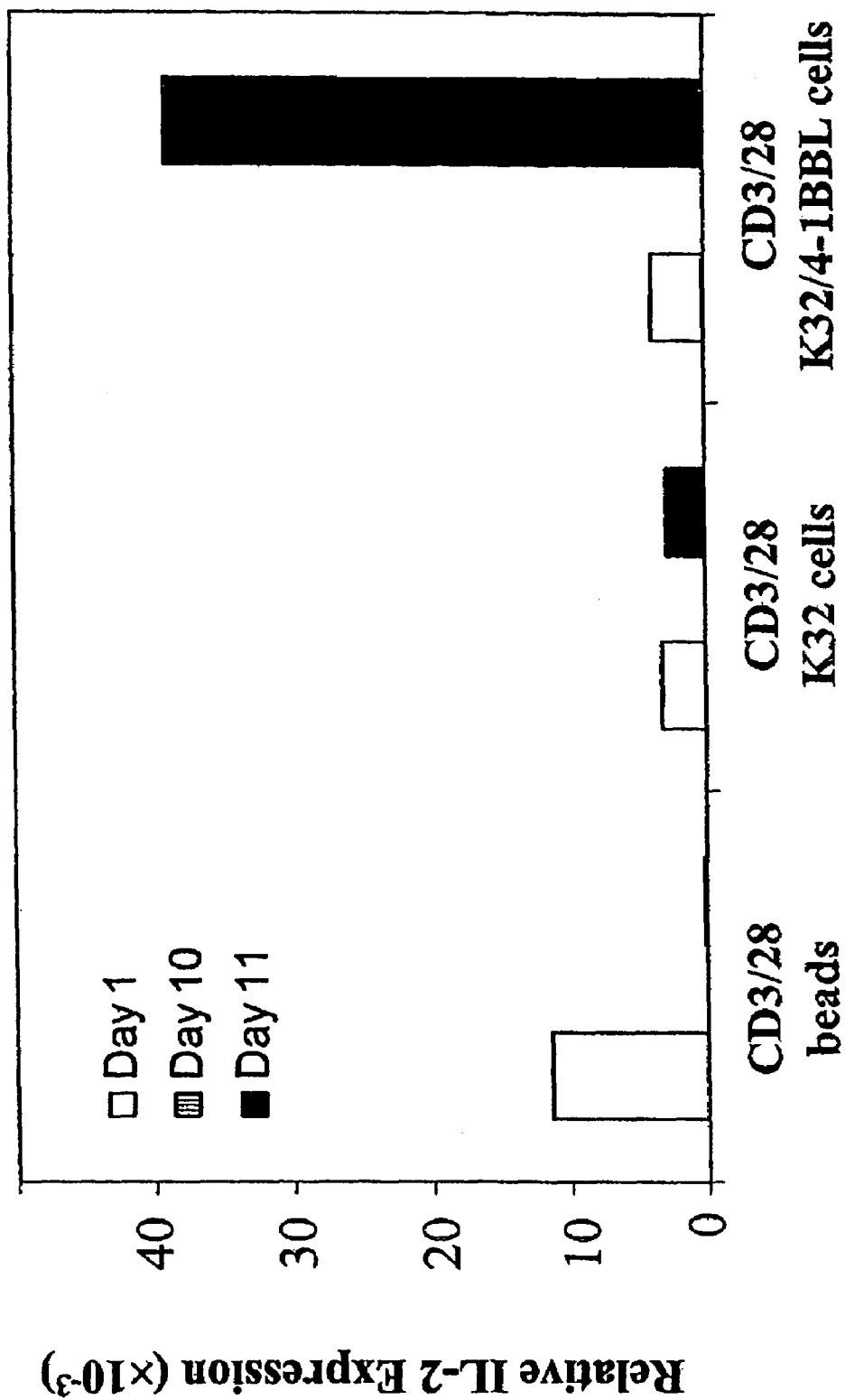

Quantitative real time RT-PCR was used to determine the levels of steady-state mRNA coding for Bcl-xL and IL-2 (FIG. 5). In all cultures, Bcl-xL and IL-2 gene expression was upregulated compared to resting cells one and three days after the first stimulation, and by day 10, Bcl-xL and IL-2 gene expression had returned to resting levels. However, one to three days after re-stimulation, only $CD8^+$ T cell cultures that were stimulated with the K32/4-1BBL/CD3/28 aAPCs had increased levels of Bcl-xL and IL-2 mRNA. In contrast, $CD8^+$ T cells that were stimulated with beads or K32/CD3/28 cells did not re-induce Bcl-xL or IL-2 expression after a second stimulation (FIGS. 5A and B, respectively). Together these data suggest that 4-1BB co-stimulation provides a survival signal that is critical for subsequent but not the initial stimulation of $CD8^+$ T cell proliferation.

Figure 6:
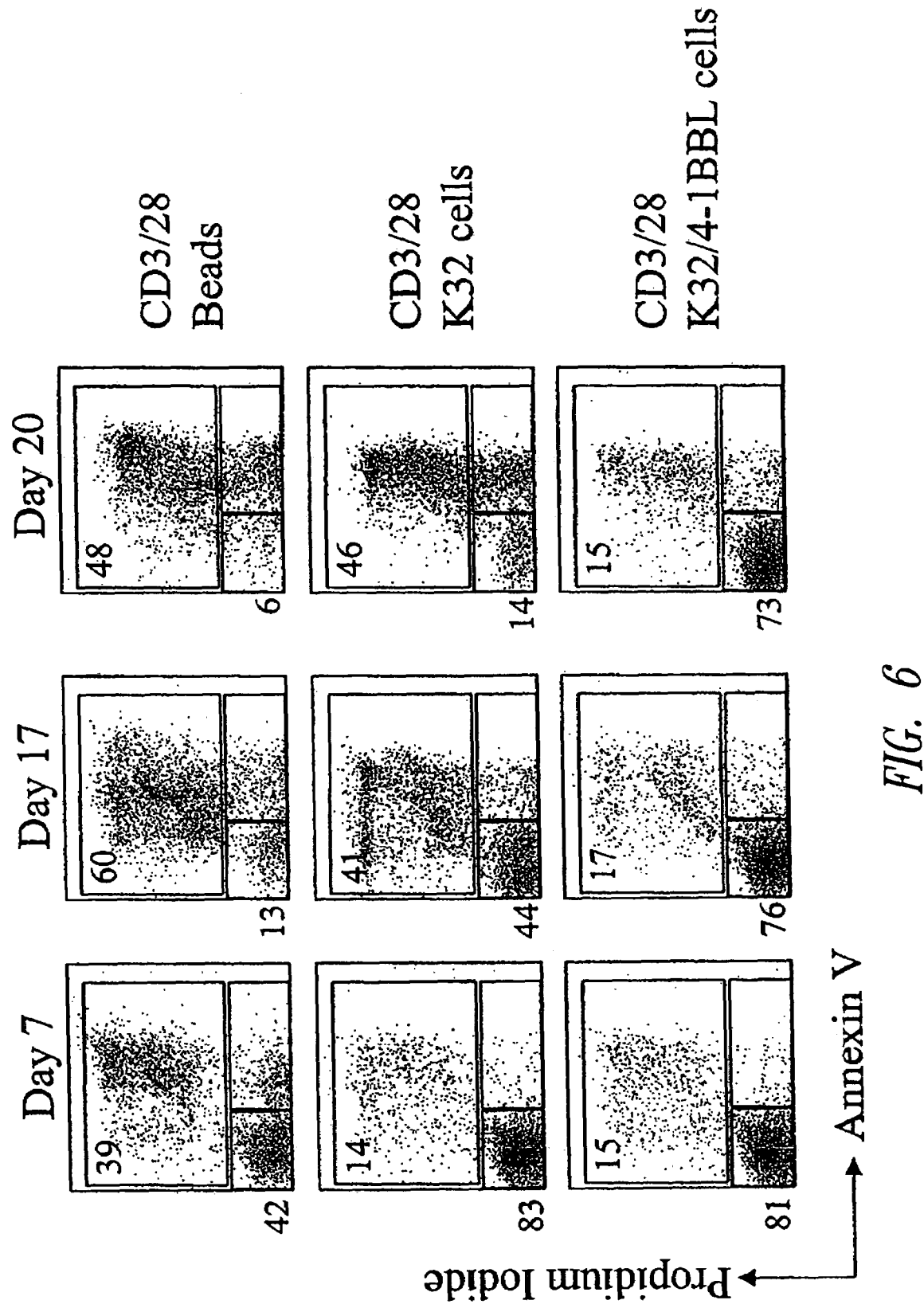
FIG. 6 depicts the distinct effects on apoptosis in cultures of polyclonal human CD8+ T cells stimulated with various aAPCs. Flow-cytometric analysis of cultured cells stained with FITC-labeled annexin V (x-axis) and propidium iodide (y-axis). The three rows represent different aAPCs used for stimulation. The columns represent days in culture. All cultures were stimulated with aAPCs on days 0 and 10. Data shown are not gated. Results are representative of three experiments with different donors.

The viability was assessed of the $CD8^+$ T cells stimulated by the various aAPCs during culture by fluorescent staining with annexin V and propidium iodide (FIG. 6). In the bead-stimulated cultures, viability gradually decreased in the first ten days, and then dropped precipitously as only 6% of cells were viable on day 20. In the T cell cultures stimulated with K32 aAPCs, T cell viability seven days after the second stimulation was improved compared to bead-stimulated cells. However, most of the cells died by day 20.

In contrast, K32/4-1BBL/CD3/28 stimulated CD8+ T cell cultures were >70% viable throughout culture. Together these results show that the addition of 4-1BBL co-stimulation prevents apoptosis and preserves the starting repertoire of CD8+ T cells.

In sum, the K562 cell based aAPC system is able to maintain long term exponential growth of viable T cells, particularly CD8+ memory cells for many months in vitro. Based on a starting cell population of 1 influenza specific CD8+ T cells, a sufficient number of CTL were obtained for therapy after only 30 days of culture. Since the starting number of antigen specific CD8+ T cells could be isolated from only 100 ml of blood, given an initial frequency of 0.05%, it would be possible to decrease the culture time to only two weeks by performing a leukapheresis and isolating $10^5$ to $10^6$ antigen-specific CD8+ T cells. High speed cell sorting or magnetic bead separation can isolate sufficient CD8+ memory cells for initial culture on K32/4-1BBL aAPC coated with anti-CD3 and CD28 antibodies. Alternatively, it is possible to coat the K32/4-1BBL aAPC with the desired tetramer in order to culture antigen specific T cells de novo, and obviate the need for a separate cell isolation procedure. The flexibility of the present system is particularly advantageous, in that the engineering of the aAPC can be modified and focused based upon the specific Tcell need.

One implication of the present system is that the CTLs retain a substantial replicative capacity after culture with the K32/4-1BBL/CD3/28 aAPCs, even after reaching therapeutic numbers for clinical infusion. Several mechanisms appear to account for the improved growth and repertoire of K32/4-1BBL/CD3/28 stimulated CD8+ T cells. For instance, as noted, there was a markedly improved survival of CD8+ T cells after repeated stimulation with K32/4-1BBL/CD3/28 aAPC, as compared with CD3/28 coated beads. With the addition of 4-1BB co-stimulation, CD8+ T cells have increased expression of IL-2 and Bcl-xL, improved survival, and continued proliferation after re-stimulation with anti-CD3/CD28. Thus, 4-1BB stimulation in this context overcomes the previously described activation-induced non-responsiveness.

Not all clinically useful antigens are presently characterized as MHC-restricted epitopes, and the library of MHC tetramers for many HLA types remains limiting. Therefore, K32/4-1BBL/CD3/28 aAPCs were also used to expand CTLs that have been previously enriched for a particular antigen-specificity by priming with autologous DC that have been pulsed with apoptotic bodies of autologous tumor (unpublished data). Thus, K32/4-1BBL/CD3/28 aAPCs are likely to be complementary to many methods, including MHC tetramer sorting (Dunbar et al., *Curr. Biol.* 8:413-416 (1998); Yee, et al., *J. Immunol.* 162:2227-2234 (1999)), or priming with autologous DCs or other artificial APCs (Latouche et al., 2000), that enrich for antigen-specific CTL populations. Although thus far the K32/4-1BBL/CD3/28 aAPCs have been tested for their ability to expand memory or primed T cells; they and other APC constructs will be useful to expand naive CD8+ cells as a source of the 'self' repertoire for tumor immunotherapy (Curtsinger et al., *J. Immunol.* 160:3236-3243 (1998); Sagerstrom et al., *Proc. Natl. Acad. Sci. USA* 90:8987-8991 (1993); Wang et al., *J. Immunol.* 164:1216-1222 (2000).

Expanding low-avidity, self-reactive T cells Voltz et al., *N. Engl. J. Med.* 340:1788-1795 (1999) that can differentiate into memory cells (Tan, *J. Clin. Invest.* 108:1411-1415 (2001)) offers a useful approach to derive therapeutic numbers of self reactive CTLs. Advantageously, because only T cells that recognize the MHC/peptide complex are activated in the present invention, rapid expansion is provided for selected antigen specific clones. Once characterized, these cell lines will be invaluable tools for immunotherapy, particularly since the cell lines permit the design of optimal co-stimulation regimes on a disease-by-disease basis. Moreover, given that GMP preparations of anti-CD3 and CD28 antibodies are currently available, and that K32/4-1BBL aAPC can be grown in serum free medium, the system of the present invention provides therapeutic resources for clinical adoptive immunotherapy for patients with cancer and viral diseases, as well as for the in vitro propagation of CTLs for experimentation. Finally, in light of the many co-stimulatory molecules that continue to be discovered, e.g., OX40L, CD40, CD80, CD86, GL50, 4-1BBL and B7-H1, that serve to either augment the level of T cell growth or alter the functional ability of the T cells, the present invention offers novel methods by which the usefulness of these additional co-stimulators can be evaluated as immunotherapeutic agents by transfecting them into K-32 cells and testing their effect on overall T cell growth and in functional assays.

Example 6

K32 aAPCs with and without CD86 Permit Long-Term Expansion of Human Polyclonal CD4+T Cells Construction and initial testing of K32 aAPCs with and without CD86: We wanted to design an artificial APC (aAPC) that would allow the rapid expansion of human CD4 T cells in an antigen and MHC independent manner. To evaluate different human cell lines in their ability to stimulate CD4 T cell growth, we transfected K562 and U937 cells with CD32 with and without CD86 to create K32, U32 and K32/86 cell lines. Both of these myelogenous leukemia cell lines grow in suspension and the transition of K562 cells, in particular, to clinical trials will be expedited because they do not express MHC molecules that would promote an allogenic response, can easily be killed by natural killer (NK) cells, and grow well in serum free conditions.

To initially characterize the ability of these cell lines to stimulate T cell proliferation, we performed a standard [$^3$H]-thymidine incorporation assay. Irradiated K32+anti-CD3 and CD28 Abs (K32/CD3/28), U32+anti-CD3 and CD28 Abs (U32/CD3/28), K32/86+anti-CD3 Ab cells (K32/86/CD3) and anti-CD3 and CD28 Abs coated beads (CD3/28 coated beads) were used to stimulate freshly isolated human CD4 T cells and [$^3$H]-thymidine incorporation was measured after three days of culture. All cell based aAPC stimulated cultures demonstrated higher [$^3$H]-thymidine uptake than the cells stimulated with CD3/28 coated beads demonstrating that at the level of inducing T cell proliferation, cell based expansion systems were more potent than the bead based system. Control cultures in which the anti-CD3 and anti-CD28 Ab were left out demonstrated minimal (background) levels of [$^3$H]-thymidine, indicating that CD4 T cells rather than the irradiated stimulator cells were responsible for the [$^3$H]-thymidine uptake. K32/CD3/28 and CD3/28 coated bead stimulated cells continued to grow exponentially for ten days without restimulation. Additionally, CD4 T cells stimulated with K32/CD3/28 or K32/CD3/86 underwent on average two more population doublings within the first ten days indicating that it is a more rapid T cell expansion system than the CD3/28 coated beads.

For optimal engraftment potential and possible therapeutic benefit, it is important to ensure that the T cells, after in vitro expansion, are functional and not senescent at the time of re-infusion. To test whether CD4 T cells expanded by K32/CD3/28 aAPCs were able to produce cytokines and survival factors upon restimulation, fresh CD4 T cells were stimulated with either K32/CD3/28 or CD3/28 coated beads and allowed to expand for 10 days. Three days after restimulation, RNA was harvested and cytokine production was measured by quantitative RT-PCR. We observed that CD4 T cells restimulated with K32 CD3/28 could induce a wide array of cytokines (IL-2, IL-10, and IFNγ), a costimulatory molecule (ICOS) and a cell survival factor (Bclx-L) in all cases greater than or equal to as cells stimulated with CD3/28 coated beads.

Furthermore, log linear growth of CD4 T cells was maintained for at least 45 days using the K32/CD3/28, K32/86/CD3 and CD3/28 coated bead expansion systems with all of the cultures undergoing at least two more restimulations demonstrating K32 CD3/28 stimulated cells have the capacity to expand far beyond what is required for immunotherapy trials. At the end of 45 days of culture the K32/CD3/28 stimulated CD4 T cells had undergone 26 population doublings ($6.7 \times 10^7$ fold expansion, data not shown). These studies demonstrate that rapid expansion of CD4 T cells can be achieved using K32/CD3/28 aAPCs and suggest that once these cells are infused back into the patient, they will be at least as functional as CD4 T cells stimulated by CD3/28 coated beads.

One possible use of ex vivo expanded polyclonal T cells is to reconstitute the immune system of immunodeficient individuals. For this therapy to be successful, gaps in the T cell repertoire must not be created by selective expansion of certain T cell subtypes. As described above in Example 4, using Vβ T cell repertoire analysis it was found that $CD8^+$ T cells expanded with K32/4-BBL/CD3/28 were not skewed to any particular Vβ family. These findings were extended using a back calculation method described by Wells et al (Wells, A. D., Gudmundsdottir, H., and Turka, L. A., Following the fate of individual T cells throughout activation and clonal expansion. Signals from T cell receptor and CD28 differentially regulate the induction and duration of a proliferative response. *J. Clin. Invest* 100, 3173-3183, 1997) that measures the number of cells under each peak to determine the percentage of cells that never divided. Table 1 below shows the calculations performed to elucidate what percentage of the resting CD4 T cells stimulated with either K32/CD3/28 or CD3/28 coated beads that divided. Our results from this analysis indicate that upon optimal stimulation with an aAPC the vast majority (95% for K32/CD3/28 and 90% for CD3/28 coated bead stimulated cells) of all human $CD4^+$ T cells can divide.

Table Legend: The vast majority of human CD4 T cells divide upon optimal stimulation. CD4 T cells were labeled with CFSE and stimulated with either K32/CD3/28 or CD3/28 coated beads as described above. After four days of stimulation, the number of cells under each division peak was determined using Flow-Jo software. The absolute number of precursors was determined by dividing the total number of cells by $2^n$ where n=the number of divisions (division peak). The percentage of starting population in each division peak was determined by dividing the absolute number of precursors by the total number of absolute precursors (2012, for K32/CD3/28 and 2016 for CD3/28 coated beads) (Wells, A. D., Gudmundsdottir, H., and Turka, L. A., Following the fate of individual T cells throughout activation and clonal expansion. Signals from T cell receptor and CD28 differentially regulate the induction and duration of a proliferative response. *J.Clin.Invesi* 100, 3173-3183, 1997).

Example 7

Co-Culture with CD3/28 Activated $CD4^+$ T Cells Induces Upregulation of mRNA Encoding for IL-15B7-H1, B7-D and B7-H3 in K32 aAPC Co-culture with CD3/28 activated $CD4^+$ T cells induces upregulation of mRNA encoding for IL-15, B7-H1, B7-D and B7-H3 in K32. Molecules that were preferentially expressed in K32 cells but not U32 cells that may account for their differences to serve as aAPCs and to augment IL-2 production. We hypothesized that crosstalk, between K32/CD3/28 aAPCs and the recently activated $CD4^+$ T cells were inducing the expression of costimulatory molecules on the irradiated K32 cells. Therefore, we assayed for the expression of molecules in the aAPC/CD4 mixtures in the presence or absence of anti-CD3 and anti-CD28 antibodies, allowing us to compare expression of costimulatory molecules and cytokines in the presence or absence of activated $CD4^+$ T cells. Li et al., demonstrated that IL-15 is critical for the onset of T cell division in a murine model (Li, X. C., et al., *Nat. Med.* 7, 114-118, 2001.), making it a candidate responsible for the early onset of cell division in K32/CD3/28 aAPCs stimulated $CD4^+$ T cells. K32 cells constitutively express low levels of mRNA encoding for IL-15. After coculture with activated $CD4^+$ T cells, IL-15 mRNA was upregulated 15-fold. U32 cells did not express IL-15 mRNA either constitutively or after incubation with activated CD4 T cells. In addition to cytokines, differential expression of costimulatory cell surface molecules could also account for the differences in stimulatory capacities between K32 and U32 aAPCs. We did not detect expression of Ox40L or B7-H1 (ICOS ligand) by

TABLE 1

| | K32/CD3/28 | | | CD3/28 Coated Beads | | |
|---|---|---|---|---|---|---|
| Division Peak | Total Number of Cells | Absolute Number of Precursors | % of Starting Population in Each Division Peak | Total Number of Cells | Absolute Number of Precursors | % of Starting Population in Each Division Peak |
| 0 | 106 | 106 | 5 | 213 | 213 | 10 |
| 1 | 555 | 278 | 14 | 916 | 458 | 22 |
| 2 | 2506 | 626 | 31 | 2322 | 580 | 28 |
| 3 | 5144 | 643 | 32 | 3694 | 462 | 22 |
| 4 | 5466 | 342 | 17 | 5534 | 346 | 16 |
| 5 | 558 | 17 | 1 | 1519 | 47 | 2 |

RT-PCR in either K32 or U32. Using flow cytometry, we were unable to detect expression of CD80 or 41BB-L on either K32 or U32 and could not detect CD86 on K32 cells. U32 cells express low levels of CD86. K562 cells do express high levels of ICAM-1 and LFA-3 (Maus, M. V., et al., *Nat. Biotechnol.* 20, 143-148, 2002), but blocking experiments with monoclonal antibodies specific for both ICAM-1 and LFA-3 failed to diminish CD4 cell proliferation, demonstrating that these adhesion molecules are not required for the strong T cell stimulation by K32 cells.

Next, we searched for expression of newly described costimulatory molecules PD-L1, PD-L2 and B7-H3, whose role in human T cell activation has not been clearly established. While we did not detect constitutive expression PD-L1 in K32, U32, or resting CD4$^+$ T cells, we did observe a >45 fold upregulation of PD-L1 mRNA K32/CD3/28 stimulated CD4 T cultures that was not observed in U32/CD3/28 stimulated culture. Likewise, we found a low level of PD-L2 mRNA in resting K32 cells that was modestly upregulated upon K32/CD3 stimulation. Much higher quantities of PD-L2 mRNA were observed in K32/CD3/28 stimulated cultures. Minimal PD-L2 expression was detected in CD4$^+$ T cells mixed with U32/CD3 or U32/CD3/28 aAPCs.

Lastly, we searched for expression of another recently described costimulatory molecule, B7-H3 (Chapoval, A. I., et al., *Nat. Immunol.* 2, 269-274, 2001.). Unlike PD-L1 and PD-L2, B7-H3 was constitutively expressed several thousand-fold over resting CD4$^+$ T cells in K32 cells as compared to U32 aAPCs. Coculture with anti-CD3 and/or anti-CD28 did not significantly change B7-H3 expression in K562 cells suggesting it is unlikely to be a reason K32/CD3/28 stimulated CD4$^+$ T cells expand longer than K32/CD3 activated CD4$^+$ T cells; however, it could explain why K32/CD3 aAPC (i.e. anti-CD28 deficient aAPC) can induce CD4$^+$ T cells to produce IL-2 and expand. To demonstrate that, in fact, the K32 cells were expressing IL-15, PD-L1, PD-L2 and B7-H3 rather than the CD4$^+$ T cells, we treated irradiated K32 with supernatant from T cells activated with K32/CD3/28 or CD3/28 coated beads. We observed similar levels of induction of IL-15 and PD-L1 in K32 cells stimulated with supernatants from K32/CD3/28 or CD3/28 bead activated T cells demonstrating that cell contact between the K562 cell and the T cell is not necessary for the upregulation of these molecules and soluble factors can substitute for activated T cells. B7-H3 was only modestly upregulated in K32 cells after incubation with supernatant from K32/CD3/28 stimulated T cells consistent with minimal upregulation observed. PD-L2 was only slightly induced on K32 cells after incubation with T cell supernatant suggesting that either cell-to-cell contact is necessary to upregulate PD-L2 or a substantial faction of the PD-L2 mRNA upregulation occurred in the T cells. The unexpected expression of these recently described costimulatory ligands in K32 cells may contribute their potency as aAPC.

Example 8

K32/4-1BBL aAPC Driven Expansion of hTERT-Specific CTLs for Adoptive Immunotherapy In this example, K32/4-1BBL/CD3/28 aAPCs were used to expand human telomerase reverse transcriptase (hTERT)-specific CTLs.

In a Phase I study, advanced breast and prostate cancer patients were vaccinated with 5×10$^6$ dentritic cells (DC) pulsed with the hTERT 1540 epitope. Following 6 subcutaneous vaccinations, every other week, immunological responses were evaluated using proliferation assays, MHC class I tetramer analysis of specific T cells, ELISPOT analysis, and chromium release assays. Although undetectable at baseline, hTERT-specific CTL were identified after vaccination by tetramer staining in 4 patients, ranging from 0.26% to 0.58% tetramer$^+$CD8$^+$ cells in uncultured peripheral blood and up to 6.3% tetramer$^+$CD8$^+$ cells after 7 days of in vitro peptide stimulation. These hTERT-specific CTL secreted IFN-γ when challenged during ELISPOT analysis with hTERT peptide but not a negative control peptide, whereas no IFN-γ secreting hTERT-specific cells were identified prior to vaccination. These CTL were functional as shown by the fact that they lysed tumor cells in an MHC-restricted fashion, including HLA-A2$^+$, hTERT$^+$ carcinoma cells, but not HLA-A2-negative, hTERT$^+$ cells.

Figure 7:
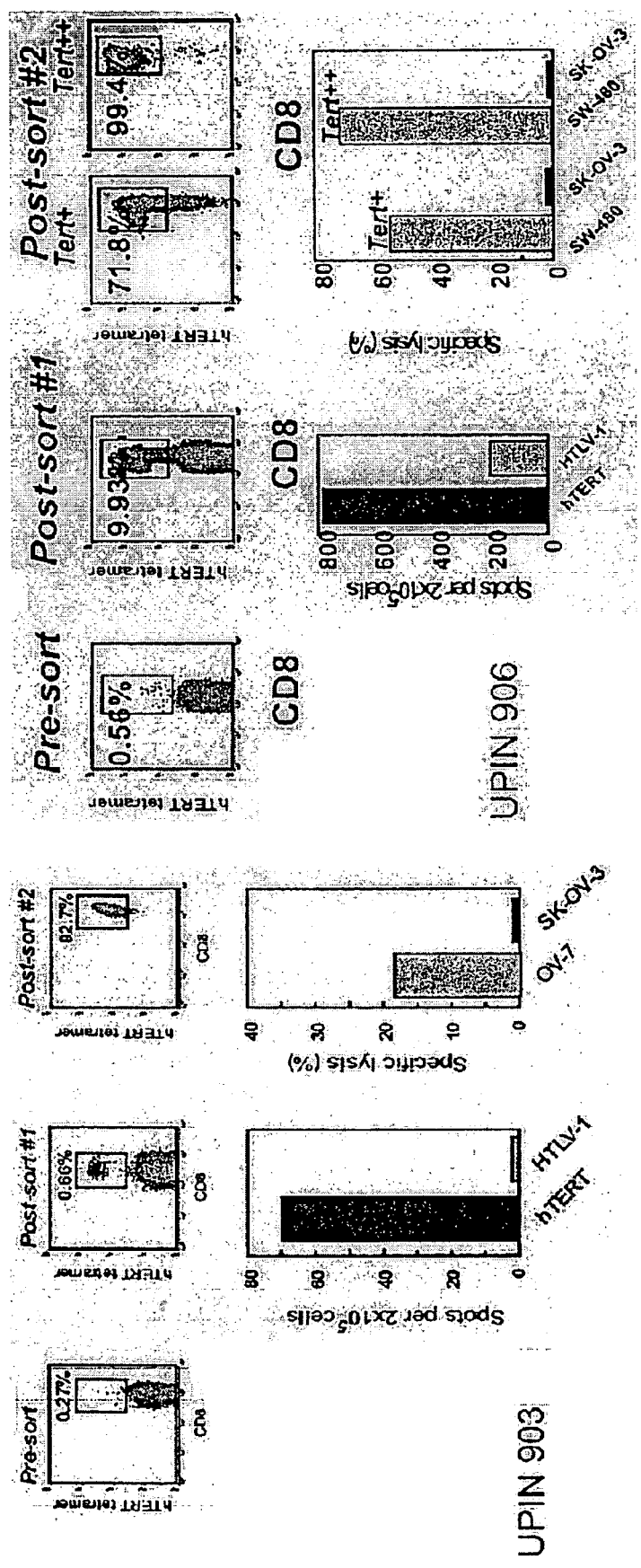
FIG. 7 shows polyclonal expansion and cell sorting of hTERT 1540+ CD8+ cells from 2 different cancer patient. Two rounds of polyclonal expansion and tetramer-guided high speed sorting achieved a nearly pure population of tetramer+ CD8+ cells. IFN-γ secretion was analyzed by ELISPOT after the first sort. Cytolysis of carcinoma cells OV-7 or SW-480 (HLA-A2+, telomerase+) and SK-OV-3 (HLA-A2-, telomerase+) was analyzed after the second sort at an E:T ratio 20:1. For UPIN 906, high- and intermediate-level tetramer-binding T cells were sorted and analyzed separately.

Additionally, as shown in FIG. 7, a nearly pure population of tetramer$^+$ hTERT-specific CD8$^+$ cells were generated from post-vaccine patient samples after 2 rounds of tetramer sorting and expansion using K32/4-1BBL/CD3/28 aAPCs. These hTERT-specific T cells secrete IFN-γ in response to hTERT peptide and lyse HLA-A2$^+$, telomerase-positive carcinoma cells but not HLA-A2-negative, telomerase-positive cells. Cellular expansion was extensive—more than 18 population doublings over 50 days in each of the 2 donors tested. Thus, tetramer-guided CD8$^+$ T cell expansion in this system generates large numbers of polyclonal and functional tumor antigen-specific CD8$^+$ T cells ex vivo, suggesting a platform for the design of TERT-specific adoptive T cell therapy in which TERT-specific T cells are first induced in vivo by vaccination then expanded ex vivo under optimized costimulatory conditions for subsequent re-infusion.

All of the above U.S. patents, U.S. patent application publications, U.S. patent applications, foreign patents, foreign patent applications and non-patent publications referred to in this specification and/or listed in the Application Data Sheet, including but not limited to U.S. patent application Ser. No. 09/960,264, filed Sep. 20, 2001; which is a continuation-in-part of U.S. application Ser. No. 09/794,230, filed Feb. 26, 2001; which claims the benefit of Provisional Application Nos. 60/184,788, filed Feb. 24, 2000, and 60/249,902, filed Nov. 17, 2000, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims. All of references, patents, patent applications, etc. cited above, are incorporated herein in their entirety. Further, all numerical ranges recited herein explicitly include all integer values within the range.

What is claimed is:

1. An engineered multivalent signaling platform (EMSP) comprising a K562 cell line for use in long term expansion of T cells, wherein said K562 comprises on its surface: at least one molecule that is capable of stimulating a primary signal to the T cell, wherein said at least one molecule is an exogenous antibody that binds to CD2; a ligand for CD28, wherein said ligand for CD28 is capable of cross-linking CD28 on T cells and delivering a secondary signal to said T cells, wherein said ligand is selected from the group consisting of anti-CD28 antibody, CD80, and CD86; and wherein said EMSP is further genetically modified to express the co-stimulatory molecule, 4-1BBL.

2. The EMSP of claim 1 wherein said K562 cell line is a cell that is genetically modified to express a human Fcγ receptor.

3. The EMSP of claim 2 wherein said human Fcγ receptor comprises CD32.

4. The EMSP of claim 2 wherein said exogenous antibody is displayed on the surface of said K562 cell line via interaction with the Fcγ receptor.

5. The EMSP of claim 1 wherein said K562 cell line is a cell that has been modified to express a cytokine.

6. The EMSP of claim 5 wherein said cytokine is selected from the group consisting of IL-2, GM-CSF, IL-4, TNF-α, and IFN-γ.

7. The EMSP of claim 1 wherein said T cells comprise $CD4^+$ T cells.

8. The EMSP of claim 1 wherein said T cells comprise $CD8^+$ T cells.

9. The EMSP of claim 1 wherein said T cells comprise regulatory T cells.

10. The EMSP of claim 2, wherein said anti-CD28 antibody is displayed on the surface of said K562 cell line via interaction with the Fcγ receptor.

11. The EMSP of claim 4 wherein said antibody is an anti-CD2 antibody.

12. The EMSP of claim 4 wherein said antibody comprises anti-CD2 and anti-CD28.

13. The EMSP of claim 1, further comprising at least an antigen.

14. The EMSP of claim 13 wherein said antigen is selected from the group consisting of a tumor antigen, a bacterial antigen, a fungal antigen, a viral antigen, and an autoantigen.

15. The EMSP of claim 1 wherein said exogenous antibody is anti-CD2 antibody and said ligand for CD28 is anti-CD28 antibody, further wherein said EMSP induces T cells to remain in exponential growth after a third round of stimulation with said EMSP.

* * * * *